United States Patent
Chen et al.

(10) Patent No.: US 9,815,836 B2
(45) Date of Patent: Nov. 14, 2017

(54) MACROCYCLIC COMPOUNDS AS IRAK1/4 INHIBITORS AND USES THEREOF

(71) Applicant: Merck Patent GmbH, Darmstadt (DE)

(72) Inventors: Xiaoling Chen, Chestnut Hill, MA (US); Henry Yu, Wellesley, MA (US); Ruoxi Lan, Waltham, MA (US); Catherine Jorand-Lebrun, Arlington, MA (US); Theresa L. Johnson, Salem, MA (US); Andreas Goutopoulos, Boston, MA (US)

(73) Assignee: Merck Patent GmbH, Darmstadt (DE)

(*) Notice: Subject to any disclaimer, the term of this patent is extended or adjusted under 35 U.S.C. 154(b) by 0 days.

(21) Appl. No.: 15/620,049

(22) Filed: Jun. 12, 2017

(65) Prior Publication Data

US 2017/0275284 A1  Sep. 28, 2017

Related U.S. Application Data

(62) Division of application No. 15/016,569, filed on Feb. 5, 2016.

(60) Provisional application No. 62/112,374, filed on Feb. 5, 2015.

(51) Int. Cl.
| | |
|---|---|
| *C07D 471/22* | (2006.01) |
| *C07D 498/18* | (2006.01) |
| *C07D 498/22* | (2006.01) |
| *C07D 513/22* | (2006.01) |
| *C07D 487/18* | (2006.01) |

(52) U.S. Cl.
CPC ......... *C07D 471/22* (2013.01); *C07D 487/18* (2013.01); *C07D 498/18* (2013.01); *C07D 498/22* (2013.01); *C07D 513/22* (2013.01)

(58) Field of Classification Search
None
See application file for complete search history.

(56) References Cited

FOREIGN PATENT DOCUMENTS

| WO | 2014058691 A1 | 4/2014 |
|---|---|---|
| WO | 2014121942 A1 | 8/2014 |

OTHER PUBLICATIONS

Chen et al., Clinic Rev Allerg Immunol (2016) 50:1-17.*
Soares-Schanoski et al., Journal of Leukocyte Biology vol. 82, Sep. 2007.*
Berge et al., J. Pharma Sciences, 1977, 66: 1-19.
Buckley, Bioorg. Med Chem Lett., 2008, 18(12): 3656-3660.
Cao, Science, 1996, 271(5252): 1128-31.
Cohen, Current Opinion in Cell Biology, 2009, 21(2): 317-324.
Greene and Wuts, "Protective Groups in Organic Synthesis", Wiley Interscience, 3rd Edition, 1999.
Kocienski Philip J., "Protecting Groups", Georg Thieme Verlag Stuttgart, New York, 1994.
Li, Proc. Natl. Acad. Sci. USA, 2002, 99(8): 5567-5572.
Muzio et al., Science, 1997, 278(5343): 1612-1615.
Ringwood and Li, Cytokine, 2008, 42(1): 1-7.
Wesche, J. Biol. Chem., 1999, 274(27): 19403-19410.
March's Advanced Organic Chemistry, 5th Ed., Ed.: Smith, M.B. and Mar., J., John Wiley & Sons, New York: 2001.
"Organic Chemistry", Thomas Sorrell, University Science Books, Sausalito: 1999.
Periodic Table of the Elements, CAS version, Handbook of Chemistry and Physics, 75th Ed.
PCT International Search Report with PCT Written Opinion of the International Searching Authority.

* cited by examiner

*Primary Examiner* — Karl J Puttlitz
(74) *Attorney, Agent, or Firm* — Dwight D. Kim; EMD Serono Research and Development Institute

(57) ABSTRACT

The present invention relates to compounds of Formula I and pharmaceutically acceptable compositions thereof, useful as IRAK inhibitors.

20 Claims, No Drawings

MACROCYCLIC COMPOUNDS AS IRAK1/4 INHIBITORS AND USES THEREOF

RELATED APPLICATION

This application is a Divisional application of U.S. application Ser. No. 15/016,569, filed on Feb. 5, 2016, which claims the benefit of U.S. Provisional Application No. 62/112,374, filed on Feb. 5, 2015. The entire contents of the aforementioned are hereby incorporated by reference.

TECHNICAL FIELD OF THE INVENTION

The present invention provides for compounds of Formula (I) as IRAK inhibitors and their use in the treatment of cancer, and other diseases related to IRAK overexpression, including rheumatoid arthritis, systemic lupus erythematosus or lupus nephritis.

BACKGROUND OF THE INVENTION

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1 (IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAKI (Muzio et al., 1997. Science 278 (5343): 1612-5). IRAK3 (also called IRAKM) was identified using a murine EST sequence encoding a polypeptide with significant homology to IRAK1 to screen a human phytohemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem Lett. 18(12):3656-60). IRAK1 is essential for the TLR7-mediated and TLR9-mediated activation of IRF7 and the production of interferon-alpha (IFN-α) suggesting that IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

In one aspect, the invention provides compounds of Formula (I):

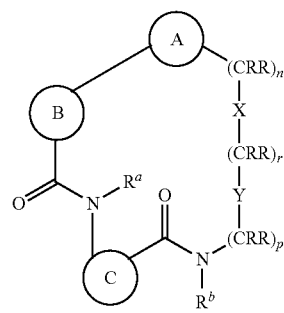

and pharmaceutically acceptable derivatives, solvates, salts, hydrates and stereoisomers thereof.

In another aspect, the invention provides compounds of Formula (I) which are suitable for the treatment and/or prevention of disorders related to IRAK1 and IRAK4. In another aspect, the invention provides compounds which are able to modulate, especially inhibit the activity or function of IRAK1 and IRAK4 in disease states in mammals.

According to another aspect the invention provides methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

In certain embodiments, the present invention provides compounds of Formula (I) which are selective for IRAK-4 and/or IRAK-1. In certain embodiments, the present invention provides compounds of Formula (I) which are selective for IRAK-4 and IRAK-1.

DETAILED DESCRIPTION OF CERTAIN EMBODIMENTS

1. General Description of Compounds of the Invention

In certain aspects, the present invention provides for inhibitors of IRAK. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

According to the invention, bivalent groups include substitution in both directions, and when inserted between any two groups, (e.g., the group "—OC(O)—" or "CO$_2$" inserted between X and Y), includes both

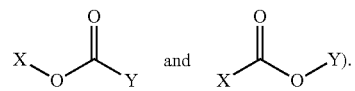

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

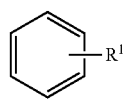

refers to at least

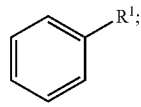

and

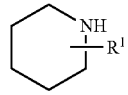

refers to at least

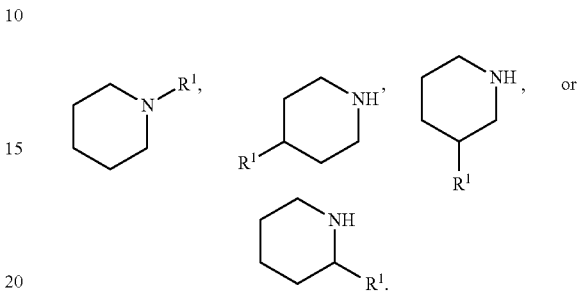

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^o$, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on $R^o$ (or the ring formed by taking two independent occurrences of $R^o$ together with their intervening atoms), are independently deuterium, halogen, $-(CH_2)_{0-2}R^\bullet$, -(haloR$^\bullet$), $-(CH_2)_{0-2}$OH, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^o$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R^*_2))_{2-3}O-$, or $-S(C(R^*_2))_{2-3}S-$, wherein each independent occurrence of R* is selected from hydrogen, $C_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of R* is selected from hydrogen, $C_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which is optionally substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O-heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —$CONH_2$, —CONH-alkyl, —CONH-alkenyl, —CONH-alkynyl, —CONH-carbocyclyl, —CONH-aryl, —CONH-heteroaryl, —CONH-heterocyclyl, —$OCO_2$-alkyl, —$OCO_2$-alkenyl, —$OCO_2$-alkynyl, —$OCO_2$-carbocyclyl, —$OCO_2$-aryl, —$OCO_2$-heteroaryl, —$OCO_2$-heterocyclyl, —$OCONH_2$, —OCONH-alkyl, —OCONH-alkenyl, —OCONH-alkynyl, —OCONH-carbocyclyl, —OCONH-aryl, —OCONH-heteroaryl, —OCONH-heterocyclyl, —NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —$NHCO_2$-alkyl, —$NHCO_2$-alkenyl, —$NHCO_2$-alkynyl, —$NHCO_2$-carbocyclyl, —$NHCO_2$-aryl, —$NHCO_2$-heteroaryl, —$NHCO_2$-heterocyclyl, —NHC(O)$NH_2$, —NHC(O)NH-alkyl, —NHC(O)NH-alkenyl, —NHC(O)NH-alkenyl, —NHC(O)NH-carbocyclyl, —NHC(O)NH-aryl, —NHC(O)NH-heteroaryl, —NHC(O)NH-heterocyclyl, NHC(S)$NH_2$, —NHC(S)NH-alkyl, —NHC(S)NH-alkenyl, —NHC(S)NH-alkynyl, —NHC(S)NH-carbocyclyl, —NHC(S)NH-aryl, —NHC(S)NH-heteroaryl, —NHC(S)NH-heterocyclyl, —NHC(NH)$NH_2$, —NHC(NH)NH-alkyl, —NHC(NH)NH-alkenyl, —NHC(NH)NH-alkenyl, —NHC(NH)NH-carbocyclyl, —NHC(NH)NH-aryl, —NHC(NH)NH-heteroaryl, —NHC(NH)NH-heterocyclyl, —NHC(NH)-alkyl, —NHC(NH)-alkenyl, —NHC(NH)-alkenyl, —NHC(NH)-carbocyclyl, —NHC(NH)-aryl, —NHC(NH)-heteroaryl, —NHC(NH)-heterocyclyl, —C(NH)NH-alkyl, —C(NH)NH-alkenyl, —C(NH)NH-alkynyl, —C(NH)NH— carbocyclyl, —C(NH)NH-aryl, —C(NH)NH-heteroaryl, —C(NH)NH-heterocyclyl, —S(O)— alkyl, —S(O)-alkenyl, —S(O)-alkynyl, —S(O)-carbocyclyl, —S(O)-aryl, —S(O)-heteroaryl, —S(O)-heterocyclyl —$SO_2NH_2$, —$SO_2$NH-alkyl, —$SO_2$NH-alkenyl, —$SO_2$NH-alkynyl, —$SO_2$NH-carbocyclyl, —$SO_2$NH-aryl, —$SO_2$NH-heteroaryl, —$SO_2$NH-heterocyclyl, —NHSO$_2$-alkyl, —NHSO$_2$-alkenyl, —NHSO$_2$-alkynyl, —NHSO$_2$-carbocyclyl, —NHSO$_2$-aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$ (C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect (C$_{max}$), area under the dose response curve (AUC), and F; and in terms of reduced clearance, dose and materials costs.

As used herein, the term "modulator" is defined as a compound that binds to and/or inhibits the target with measurable affinity. In certain embodiments, a modulator has an IC$_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in IRAK activity between a sample comprising a compound of the present invention, or composition thereof, and IRAK, and an equivalent sample comprising IRAK, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups.

The recitation of an embodiment for a variable herein includes that embodiment as any single embodiment or in combination with any other embodiments or portions thereof.

3. Description of Exemplary Compounds

According to one aspect, the present invention provides a compound of formula I,

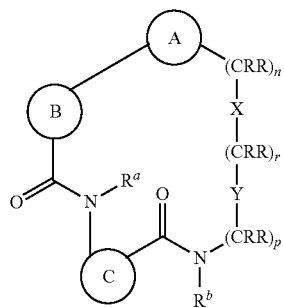

I or a pharmaceutically acceptable salt thereof, wherein:

Ring A is a 5-membered heterocylic ring having 1-4 heteroatoms independently selected from nitrogen, oxygen, or sulfur, or a 5-membered monocyclic heteroaryl ring having 1-4 heteroatoms independently selected from nitrogen, oxygen, or sulfur; each of which is optionally substituted;

Ring B is a 6-membered aryl, or a 6 membered monocyclic heteroaryl ring having 1-4 heteroatoms independently selected from nitrogen, oxygen, or sulfur; each of which is optionally substituted;

Ring C is a 5-membered heterocylic ring having 1-4 heteroatoms independently selected from nitrogen, oxygen, or sulfur, or a 5-membered monocyclic heteroaryl ring having 1-4 heteroatoms independently selected from nitrogen, oxygen, or sulfur; each of which is optionally substituted;

X is absent, —CH=CH—, —C≡C—, —O—, —S—, —SO$_2$—, —SO—, —C(O)—, —CO$_2$—, —C(O)N(R)—, —OC(O)N(R)—, —NRC(O)—, —NRC(O)N(R)—, —NRSO$_2$—, or —N(R)—;

Y is absent, a divalent C$_{3-10}$ aryl, a divalent 3-8 membered saturated or partially unsaturated carbocyclic ring, a divalent 3-7 membered heterocylic ring having 1-4 heteroatoms independently selected from nitrogen, oxygen, or sulfur, or a divalent 5-6 membered monocyclic heteroaryl ring having 1-4 heteroatoms independently selected from nitrogen, oxygen, or sulfur; each of which is optionally substituted;

each R is independently hydrogen, C$_{1-6}$ aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or each R is independently —OR$^c$, —SR$^c$, —SO$_2$R$^c$, —SOR$^c$, —C(O)R$^c$, —CO$_2$R$^c$, —C(O)N(R)R$^c$, —OC(O)N(R)R$^c$, —NRC(O)R$^c$, —NRC(O)N(R)R$^c$, —NRSO$_2$R$^c$, or —N(R)R$^c$;

two R groups on the same atom are taken together with the atom to which they are attached to form a C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

R$^a$ is H or optionally substituted C$_{1-6}$ aliphatic;
R$^b$ is H or optionally substituted C$_{1-6}$ aliphatic;
each R$^c$ is independently H or optionally substituted C$_{1-6}$ aliphatic;
n is 1, 2, 3, 4, or 5;
p is 0, 1, 2, 3, or 4; and
r is 0, 1, or 2.

In certain embodiments, Ring A is an optionally substituted 5-membered heterocylic ring having 1-4 heteroatoms independently selected from nitrogen, oxygen, or sulfur. In certain embodiments, Ring A is an optionally substituted 5-membered monocyclic heteroaryl ring having 1-4 heteroatoms independently selected from nitrogen, oxygen, or sulfur.

In certain embodiments, Ring A is dihydrofuro [2,3-b]tetrahydrofuran, furanyl, furazanyl, imidazolidinyl, imidazolinyl, imidazolyl, isothiazolyl, isoxazolyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrazolidinyl, pyrazolinyl, pyrazolyl, pyrrolidinyl, pyrrolinyl, 2H-pyrrolyl, pyrrolyl, tetrahydrofuranyl, 1,2,3-thiadiazolyl, 1,2,4-thiadiazolyl, 1,2,5-thiadiazolyl, 1,3,4thiadiazolyl, thiazolyl, thienyl, 1,2,3-triazolyl, 1,2,4-triazolyl, 1,2,5-triazolyl, or 1,3,4-triazolyl; each of which is optionally substituted.

In certain embodiments, Ring A is imidazolidinyl, imidazolinyl, imidazolyl, isoxazolyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrazolidinyl, pyrazolinyl, pyrazolyl, pyrrolidinyl, pyrrolinyl, 2H-pyrrolyl, pyrrolyl, 1,2,3-triazolyl, 1,2,4-triazolyl, 1,2,5-triazolyl, or 1,3,4-triazolyl; each of which is optionally substituted.

In certain embodiments, Ring A is pyrazolidinyl, pyrazolinyl, or pyrazolyl; each of which is optionally substituted.

In certain embodiments, Ring A is

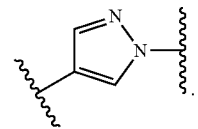 [SMILES: *c1cnn(*)c1]

In certain embodiments, Ring B is an optionally substituted 6-membered aryl. In certain embodiments, Ring B is an optionally substituted 6-membered monocyclic heteroaryl ring having 1-4 heteroatoms independently selected from nitrogen, oxygen, or sulfur.

In certain embodiments, Ring B is phenyl, 2H,6H-1,5,2-dithiazinyl, pyrimidinyl, pyranyl, pyrazinyl, pyridazinyl, pyridinyl, pyridyl, pyrimidinyl, or triazinyl; each of which is optionally substituted.

In certain embodiments, Ring B is phenyl, pyrimidinyl, pyrazinyl, pyridazinyl, pyridinyl, pyridyl, or pyrimidinyl; each of which is optionally substituted.

In certain embodiments, Ring B is phenyl or pyridinyl.
In certain embodiments, Ring B is

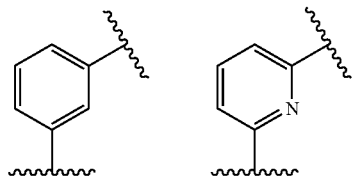

In certain embodiments, Ring C is an optionally substituted 5-membered heterocylic ring having 1-4 heteroatoms independently selected from nitrogen, oxygen, or sulfur. In certain embodiments, Ring C is an optionally substituted 5-membered monocyclic heteroaryl ring having 1-4 heteroatoms independently selected from nitrogen, oxygen, or sulfur.

In certain embodiments, Ring C is dihydrofuro [2,3-b] tetrahydrofuran, furanyl, furazanyl, imidazolidinyl, imidazolinyl, imidazolyl, isothiazolyl, isoxazolyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrazolidinyl, pyrazolinyl, pyrazolyl, pyrrolidinyl, pyrrolinyl, 2H-pyrrolyl, pyrrolyl, tetrahydrofuranyl, 1,2,3-thiadiazolyl, 1,2,4-thiadiazolyl, 1,2,5-thiadiazolyl, 1,3,4thiadiazolyl, thiazolyl, thienyl, 1,2,3-triazolyl, 1,2,4-triazolyl, 1,2,5-triazolyl, or 1,3,4-triazolyl; each of which is optionally substituted.

In certain embodiments, Ring C is imidazolidinyl, imidazolinyl, imidazolyl, isoxazolyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrazolidinyl, pyrazolinyl, pyrazolyl, pyrrolidinyl, pyrrolinyl, 2H-pyrrolyl, pyrrolyl, 1,2,3-triazolyl, 1,2,4-triazolyl, 1,2,5-triazolyl, or 1,3,4-triazolyl; each of which is optionally substituted.

In certain embodiments, Ring C is pyrazolidinyl, pyrazolinyl, or pyrazolyl; each of which is optionally substituted.

In certain embodiments, Ring C is

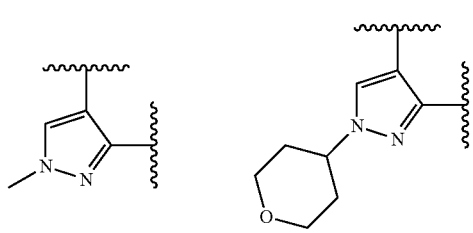

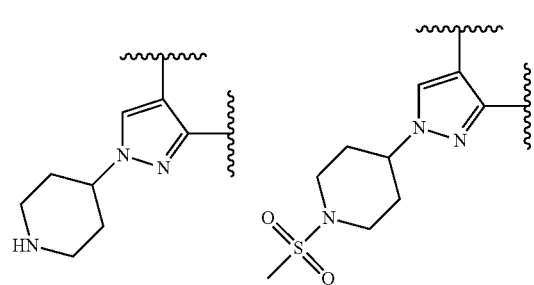

-continued

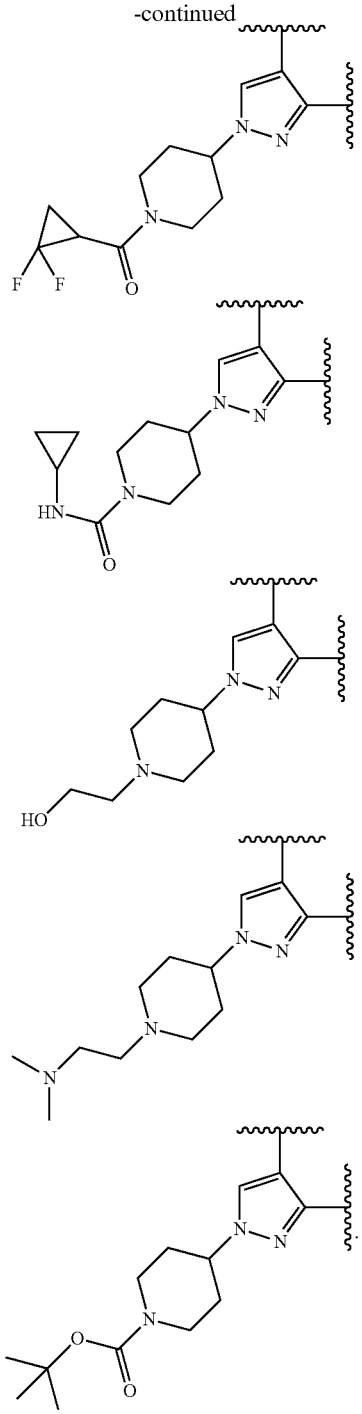

In certain embodiments, $R^a$ is H.
In certain embodiments, $R^a$ is optionally substituted $C_{1-6}$ aliphatic. In certain embodiments, $R^a$ is methyl, ethyl, ethyl, propyl, i-propyl, butyl, s-butyl, t-butyl, straight or branched pentyl, or straight or branched hexyl; each of which is optionally substituted.

In certain embodiments, $R^b$ is H.
In certain embodiments, $R^b$ is optionally substituted $C_{1-6}$ aliphatic. In certain embodiments, $R^b$ is methyl, ethyl, ethyl, propyl, i-propyl, butyl, s-butyl, t-butyl, straight or branched pentyl, or straight or branched hexyl; each of which is optionally substituted.

In certain embodiments, X is absent.

In certain embodiments, X is —CH═CH—, —O—, —S—, —SO₂—, —SO—, —C(O)—, —CO₂—, —C(O)N(R)—, —OC(O)N(R)—, —NRC(O)—, —NRC(O)N(R)—, —NRSO₂—, or —N(R)—.

In certain embodiments, X is —CH═CH—, —C≡C—, —O—, —S—, —SO₂—, —SO—, —C(O)—, —CO₂—, —C(O)N(H)—, —OC(O)N(H)—, —NHC(O)—, —NHC(O)N(H)—, —NHSO₂—, or —N(H)—.

In certain embodiments, X is —CH═CH—, —C≡C—, —O—, —S—, —SO₂—, —SO—, —C(O)—, —CO₂—, —C(O)N(Me)-, —OC(O)N(Me)-, —NMeC(O)—, —NMeC(O)N(Me)-, —NMeSO₂—, or —N(Me)-.

In certain embodiments, X is —CH═CH—, —C≡C—, —O—, —S, —SO₂—, —SO—, —CO₂—, —OC(O)N(Me)-, or —N(Me)-.

In certain embodiments, Y is absent.

In certain embodiments, Y is a divalent C₃₋₁₀ aryl, a divalent 3-8 membered saturated or partially unsaturated carbocyclic ring, a divalent 3-7 membered heterocylic ring having 1-4 heteroatoms independently selected from nitrogen, oxygen, or sulfur, or a divalent 5-6 membered monocyclic heteroaryl ring having 1-4 heteroatoms independently selected from nitrogen, oxygen, or sulfur; each of which is optionally substituted.

In certain embodiments, Y is an optionally substituted divalent C₃₋₁₀ aryl. In certain embodiments, Y is an optionally substituted divalent 3-8 membered saturated or partially unsaturated carbocyclic ring. In certain embodiments, Y is an optionally substituted divalent 3-7 membered heterocylic ring having 1-4 heteroatoms independently selected from nitrogen, oxygen, or sulfur. In certain embodiments, Y is an optionally substituted divalent 5-6 membered monocyclic heteroaryl ring having 1-4 heteroatoms independently selected from nitrogen, oxygen, or sulfur.

In certain embodiments, Y is an optionally substituted divalent phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl.

In certain embodiments, Y is an optionally substituted divalent pyrrolidine, piperidine, or morpholine.

In certain embodiments, Y is

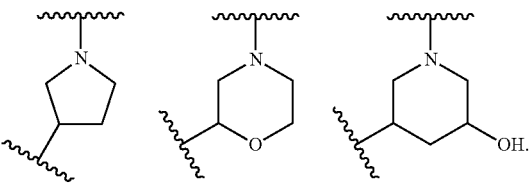 [SMILES: *C1CCN(*)C1 ; *C1CN(*)CCO1 ; *C1CC(O)CN(*)C1]

In certain embodiments, n is 1, 2, 3, or 4.

In certain embodiments, p is 0, 1, or 2.

In certain embodiments, r is 0.

In certain embodiments, each of Ring A, Ring B, Ring C, X, Y, R, $R^a$, $R^b$, n, p, and r, is as defined above and described in embodiments, classes and subclasses above and herein, singly or in combination.

In certain embodiments, the present invention provides a compound of formula I-a,

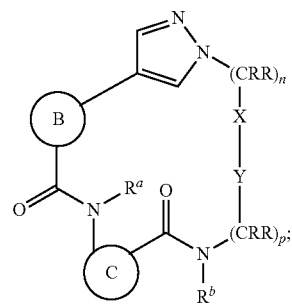

I-a or a pharmaceutically acceptable salt thereof, wherein each of Ring B, Ring C, X, Y, R, $R^a$, $R^b$, n, and p, is as defined above and described in embodiments, classes and subclasses above and herein, singly or in combination.

In certain embodiments, the present invention provides a compound of formula I-b,

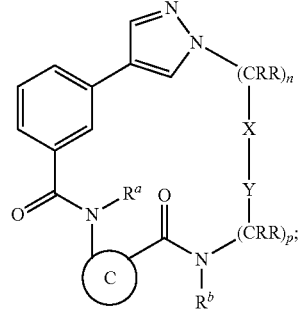

I-b or a pharmaceutically acceptable salt thereof, wherein each of Ring C, X, Y, R, $R^a$, $R^b$, n, and p, is as defined above and described in embodiments, classes and subclasses above and herein, singly or in combination.

In certain embodiments, the present invention provides a compound of formula I-c,

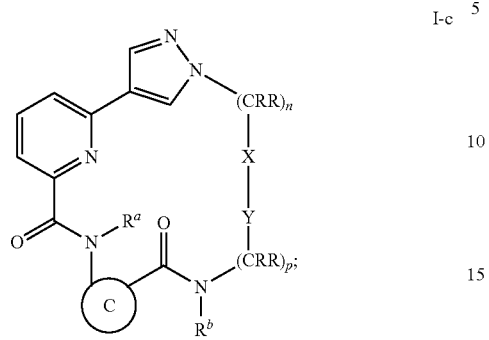

I-c or a pharmaceutically acceptable salt thereof, wherein each of Ring C, X, Y, R, $R^a$, $R^b$, n, and p, is as defined above and described in embodiments, classes and subclasses above and herein, singly or in combination.

In certain embodiments, the present invention provides a compound of formula I-d,

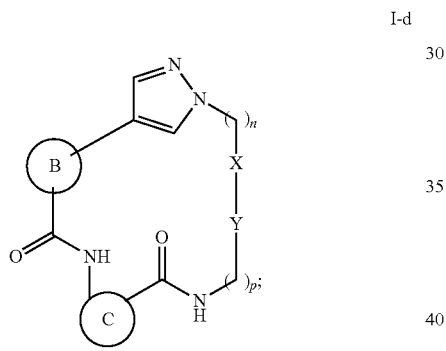

I-d or a pharmaceutically acceptable salt thereof, wherein each of Ring B, Ring C, X, Y, R, $R^a$, $R^b$, n, p, and r, is as defined above and described in embodiments, classes and subclasses above and herein, singly or in combination.

In certain embodiments, the invention provides a compound selected from Table 1:

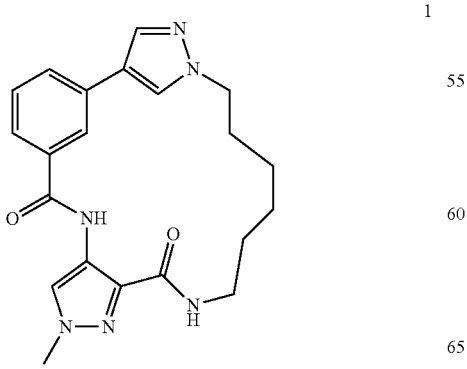

1

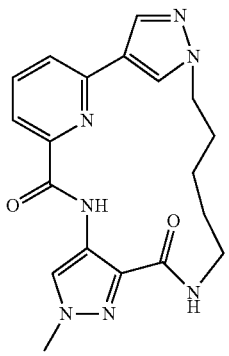

2

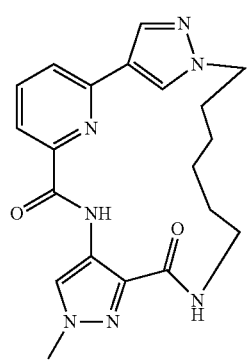

3

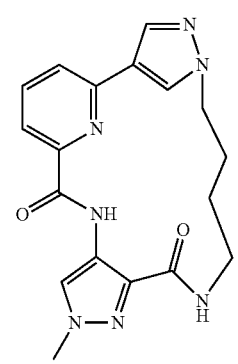

4

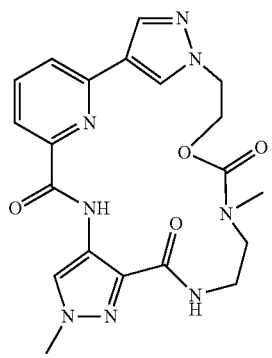

5

6
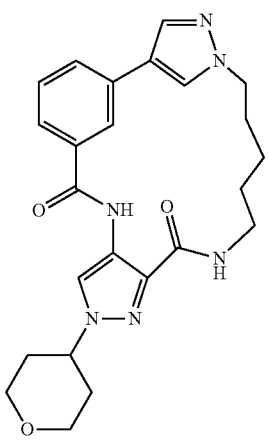
7
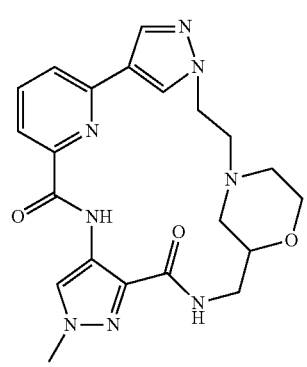
8
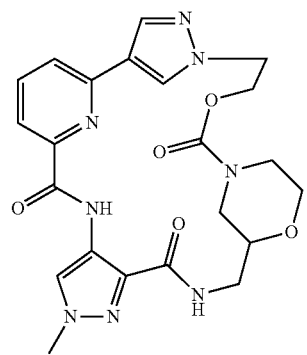
9
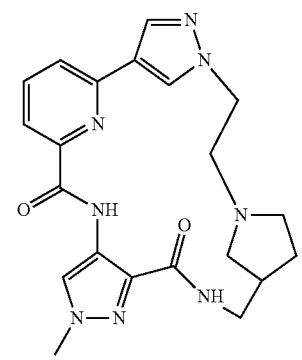
10
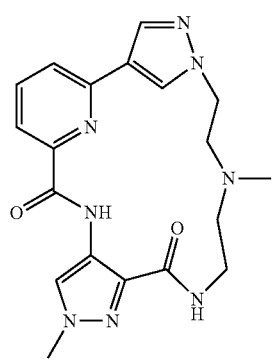
11
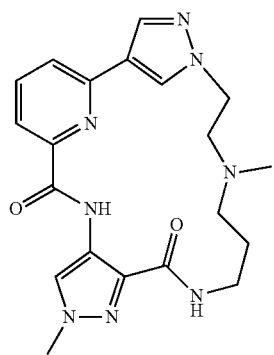
12
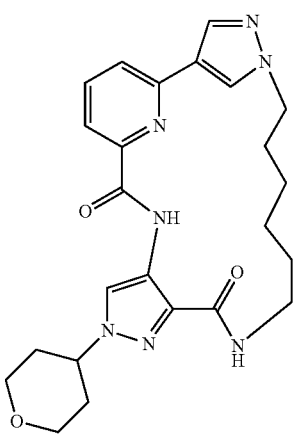
13
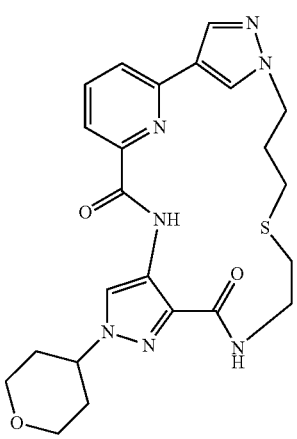

14
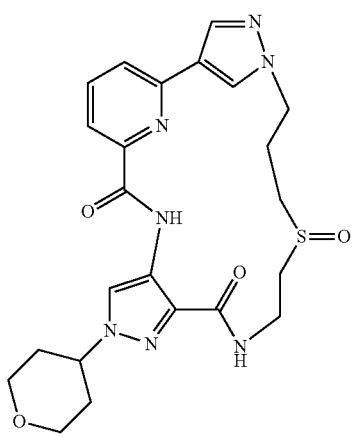
15
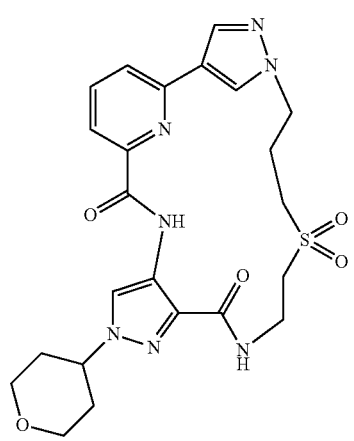
16
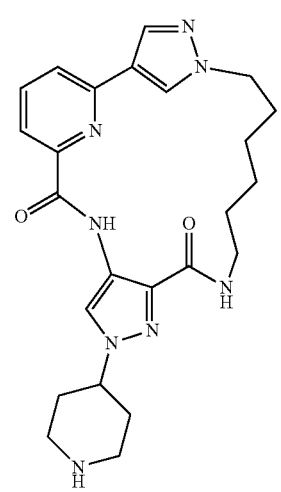
17
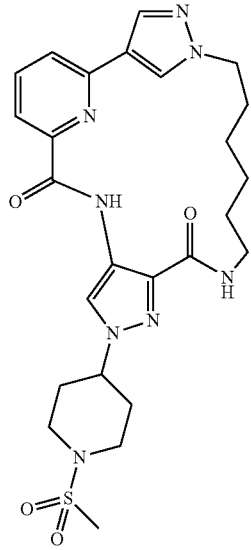
18
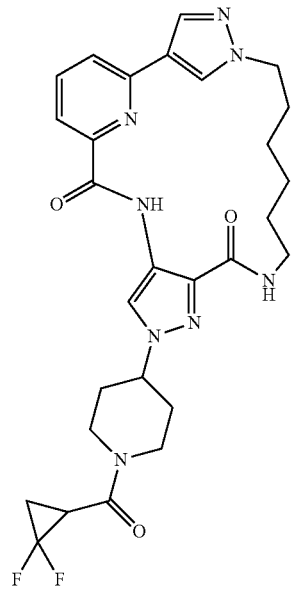
19
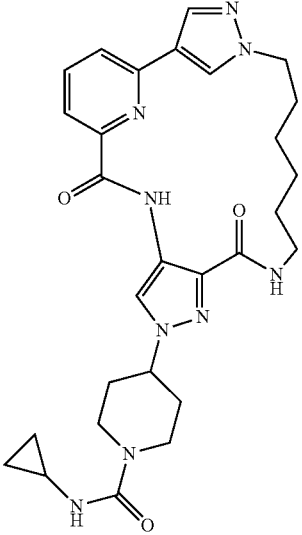

20
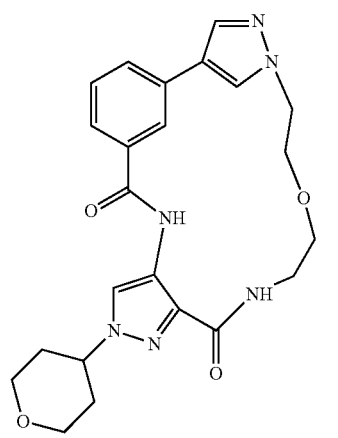
21
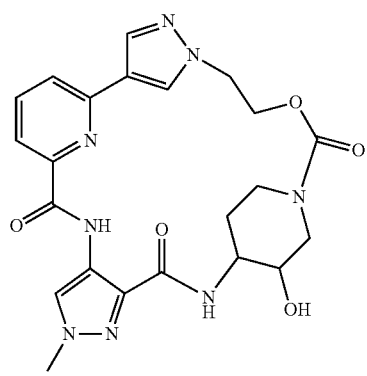
22
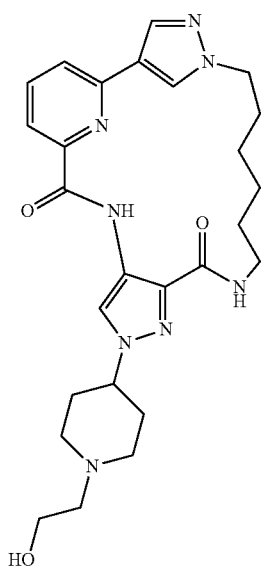
23
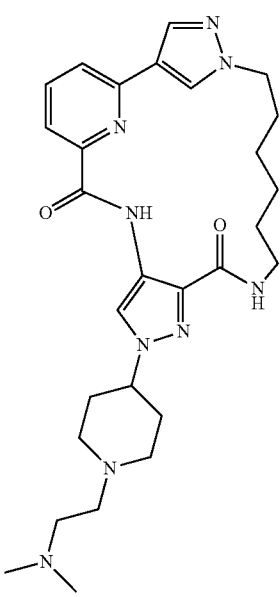
24
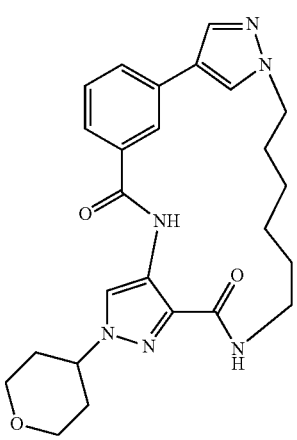
25
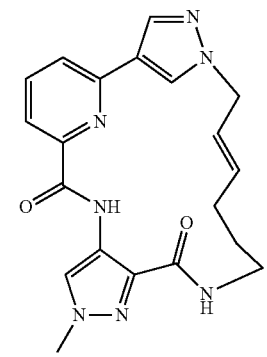

25
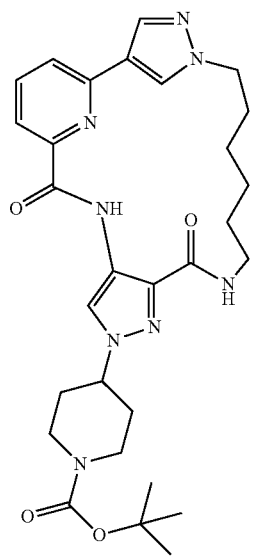
26
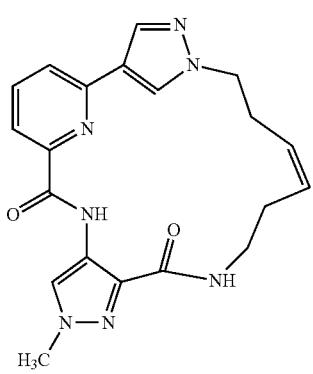
27
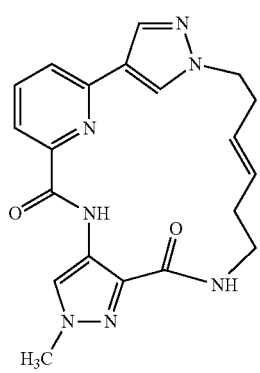
28
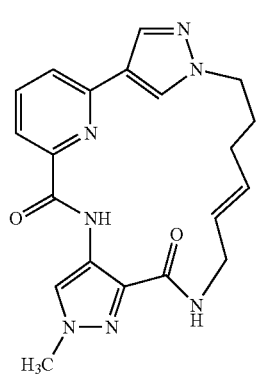
30
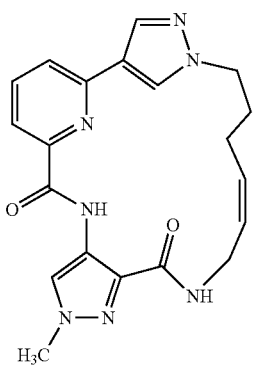
31
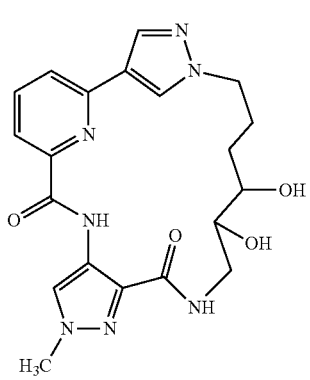
32
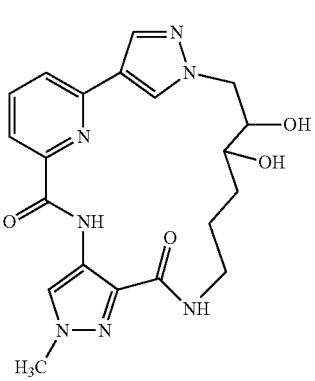
33
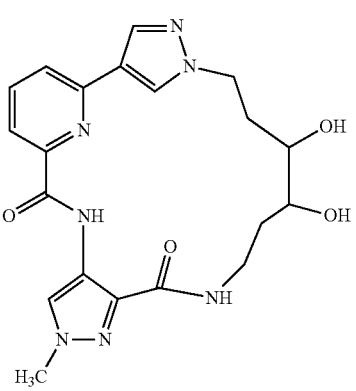

34 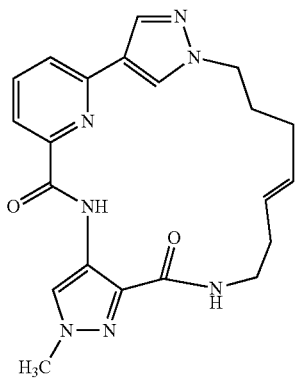

38 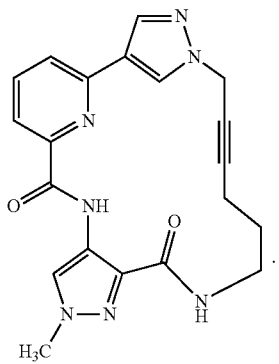

In some embodiments, the present invention provides a compound selected from those depicted above, or a pharmaceutically acceptable salt thereof.

In certain embodiments, the compounds of the invention provide for decreased cytotoxicity or low cytotoxicity in a PBMC cellular assay.

Various structural depictions may show a heteroatom without an attached group, radical, charge, or counterion. Those of ordinary skill in the art are aware that such depictions are meant to indicate that the heteroatom is attached to hydrogen (e.g., 35 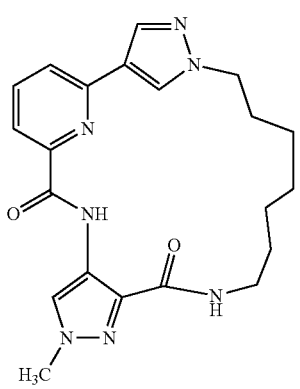

is understood to be

36 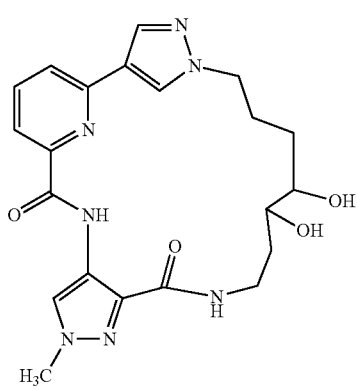

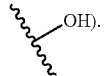).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit IRAK, or a mutant thereof, in a biological sample or in a patient. In certain embodiments, the amount of compound in compositions of this invention is such that is effective to measurably inhibit IRAK, or a mutant thereof, in a biological sample or in a patient. In certain embodiments, a composition of this invention is formulated for administration to a patient in need of such composition.

37 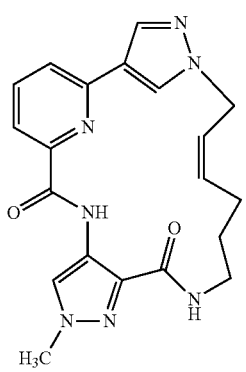

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this aremineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from an IRAK related disorder, comprising administering to said subject an effective amount of a compound of formula I and related formulae.

The present invention preferably relates to a method, wherein the IRAK associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality.

The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

The present invention furthermore relates to a method wherein the immunoregulatory abnormality is bone marrow or organ transplant rejection or graft-versus-host disease.

The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

In certain embodiments, disorders associated with IRAK are selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

In certain embodiments, the cancer is selected from carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

In certain embodiments, the cancer is brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. In some embodiments, the cancer is metastatic cancer. In some embodiments, the cancer is colorectal cancer. In some embodiments, the cancer is colon cancer.

In various embodiments, compounds of formula (I), and related formulae exhibit a IC50 for the binding to IRAK of less than about 5 µM, preferably less than about 1 µM and even more preferably less than about 0.100 µM.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit IRAK activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing IRAK-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of IRAK activity if expedient.

The invention also relates to the use of compounds according to formula (I) and/or physiologically acceptable salts thereof for the prophylactic or therapeutic treatment and/or monitoring of diseases that are caused, mediated and/or propagated by IRAK activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by IRAK activity. In certain embodiments, the invention provides the use of a compound according to formula I or physiologically acceptable salts thereof, for the production of a medicament for the prophylactic or therapeutic treatment of a IRAK-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with IRAK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with IRAK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];
Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;
DNA altering agents: such as amrubicin, bisantrene, decitabine, mitoxantrone, procarbazine, trabectedin, clofarabine; amsacrine, brostallicin, pixantrone, laromustine[1,3]; Topoisomerase Inhibitors: such as etoposide, irinotecan, razoxane, sobuzoxane, teniposide, topotecan; amonafide, belotecan, elliptinium acetate, voreloxin;
Microtubule modifiers: such as cabazitaxel, docetaxel, eribulin, ixabepilone, paclitaxel, vinblastine, vincristine, vinorelbine, vindesine, vinflunine; fosbretabulin, tesetaxel;
Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;
Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;
Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];
Aromatase inhibitors: such as aminoglutethimide, anastrozole, exemestane, fadrozole, letrozole, testolactone; formestane;
Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];
Photosensitizers: such as methoxsalen[3]; porfimer sodium, talaporfin, temoporfin;
Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabaluma[1,3], EMD-525797[4], nivolumab[1,3];
Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];
Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];
Vaccines: such as sipuleucel[3]; vitespen[3], emepepimut-S[3], oncoVAX[4], rindopepimut[3], troVax[4], MGN-1601[4], MGN-1703[4]; and
Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1]Prop. INN (Proposed International Nonproprietary Name); [2]Rec. INN (Recommended International Nonproprietary Names); [3]USAN (United States Adopted Name); [4]no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting IRAK activity in a biological sample comprising the step of contacting said biological sample with a compound of this invention, or a composition comprising said compound.

According to another embodiment, the invention relates to a method of inhibiting IRAK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of IRAK, including the evaluation of the many factors thought to influence, and be influenced by, the production of IRAK and the interaction of IRAK. The present compounds are also useful in the development of other compounds that interact with IRAK since the present compounds provide important structure-activity relationship (SAR) information that facilitate that development. Compounds of the present invention that bind to IRAK can be used as reagents for detecting IRAK in living cells, fixed cells, in biological fluids, in tissue homogenates, in purified, natural biological materials, etc. For example, by labeling such compounds, one can identify cells expressing IRAK. In addition, based on their ability to bind IRAK, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing IRAK inside permeabilized cells. The compounds of the invention can also be utilized as commercial research reagents for various medical research and diagnostic uses. Such uses can include but are not limited to: use as a calibration standard for quantifying the activities of candidate IRAK inhibitors in a variety of functional assays; use as blocking reagents in random compound screening, i.e. in looking for new families of IRAK ligands, the compounds can be used to block recovery of the presently claimed IRAK compounds; use in the co-crystallization with IRAK enzyme, i.e. the compounds of the present invention will allow formation of crystals of the compound bound to IRAK, enabling the determination of enzyme/compound structure by x-ray crystallography; other research and diagnostic applications, wherein IRAK is preferably activated or such activation is conveniently calibrated against a known quantity of an IRAK inhibitor, etc.; use in assays as probes for determining the expression of IRAK in cells; and developing assays for detecting compounds which bind to the same site as the IRAK binding ligands.

The compounds of the invention can be applied either themselves and/or in combination with physical measurements for diagnostics of treatment effectiveness. Pharmaceutical compositions containing said compounds and the use of said compounds to treat IRAK-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of IRAK, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade).

All reactions were conducted at room temperature unless otherwise noted. All compounds of the present invention were synthesized by processes developed by the inventors.

$^1$H NMR was recorded on a Bruker 400 MHz spectrometer, using residual signal of deuterated solvent as internal reference. Chemical shifts (δ) are reported in ppm relative to the residual solvent signal (δ=2.49 ppm for 1H NMR in DMSO-d6). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

LCMS-Analysis was performed under the following conditions:
Method: A: 0.1% TFA in H$_2$O, B: 0.1% TFA in ACN:
Runtime: 6.5 min
Flow Rate: 1.0 mL/min
Gradient: 5-95% B in 4.5 min, wavelength 254 and 215 nM.
Column: Waters Sunfire C18, 3.0×50 mm, 3.5 um, +ve mode
Mass Scan: 100-900 Da Compound numbers utilized in the Examples below correspond to compound numbers set forth supra.

The following abbreviations refer to the abbreviations used below:
Ac (acetyl), BINAP (2,2'-bis(disphenylphosphino)-1,1'-binaphthalene), dba (dibenzylidene acetone), Bu (Butyl), tBu (tert-Butyl), DCE (dichloroethane), DCM (Dichloromethane), δ (chemical shift), DIEPA (di-isopropyl ethylamine), DMA (dimethyl acetamide), DMSO (Dimethyl Sulfoxide), DMF (N,N-Dimethylformamide), Dppf (1,1-bis (diphenyl phosphine ferrocene)), EA (Ethyl acetate), EtOH (Ethanol), eq (equivalent), g (gram), cHex (Cyclohexane), HATU (N-[(Dimethylamino)(3H-[1,2,3]triazolo[4,5-b]pyridin-3-yloxy)methylene]-N-methylmethanaminiumhexafluoro phosphate), HPLC (High Performance Liquid Chromatography), h/hr (hour), LDA (lithium diisopropyl amine), LiHMDS (lithium bis(trimethylsilyl)amide), MHz (Megahertz), MeOH (Methanol), min (minute), mL/ml (milliliter), mmol (millimole), mM (millimolar), mp (melting point), MS (Mass Spectrometry), MW (microwave), NMR (Nuclear Magnetic Resonance), O/N (overnight), PBS (Phosphate Buffered Saline), SNAP (silica gel column), RT (room temperature), TEA (Triethyl amine), TFA (Trifluoroacetic acid), THF (Tetrahydrofuran), TLC (Thin Layer Chromatography).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

$^1$H NMR was recorded on a Bruker 400 MHz spectrometer, using residual signal of deuterated solvent as internal reference. Chemical shifts (δ) are reported in ppm relative to the residual solvent signal (δ=2.49 ppm for 1H NMR in DMSO-d6). 1H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

LCMS-Analysis was performed under the following conditions:
Method: A: 0.1% TFA in H$_2$O, B: 0.1% TFA in ACN:
Runtime: 6.5 min
Flow Rate: 1.0 mL/min
Gradient: 5-95% B in 4.5 min, wavelength 254 and 215 nM.
Column: Waters Sunfire C18, 3.0×50 mm, 3.5 um, +ve mode
Mass Scan: 100-900 Da

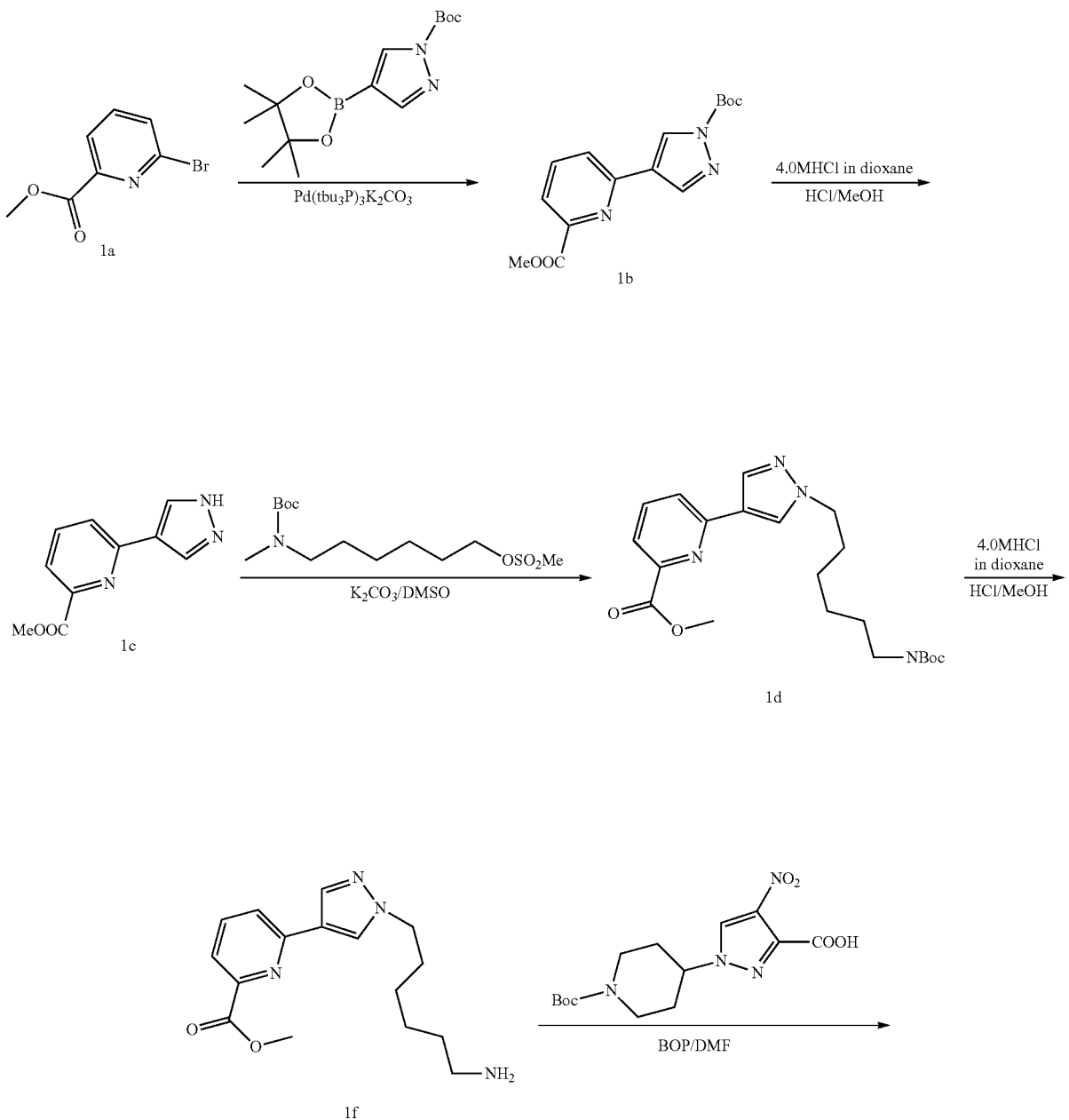

Scheme 1

-continued
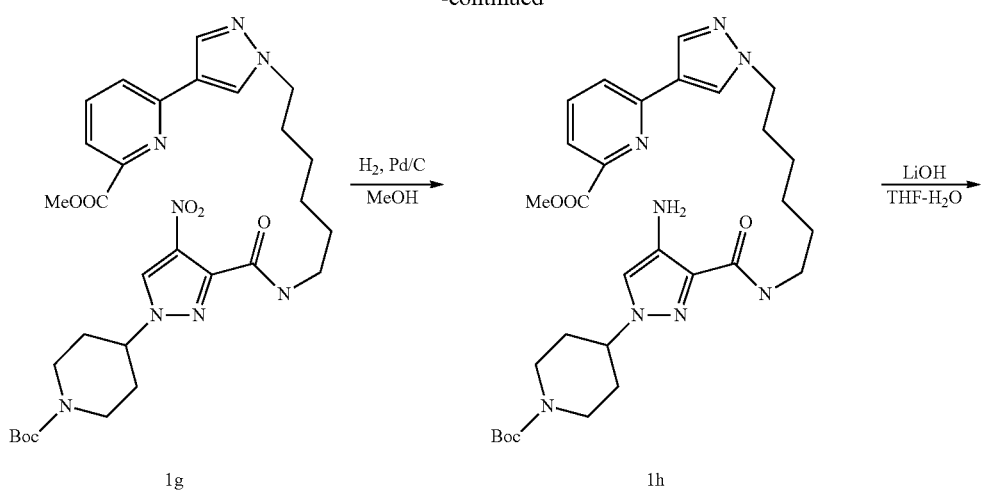
1g → 1h
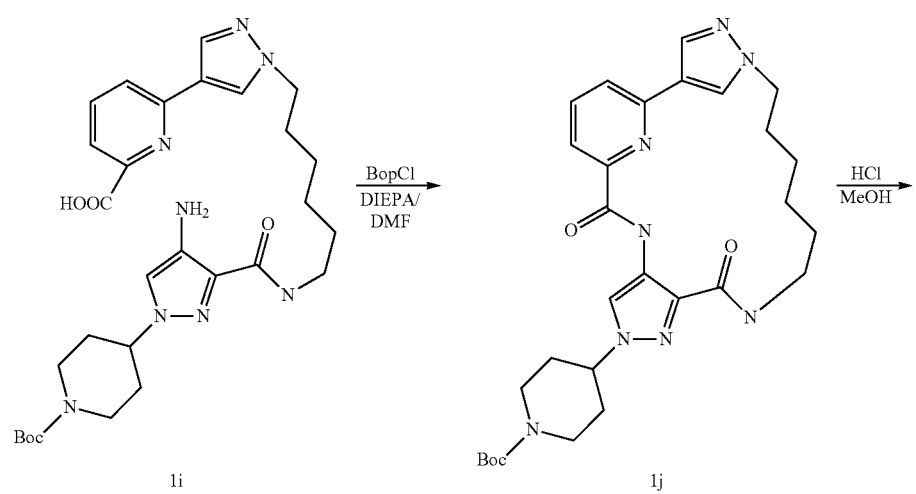
1i → 1j
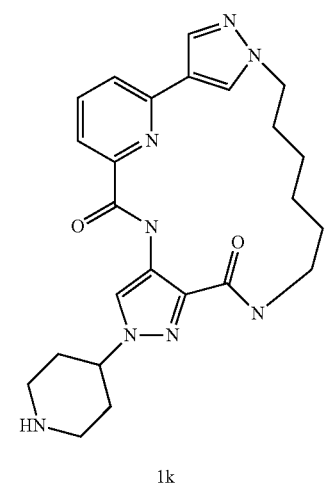
1k

Intermediates

6-(1-tert-Butoxycarbonyl-1H-pyrazol-4-yl)-pyridine-2-carboxylic acid methyl ester (1b)

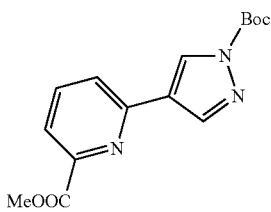 [SMILES: COC(=O)c1cccc(-c2cnn(C(=O)OC(C)(C)C)c2)n1]

A mixture of 6-Bromo-pyridine-2-carboxylic acid methyl ester (4940 mg; 22.87 mmol; 1.00 eq.), 4-(4,4,5,5-Tetramethyl-[1,3,2]dioxaborolan-2-yl)-pyrazole-1-carboxylic acid tert-butyl ester (7399 mg; 25.15 mmol; 1.10 eq.), potassium carbonate (3476 mg; 25.15 mmol; 1.10 eq.) in dioxane (130 mL) and water (13 mL) was degassed, then to it was added palladium tritert-butylphosphane (584 mg; 1.14 mmol; 0.05 eq.), and the mixture was stirred at 40° C. for 24 hr. LC-MS showed the clean desired compound. The reaction solution was diluted with EA (100 mL), washed with brine (100 mL×2), dried, evaporated, and the resulting residue was treated with ether. The solid precipitated out, was filtered to provide 5500 mg of the title compound as a white solid. Yield 79%. LC-MS (M+1): 304.

6-(1H-Pyrazol-4-yl)-pyridine-2-carboxylic acid methyl ester (1c)

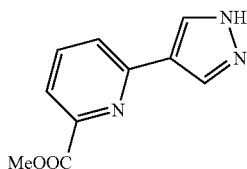 [SMILES: COC(=O)c1cccc(-c2cn[nH]c2)n1]

To a solution of 6-(1-tert-Butoxycarbonyl-1H-pyrazol-4-yl)-pyridine-2-carboxylic acid methyl ester (5500 mg; 18.13 mmol; 1.00 eq.) in methanol (30 mL) was added 4.0M HCl in dioxane hydrogen chloride (36266 mL; 145.06 mmol; 8.00 eq.) at 0° C., and the mixture was stirred at RT for 3 hr. LC-MS showed the reaction was completed. The reaction solution was diluted with EA (30 mL), filtered, and the collected solid was dissolved water (50 mL). Disodium carbonate (5765 mg; 54.40 mmol; 3.00 eq.) was added, stirred for 1 hr at RT, filtered, and collected to provide the title compound as a white solid (2500 mg). Yield 68%. LC-MS (M+1): 204.

6-[1-(6-Amino-hexyl)-1H-pyrazol-4-yl]-pyridine-2-carboxylic acid methyl ester (1d)

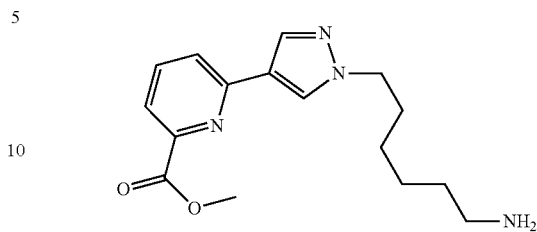

A mixture of 6-(1H-Pyrazol-4-yl)-pyridine-2-carboxylic acid methyl ester (1000 mg; 4.92 mmol; 1.00 eq.), methanesulfonic acid 6-tert-butoxycarbonylamino-hexyl ester (1599 mg; 5.41 mmol; 1.10 eq.) and $Cs_2CO_3$ (1763 mg; 5.41 mmol; 1.10 eq.) in DMF (10 mL) was stirred at 80° C. for 3 hr. LC-MS showed the desired compound. The reaction was cooled, diluted with water (50 mL), extracted with DCM (100 mL×2), and the organic layer was washed with brine and dried, providing the residue as 6-[1-(6-tert-Butoxycarbonylamino-hexyl)-1H-pyrazol-4-yl]-pyridine-2-carboxylic acid methyl ester. To the above product was added methanol (6 mL), and 4.0M hydrogen chloride in dioxane (6.15 mL; 24.61 mmol; 5.00 eq.), and stirred at RT for overnight. The solvent was removed and the residue was dissolved in water (10 mL), washed with EA (10 mL×2). The organic layer was discarded, and to the aqueous layer was added disodium carbonate (1304 mg; 12.30 mmol; 2.50 eq.). The mixture was extracted with DCM (100 mL×2), the organic layers were combined, washed with Brine (20 mL), dried over $MgSO_4$ and the solvent was evaporated affording 1310 mg of the title compound as a white off solid. Yield 88%. LC-MS (M+1): 303.

6-[1-(6-{[1-(1-tert-Butoxycarbonyl-piperidin-4-yl)-4-nitro-1H-pyrazole-3-carbonyl]-amino}-hexyl)-1H-pyrazol-4-yl]-pyridine-2-carboxylic acid methyl ester (1e)

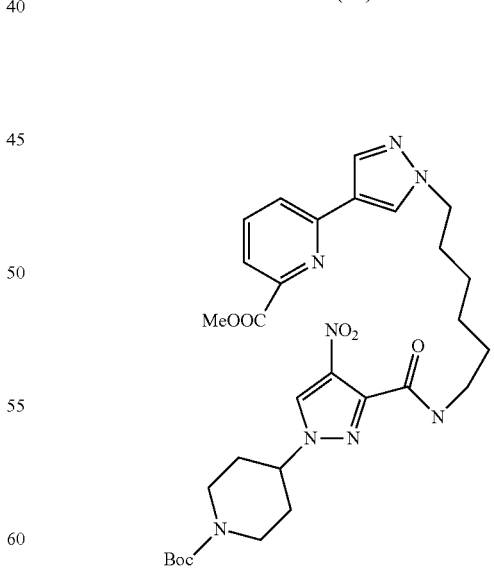

A mixture of 4-(3-Carboxy-4-nitro-pyrazol-1-yl)-piperidine-1-carboxylic acid tert-butyl ester lithium (490.00 mg; 1.42 mmol; 1.00 eq.), HATU (1317 mg, 3.47 mmol, 1.2 eq) and Ethyl-diisopropyl-amine (0.31 mL; 1.77 mmol; 1.25 eq.) in DMF (10 mL) were stirred at RT for 10 min. 6-[1-(6-Amino-hexyl)-1H-pyrazol-4-yl]-pyridine-2-carboxylic acid methyl ester (385.10 mg; 1.27 mmol; 0.90 eq.) was added and the mixture was stirred for 2 hr at RT. The solvent was removed, water was added (40 mL), extracted with DCM (100×2), and the organic layer was washed with aqueous 5% NaHCO₃, then brine. The solvent was removed and the crude product was purified by SNAP column (100G eluented with 20-100% EA in hexane), providing the title compound (210 mg, yield 23%). LC-MS (M+1): 625.

6-[1-(6-{[4-Amino-1-(1-tert-butoxycarbonyl-piperidin-4-yl)-1H-pyrazole-3-carbonyl]-amino}-hexyl)-1H-pyrazol-4-yl]-pyridine-2-carboxylic acid methyl ester (1f)

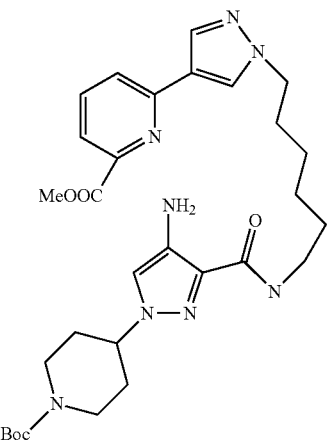 [SMILES: COC(=O)c1cccc(-c2cnn(CCCCCCNC(=O)c3nn(C4CCN(C(=O)OC(C)(C)C)CC4)cc3N)c2)n1]

To a solution of 6-[1-(6-{[1-(1-tert-Butoxycarbonyl-piperidin-4-yl)-4-nitro-1H-pyrazole-3-carbonyl]-amino}-hexyl)-1H-pyrazol-4-yl]-pyridine-2-carboxylic acid methyl ester (450.00 mg; 0.72 mmol; 1.00 eq.) in 40 mL methanol was added 10% Pd/C 280 mg (wet). The mixture was put on a par shaker at 50 psi for 2 hr at RT, the catalyst was filtered off, and the solvent was removed, providing a residue as the title compound, which was directly used for the next step reaction. LC-MS (M+1): 595.

Lithium 6-[1-(6-{[4-Amino-1-(1-tert-butoxycarbonyl-piperidin-4-yl)-1H-pyrazole-3-carbonyl]-amino}-hexyl)-1H-pyrazol-4-yl]-pyridine-2-carboxylate (1g)

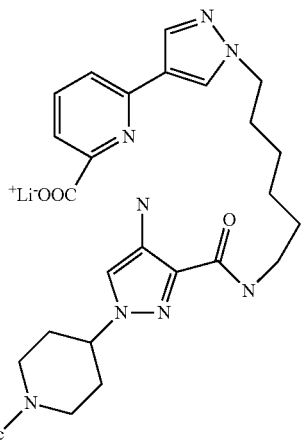

A mixture of Lithium 6-[1-(6-{[4-Amino-1-(1-tert-butoxycarbonyl-piperidin-4-yl)-1H-pyrazole-3-carbonyl]-amino}-hexyl)-1H-pyrazol-4-yl]-pyridine-2-carboxylate (428 mg; 0.72 mmol; 1.00 eq.), lithium hydroxide hydrate (60 mg; 1.44 mmol; 2.00 eq.) in THF (2 mL) and water (2 mL) was stirred at RT for 20 min. LC-MS indicated the reaction was completed. The solvent was removed and the residue was directly used for the next step reaction. LC-MS (M+1): 580.

Example 1: tert-butyl 4-{13,20-dioxo-4,5,12,15,16, 19,25-heptaazatetracyclo[19.3.1.1²,⁵.0¹⁴,¹⁸]hexacosa-1(24),2(26),3,14,17,21(25),22-heptaen-16-yl}piperidine-1-carboxylate (26)

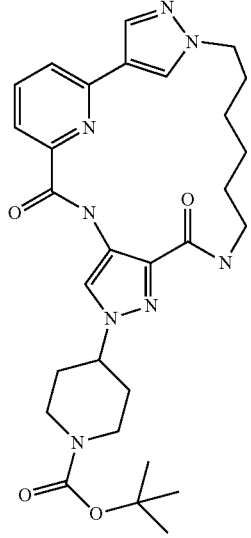 [SMILES: CC(C)(C)OC(=O)N1CCC(n2cc3c(n2)C(=O)NCCCCCCn2cc(cn2)-c2cccc(n2)C(=O)N3)CC1]

A mixture of lithium 6-[1-(6-{[4-Amino-1-(1-tert-butoxycarbonyl-piperidin-4-yl)-1H-pyrazole-3-carbonyl]-amino}-hexyl)-1H-pyrazol-4-yl]-pyridine-2-carboxylate (422 mg; 0.72 mmol; 1.00 eq.), Ethyl-diisopropyl-amine (0.27 mL; 1.51 mmol; 2.10 eq.) in DCM (50 mL) was added to 3-[chloro-(2-oxooxazolidin-3-yl)phosphoryl]oxazolidin-2-one (219 mg; 0.86 mmol; 1.20 eq.), and stirred at RT for 4 days. DIEPA (0.05 mL) and 3-[chloro-(2-oxooxazolidin-3-yl)phosphoryl]oxazolidin-2-one (50 mg) were added, and the reaction was stirred for another 17 hr until reaction was completed by LC-MS. DCM (20 mL) was added, and water (20 mL) was added. The reaction was extracted and the organic layer was evaporated off solvent, afforted residue (10 mg) was purified, providing compound 1. LC-MS (M+1): 563.

$^1$H NMR (400 MHz, Methanol-d4) δ 9.22 (d, J=0.7 Hz, 1H), 8.31 (s, 1H), 8.01 (d, J=0.6 Hz, 1H), 7.96 (d, J=7.7 Hz, 1H), 7.89 (dd, J=7.7, 1.0 Hz, 1H), 7.80 (dd, J=7.8, 1.0 Hz, 1H), 4.57-4.44 (m, 1H), 4.38-4.17 (m, 4H), 3.52-3.35 (m, 2H), 3.02 (s, 2H), 2.29-1.91 (m, 6H), 1.89-1.70 (m, 4H), 1.63 (q, J=6.5 Hz, 2H), 1.51 (s, 9H).

Example 2 16-(piperidin-4-yl)-4,5,12,15,16,19,25-heptaazatetracyclo[19.3.1.1²,⁵.0¹⁴,¹⁸]hexacosa-1(24),2(26),3,14,17,21(25),22-heptaene-13,20-dione (16)

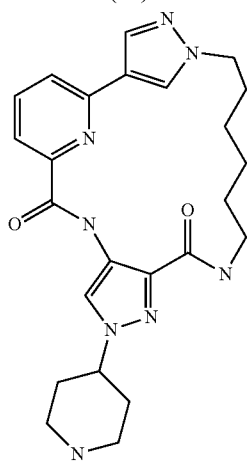

The compound from example 1 (0.72 mmol) was dissolved in methanol (2 mL), and to it was added hydrogen chloride (1.80 mL; 7.20 mmol; 10.00 eq.). The reaction was stirred at RT for 3 hr until completed. The solvent was removed and the residue was dissolved in DMSO, which was then purified by prep HPLC, affording the desired compound (80 mg, yield 24%). LC-MS (M+1): 463.
Scheme 2:
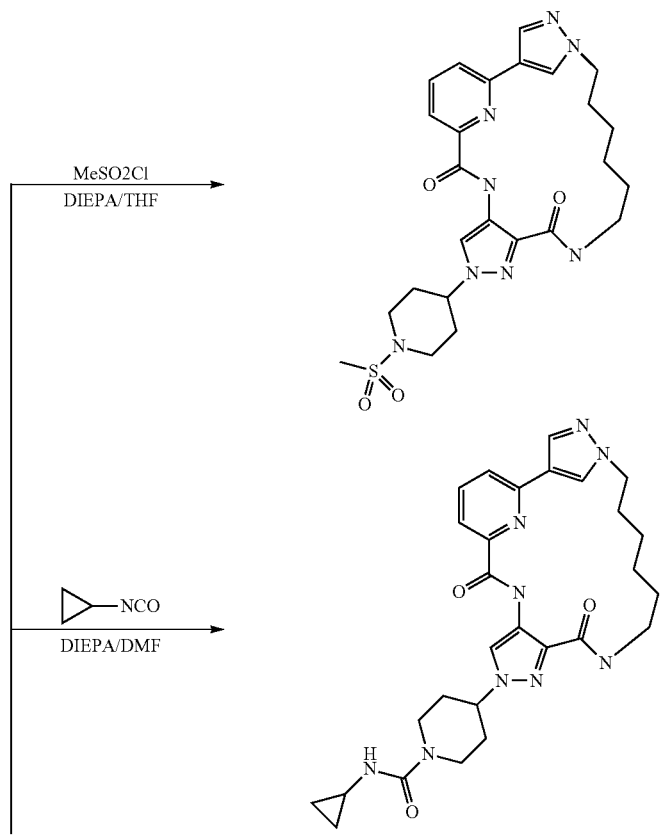

53 54
-continued
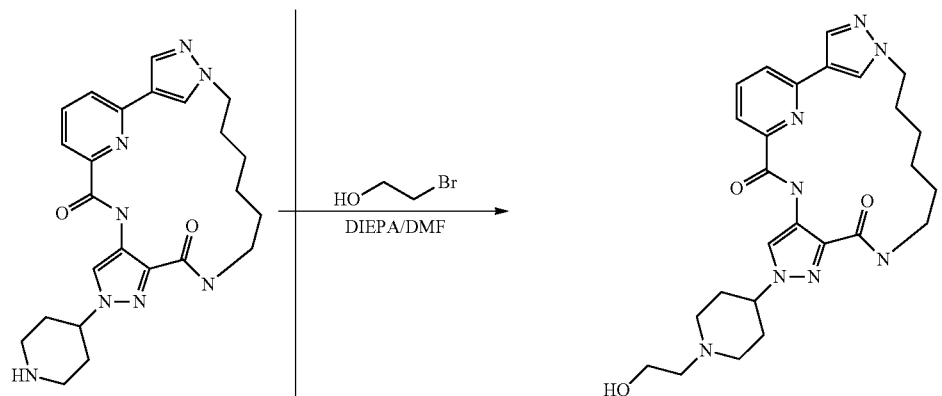
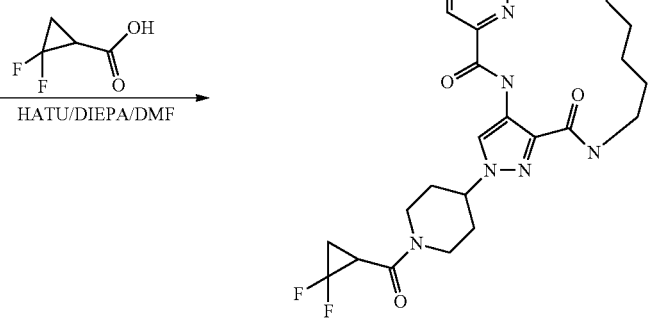
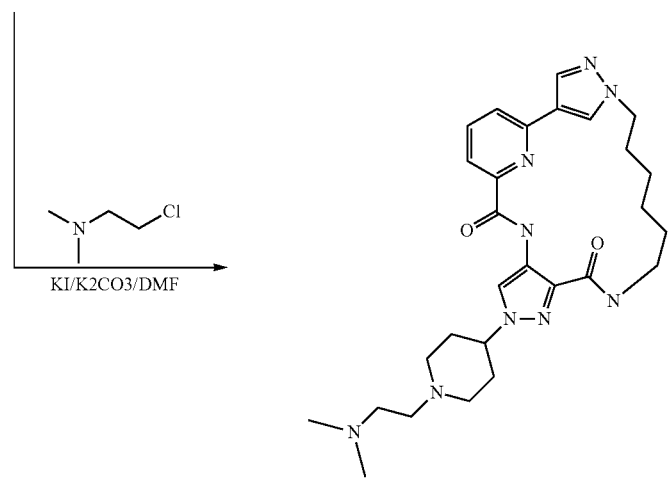

Example 3 6-(1-methanesulfonylpiperidin-4-yl)-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (17)

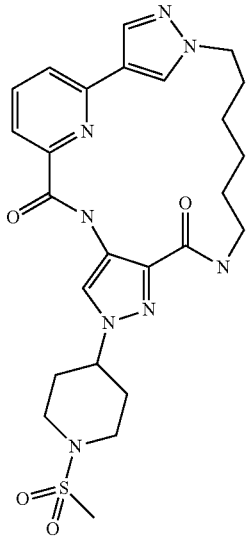 [SMILES: CS(=O)(=O)N1CCC(n2cc3c(n2)C(=O)NCCCCCCn2cc(cn2)-c2cccc(n2)C(=O)N3)CC1]

A solution of 16-(piperidin-4-yl)-4,5,12,15,16,19,25-Heptaazatetracyclo[19.3.1.1$^{2,5}$.0$^{14,18}$]hexacosa-1(24),2(26),3,14,17,21(25),22-heptaene-13,20-dione (example 2, 8.00 mg; 0.02 mmol; 1.00 eq.) was dissolved in THF (0.5 mL) and to it were added Ethyl-diisopropyl-amine (0.01 mL; 0.04 mmol; 2.50 eq.) and Methanesulfonyl chloride (2.58 mg; 0.02 mmol; 1.30 eq.). The mixture was stirred at RT for 30 min until complete as indicated by LC-MS. The solvent was evaporated and the residue purified by HPLC (20-60% acetonitrile and water contained 0.1% ammonia), providing 5 mg of a white solid. LC-MS (M+1): 541.

$^1$H NMR (400 MHz, DMSO-d6) δ 12.78 (s, 1H), 9.13 (s, 1H), 8.70-8.62 (m, 1H), 8.38 (s, 1H), 8.12-7.98 (m, 2H), 7.89 (d, J=7.9 Hz, 1H), 7.80 (dd, J=20.8, 7.8 Hz, 1H), 4.47 (t, J=11.2 Hz, 1H), 4.21 (t, J=7.2 Hz, 2H), 3.72 (d, J=11.9 Hz, 2H), 3.10 (m, 2H), 2.95 (s, 3H), 2.14 (m, 6H), 1.75-1.63 (m, 4H), 1.50 (t, J=7.2 Hz, 2H), 1.26 (s, 2H).

Example 4 16-[1-(2,2-difluorocyclopropanecarbonyl)piperidin-4-yl]-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (18)

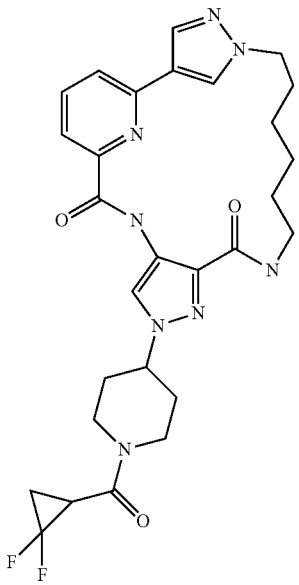 [SMILES: O=C1Nc2cn(C3CCN(C(=O)C4CC4(F)F)CC3)nc2C(=O)NCCCCCCn2cc(cn2)-c2cccc1n2]

To a solution of 2,2-Difluoro-cyclopropanecarboxylic acid (8.97 mg; 0.07 mmol; 2.00 eq.) in DMF (0.5 mL) was added HATU (17.47 mg; 0.05 mmol; 1.25 eq.), and stirred at RT for 10 min. Ethyl-diisopropyl-amine (0.01 mL; 0.06 mmol; 1.50 eq.) and 16-(piperidin-4-yl)-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (example 2, 17 mg; 0.04 mmol; 1.00 eq.) were added, and the mixture was stirred for another 1 hr. LC-MS indicated the reaction was completed, and the product was purified by prep HPLC (9 mg, yield 50%). LC-MS (M+1): 567.

$^1$H NMR (400 MHz, DMSO-d6) δ 12.83-12.65 (m, 1H), 9.13 (s, 1H), 8.65 (dt, J=13.2, 6.3 Hz, 1H), 8.41-8.28 (m, 1H), 8.13-7.95 (m, 2H), 7.95-7.71 (m, 2H), 4.63 (s, 1H), 4.48 (d, J=13.4 Hz, 1H), 4.21 (t, J=7.5 Hz, 3H), 3.25-3.5 (m, 4H), 2.91 (q, J=12.7 Hz, 1H), 2.13 (d, J=9.7 Hz, 3H), 2.01-1.75 (m, 4H), 1.68 (s, 4H), 1.55-1.41 (m, 2H).

Example 5 N-cyclopropyl-4-{13,20-dioxo-4,5,12,15,16,19,25-heptaazatetracyclo[19.3.1.1$^{2,5}$.0$^{14,18}$]hexacosa-1(24),2(26),3,14,17,21(25),22-heptaen-16-yl}piperidine-1-carboxamide (19)

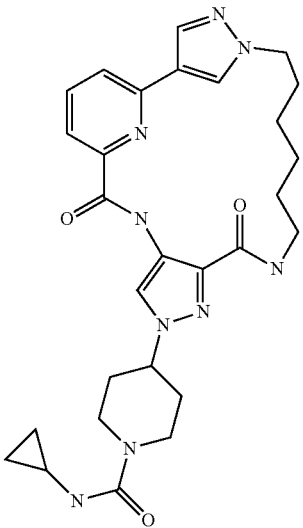 [SMILES: O=C1Nc2cn(C3CCN(C(=O)NC4CC4)CC3)nc2C(=O)NCCCCCCn2cc(cn2)-c2cccc1n2]

A mixture of 16-(piperidin-4-yl)-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (example 2, 17. mg; 0.04 mmol; 1.00 eq.), Ethyl-diisopropyl-amine (0.01 mL; 0.06 mmol; 1.50 eq.) and Isocyanato-cyclopropane (6. mg; 0.07 mmol; 2.00 eq.) in DMF (0.5 mL) was stirred at RT for 1 hr. After completion (by LC-MS), the reaction was purified by prep HPLC, providing 11 mg (white solid) of the title compound (yield 54%). LC-MS (M+1): 546.

$^1$H NMR (400 MHz, DMSO-d6) δ 12.77 (s, 1H), 9.13 (s, 1H), 8.63 (d, J=6.2 Hz, 1H), 8.33 (s, 1H), 8.09 (s, 1H), 8.02 (t, J=7.7 Hz, 1H), 7.92-7.75 (m, 2H), 6.64 (s, 1H), 4.48 (t, J=11.5 Hz, 1H), 4.21 (t, J=7.2 Hz, 2H), 4.14-3.97 (m, 3H), 2.82 (t, J=12.6 Hz, 2H), 2.22-2.01 (m, 4H), 1.98 (s, 1H), 1.91-1.76 (m, 2H), 1.69 (q, J=7.5 Hz, 4H), 1.56-1.37 (m, 2H), 0.68-0.45 (m, 2H), 0.40 (d, J=3.2 Hz, 2H).

Example 6 6-{1-[2-(dimethylamino)ethyl]piperidin-4-yl}-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (23)

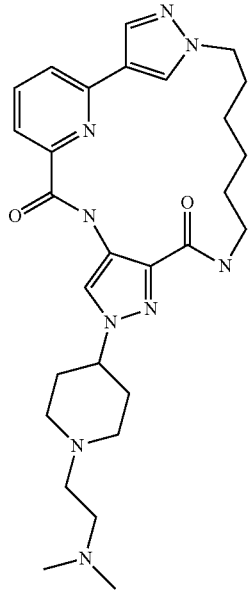 [SMILES: CN(C)CCN1CCC(n2cc3c(n2)C(=O)NCCCCCCn2cc(cn2)-c2cccc(n2)C(=O)N3)CC1]

A mixture of 16-(piperidin-4-yl)-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (example 2, 11.00 mg; 0.02 mmol; 1.00 eq.), Ethyl-diisopropyl-amine (0.02 mL; 0.10 mmol; 4.00 eq.), (2-Chloro-ethyl)-dimethyl-amine hydrochloride (2) (8.59 mg; 0.05 mmol; 2.00 eq.), and potassium iodide in DMF (0.5 mL) was stirred at 100° C. for 24 hr. The mixture was purified by prep HPLC, providing the title compound as a white solid (3 mg). LC-MS (M+1): 534.

$^1$H NMR (400 MHz, Methanol-d4) δ 9.23 (s, 1H), 8.30 (d, J=1.6 Hz, 1H), 8.07-7.92 (m, 2H), 7.81 (d, J=7.7 Hz, 1H), 4.28 (t, J=7.3 Hz, 3H), 3.44 (t, J=7.7 Hz, 3H), 3.13 (d, J=12.4 Hz, 3H), 2.61 (s, 4H), 2.40-2.08 (m, 14H), 1.81 (q, J=7.6 Hz, 5H), 1.65 (q, J=7.0 Hz, 2H).

Example 7 16-[1-(2-hydroxyethyl)piperidin-4-yl]-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (22)

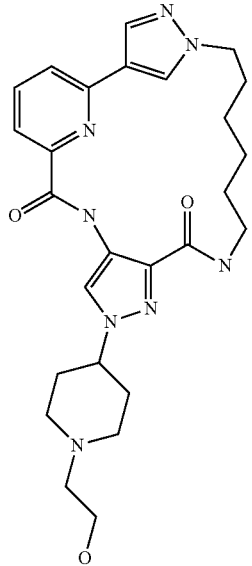 [SMILES: O=C1Nc2cn(C3CCN(CCO)CC3)nc2C(=O)NCCCCCCn2cc(cn2)-c2cccc1n2]

A mixture of 16-(piperidin-4-yl)-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (example 2, 8.00 mg; 0.02 mmol; 1.00 eq.), Ethyl-diisopropyl-amine (0.01 mL; 0.04 mmol; 2.20 eq.), and 2-Bromo-ethanol (2.81 mg; 0.02 mmol; 1.30 eq.) in DMF (0.5 mL) was stirred at RT for 1 hr, then 60° C. for another 5 hr. The reaction was purified by prep HPLC, providing the title compound as a white solid (5 mg). LC-MS (M+1): 507.

$^1$H NMR (500 MHz, Methanol-d4) δ 9.19 (d, J=1.8 Hz, 1H), 8.27 (d, J=2.2 Hz, 1H), 8.06-7.89 (m, 2H), 7.86 (dd, J=7.8, 2.3 Hz, 1H), 7.77 (dd, J=7.8, 2.3 Hz, 1H), 4.58 (s, 1H), 4.34-4.18 (m, 3H), 3.74 (t, J=6.1 Hz, 2H), 3.40 (t, J=7.6 Hz, 2H), 3.18 (d, J=11.4 Hz, 2H), 2.67 (d, J=5.8 Hz, 2H), 2.38 (t, J=11.8 Hz, 2H), 2.18 (td, J=15.0, 14.5, 9.8 Hz, 6H), 1.79 (p, J=7.4 Hz, 4H), 1.62 (q, J=6.8 Hz, 2H).

Scheme 3

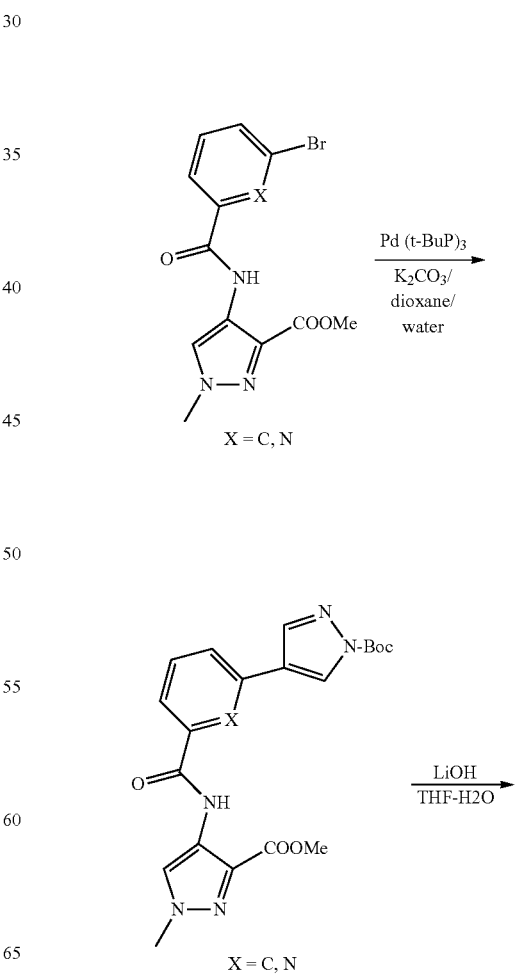

59

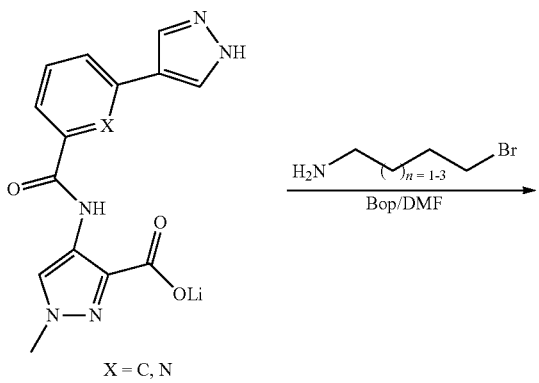

X = C, N

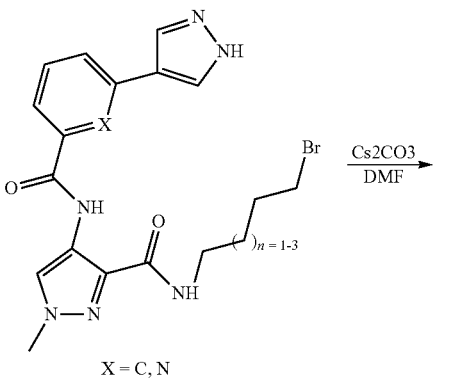

X = C, N

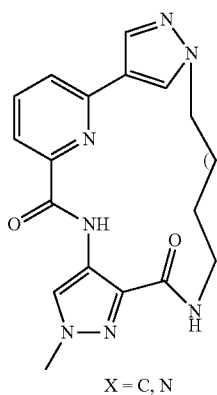

X = C, N

Intermediates

4-[(6-Bromo-pyridine-2-carbonyl)-amino]-1-methyl-
1H-pyrazole-3-carboxylic acid methyl ester

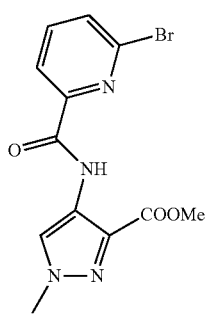 [SMILES: COC(=O)c1nn(C)cc1NC(=O)c1cccc(Br)n1]

A mixture of 6-Bromo-pyridine-2-carboxylic acid (3000. mg; 14.85 mmol; 1.00 eq.), 4-Amino-1-methyl-1H-pyrazole-3-carboxylic acid methyl ester (2765. mg; 17.82 mmol;

60

1.20 eq.), Ethyl-diisopropyl-amine (6.57 mL; 37.13 mmol; 2.50 eq.) and 3-[chloro-(2-oxooxazolidin-3-yl)phosphoryl]oxazolidin-2-one (4536 mg; 17.82 mmol; 1.20 eq.) in DCM (20 mL) were stirred at RT for overnight. The reaction was filtered, the solid was washed with water, and then acetonitile, the title compound was obtained as a white solid. The filtrate was washed with water, the organic layer was separated, concentrated, washed with methanol, and collected the title compound (combined portions: gave product 5000 mg, which was quantitative yield). LC-MS (M+1): 339/341.

4-{[6-(1-tert-Butoxycarbonyl-1H-pyrazol-4-yl)-pyridine-2-carbonyl]-amino}-1-methyl-1H-pyrazole-3-carboxylic acid methyl ester

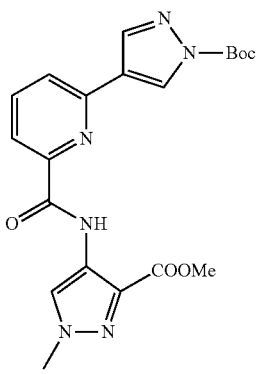 [SMILES: COC(=O)c1nn(C)cc1NC(=O)c1cccc(-c2cnn(C(=O)OC(C)(C)C)c2)n1]

A reaction mixture of 4-{[6-(1-tert-Butoxycarbonyl-1H-pyrazol-4-yl)-pyridine-2-carbonyl]-amino}-1-methyl-1H-pyrazole-3-carboxylic acid methyl ester (5000 mg; 13.37 mmol), 4-(4,4,5,5-Tetramethyl-[1,3,2]dioxaborolan-2-yl)-pyrazole-1-carboxylic acid tert-butyl ester (4770 mg; 16.22 mmol; 1.10 eq.), dipotassium carbonate (2241 mg; 16.22 mmol; 1.10 eq.), 100 mL of dioxane and 10 mL of water was degassed. To it was added palladium; tritert-butylphosphane (376 mg; 0.74 mmol; 0.05 eq.), and the reaction was stirred at 35° C. overnight. The reaction was diluted with EA (100 mL), washed with brine, dried, and concentrated, white solid that precipitated out, filtered, to provide the title compound (5700 mg, yield 90%). LC-MS (M+1): 427.

Lithium 1-methyl-4-{[6-(1H-pyrazol-4-yl)-pyridine-2-carbonyl]-amino}-1H-pyrazole-3-carboxylate

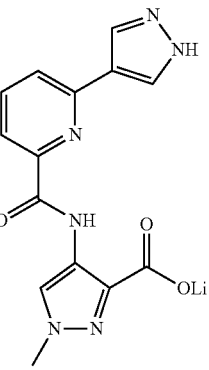

A mixture of 4-{[6-(1-tert-Butoxycarbonyl-1H-pyrazol-4-yl)-pyridine-2-carbonyl]-amino}-1-methyl-1H-pyrazole-3-carboxylic acid methyl ester (2300 mg; 5.39 mmol; 1.00 eq.), lithium hydroxide hydrate (679. mg; 16.18 mmol; 3.00 eq.) in THF (13 mL) and water (13 mL) was stirred at RT overnight. The reaction was filtered and 1200 mg of the title compound was collected (yield 71%). LC-MS (M+1): 313.

6-(1H-Pyrazol-4-yl)-pyridine-2-carboxylic acid [3-(6-bromo-hexylcarbamoyl)-1-methyl-1H-pyrazol-4-yl]-amide

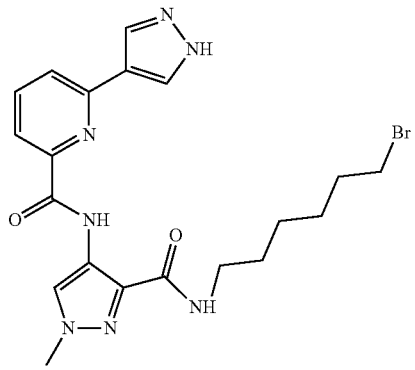 [SMILES: Cn1cc(NC(=O)c2cccc(-c3cn[nH]c3)n2)c(C(=O)NCCCCCCBr)n1]

A mixture of lithium 1-methyl-4-{[6-(1H-pyrazol-4-yl)-pyridine-2-carbonyl]-amino}-1H-pyrazole-3-carboxylate (100 mg; 0.31 mmol; 1.00 eq.), BOP (172 mg; 0.38 mmol; 1.20 eq.) and Ethyl-diisopropyl-amine (0.16 mL; 0.94 mmol; 3.00 eq.) in DMF (2 mL), was stirred at RT for 10 min, cooled to 0° C., and 6-Bromo-hexylamine hydrochloride (2) (80 mg; 0.31 mmol; 1.00 eq.) was added. The reaction was stirred for 3 hr at 0° C., quenched with water, and filtered, to provide 80 mg of crude product, which was dried and used directly for the next step. LC-MS (M+1): 475/477.

Example 8 16-methyl-4,5,12,15,16,19,25-heptaaza-tetracyclo[19.3.1.1$^{2,5}$.0$^{14,18}$]hexacosa-1(24),2(26),3,14,17,21(25),22-heptaene-13,20-dione (3)

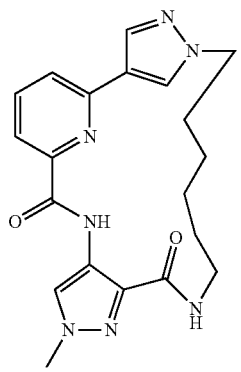 [SMILES: Cn1cc2c(n1)C(=O)NCCCCCCn1cc(cn1)-c1cccc(n1)C(=O)N2]

A mixture of 6-(1H-Pyrazol-4-yl)-pyridine-2-carboxylic acid [3-(6-bromo-hexylcarbamoyl)-1-methyl-1H-pyrazol-4-yl]-amide (80 mg; 0.17 mmol; 1.00 eq.) and Cs$_2$CO$_3$ (82.42 mg; 0.25 mmol; 1.50 eq.) in DMA (10 mL), was stirred at 70° C. for 1 hr. The solvent was removed and the residue was purified by prep HPLC, providing the title compound. LC-MS (M+1): 394.

$^1$H NMR (400 MHz, DMSO-d6) δ 12.78 (s, 1H), 9.21-9.03 (m, 1H), 8.72 (t, J=6.0 Hz, 1H), 8.31 (s, 1H), 8.11-7.96 (m, 2H), 7.85 (m, 2H), 4.20 (t, J=7.1 Hz, 2H), 3.95 (s, 3H), 2.12 (m, 2H), 1.67 (m, 5H), 1.50 (m, 2H).

Example 9 15-methyl-4,5,11,14,15,18,24-heptaaza-tetracyclo[18.3.1.1$^{2,5}$.0$^{13,17}$]pentacosa-1(23),2(25),3,13,16,20(24),21-heptaene-12,19-dione (2)

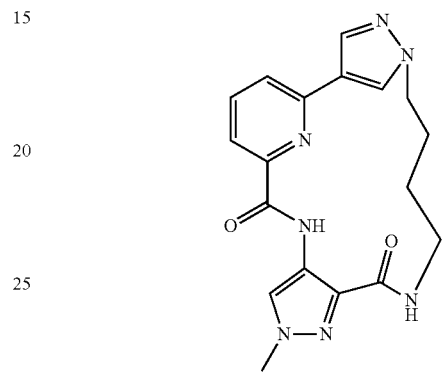

A mixture of 6-(1H-Pyrazol-4-yl)-pyridine-2-carboxylic acid [3-(5-bromo-pentylcarbamoyl)-1-methyl-1H-pyrazol-4-yl]-amide (73 mg; 0.16 mmol; 1.00 eq.), sodium hydride (13 mg; 0.32 mmol; 2.00 eq.) in DMA (5 mL) was stirred at 60° C. for 1 hr. The solvent was removed and the residue was purified by prep HPLC, providing the title compound. LC-MS (M+1): 380.

$^1$H NMR (400 MHz, Methanol-d4) δ 9.57 (s, 1H), 8.48 (s, 1H), 8.17 (s, 1H), 7.99-8.01 (m, 2H), 7.92 (m, 2H), 4.42-4.51 (m, 2H), 4.0 (s, 3H), 3.50 (m, 2H), 2.44 (m, 2H), 1.98-2.0 (m, 2H), 1.75-1.80 (m, 2H).

Example 10 4-methyl-4,5,10,13,14,17,23-heptaaza-tetracyclo[17.3.1.1$^{2,5}$.0$^{12,16}$]tetracosa-1(22),2(24),3,12,15,19(23),20-heptaene-11,18-dione (4)

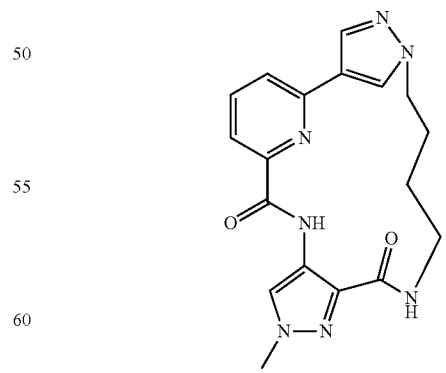

A mixture of 6-(1H-Pyrazol-4-yl)-pyridine-2-carboxylic acid [3-(4-chloro-butylcarbamoyl)-1-methyl-1H-pyrazol-4-yl]-amide (90.00 mg; 0.22 mmol; 1.00 eq.) and cesium (1+) carbonic acid (0.5) (109.46 mg; 0.34 mmol; 1.50 eq.) in DMA (10 mL), was stirred at 70° C. for 1 hr. The mixture was purified by prep HPLC, providing the title compound. LC-MS (M+1): 366.

¹H NMR (400 MHz, DMSO-d6) δ 13.20 (s, 1H), 12.36 (s, 1H), 8.57 (s, 2H), 8.44 (s, 2H), 8.06-7.97 (m, 1H), 7.95 (dd, J=7.9, 1.2 Hz, 1H), 7.89 (dd, J=7.4, 1.1 Hz, 1H), 4.00 (d, J=6.7 Hz, 2H), 3.97 (s, 3H), 3.65 (t, J=6.8 Hz, 2H), 1.97 (m, 2H), 1.92-1.80 (m, 2H).

Example 11 16-methyl-4,5,12,15,16,19-hexaazatetracyclo[19.3.1.1$^{2,5}$.0$^{1'',1'''}$]hexacosa-1(24),2(26),3,14,17,21(25),22-heptaene-13,20-dione (1)

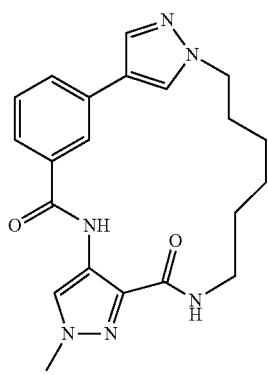 [SMILES: Cn1cc2c(n1)C(=O)NCCCCCCn1cc(cn1)-c1cccc(c1)C(=O)N2]

1-Methyl-4-[3-(1H-pyrazol-4-yl)-benzoylamino]-1H-pyrazole-3-carboxylic acid (6-bromo-hexyl)-amide (20.00 mg; 0.04 mmol; 1.00 eq.), Ethyl-diisopropyl-amine (0.01 mL; 0.08 mmol; 2.00 eq.) and DMA (3 mL) were charged in 10 mL microwave tube, and the reaction was placed in a microwave at 100° C. for 20 min. The reaction was purified by prep HPLC, providing the title compound. LC-MS (M+1): 393.

¹H NMR (400 MHz, Methanol-d4) δ 11.58 (s, 1H), 8.24 (d, J=5.9 Hz, 2H), 8.07 (s, 1H), 7.88-7.70 (m, 3H), 7.57 (t, J=7.7 Hz, 1H), 4.37-4.26 (m, 2H), 3.97 (s, 3H), 3.50-3.36 (m, 2H), 1.94 (m, 2H), 1.75 (q, J=6.9 Hz, 2H), 1.60 (m, 4H).

Scheme 4

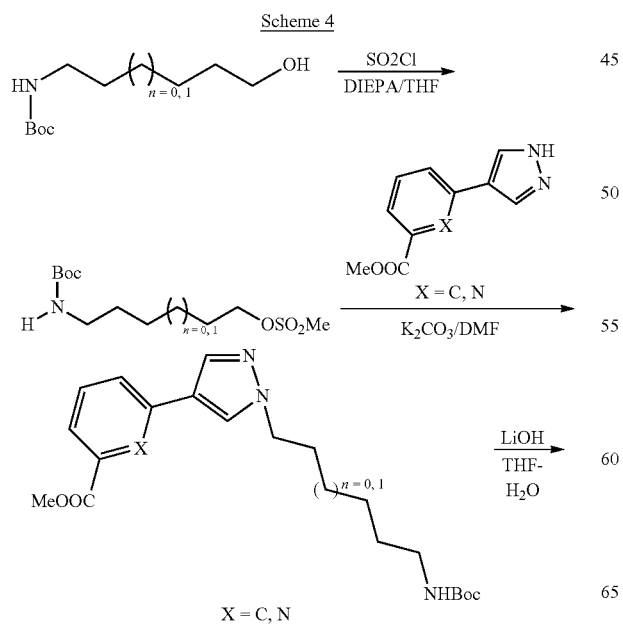

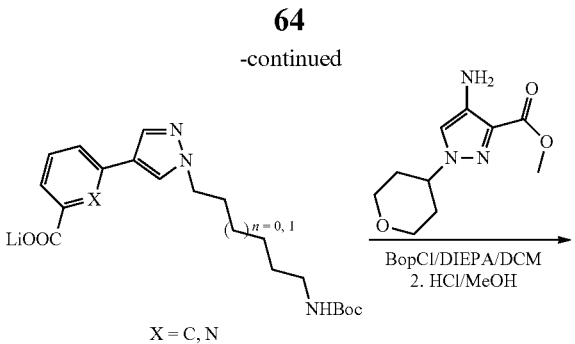

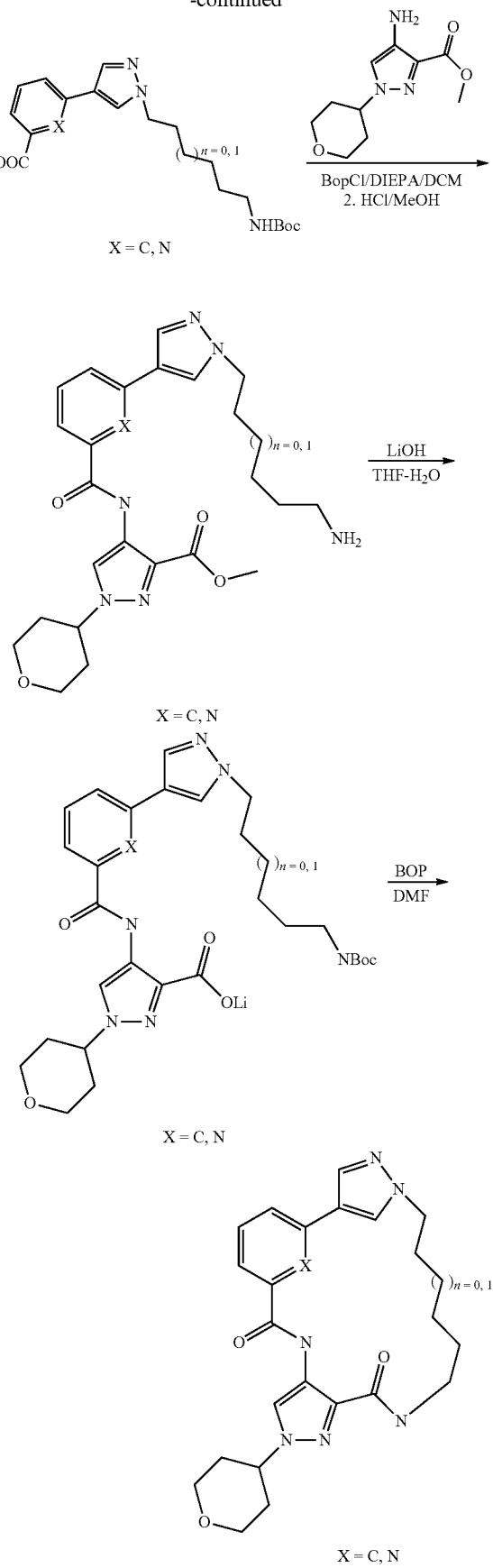

Intermediates

Methanesulfonic acid
6-tert-butoxycarbonylamino-hexyl ester

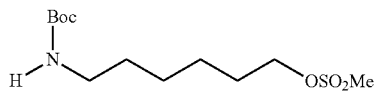

To a stirring solution of (6-Hydroxy-hexyl)-carbamic acid tert-butyl ester (5000 mg; 23 mmol; 1.00 eq.) in THF (60 mL) and Ethyl-diisopropyl-amine (5.63 mL; 32.21 mmol; 1.40 eq.) was added drop wise Methanesulfonyl chloride (2.23 mL; 28.76 mmol; 1.25 eq.) at 0° C. The reaction was stirred for 30 min at 0° C., then raised to RT for 1 h. EA (100 mL) was added, the organic layer was washed with brine, dried, and concentrated to provide a yellow solid (quantitative yield), which was directly used for the next step reaction. LC-MS (M+1): 296.

6-[1-(6-tert-Butoxycarbonylamino-hexyl)-1H-pyrazol-4-yl]-pyridine-2-carboxylic acid methyl

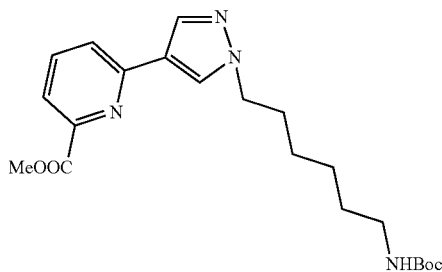 [SMILES: COC(=O)c1cccc(-c2cnn(CCCCCCNC(=O)OC(C)(C)C)c2)n1]

A mixture of 6-(1H-Pyrazol-4-yl)-pyridine-2-carboxylic acid methyl ester (1210 mg; 5.95 mmol; 1.00 eq.) in DMF (10 mL) was cooled to 0° C., and to it was added sodium hydride (476 mg; 11.91 mmol; 2.00 eq.). The reaction was stirred for 30 min, then Methanesulfonic acid 6-tert-butoxycarbonylamino-hexyl ester (2287 mg; 7.74 mmol; 1.30 eq.) was added. The mixture was stirred at RT for 3 hr, the solvent was removed and the residue was extracted with EA (30 mL×3). The organic layer was washed with brine, the solvent was removed, and the residue was purified by SNAP column to afford the title compound (480 mg, yield 20%). LC-MS (M+1): 403.

Lithium 6-[1-(6-tert-Butoxycarbonylamino-hexyl)-1H-pyrazol-4-yl]-pyridine-2-carboxylate

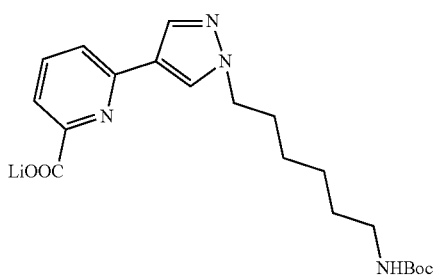

A mixture of 6-[1-(6-tert-Butoxycarbonylamino-hexyl)-1H-pyrazol-4-yl]-pyridine-2-carboxylic acid methyl ester (347 mg; 0.86 mmol; 1.00 eq.), lithium hydroxide hydrate (72 mg; 1.72 mmol; 2.00 eq.) in THF (2 mL), and water (2 mL) was stirred at RT for 2 hr. The solvent was removed, provided a white solid as desired, which was directly used for the next. LC-MS (M+1): 389.

4-({6-[1-(6-Amino-hexyl)-1H-pyrazol-4-yl]-pyridine-2-carbonyl}-amino)-1-(tetrahydro-pyran-4-yl)-1H-pyrazole-3-carboxylic acid methyl ester

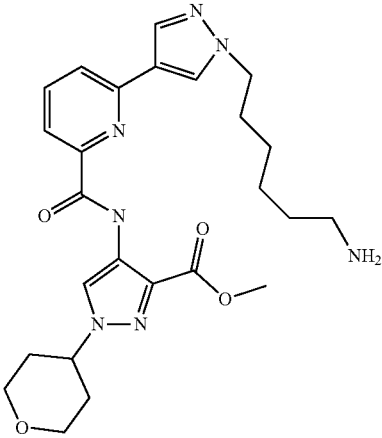 [SMILES: COC(=O)c1nn(C2CCOCC2)cc1NC(=O)c1cccc(-c2cnn(CCCCCCN)c2)n1]

To a stirred mixture of lithium 6-[1-(6-tert-Butoxycarbonylamino-hexyl)-1H-pyrazol-4-yl]-pyridine-2-carboxylate (172 mg; 0.44 mmol; 1.00 eq.), 3-[chloro-(2-oxooxazolidin-3-yl)phosphoryl]oxazolidin-2-one (133 mg; 0.52 mmol; 1.20 eq.) in DMF (3 mL), was added Ethyl-diisopropyl-amine (0.16 mL; 0.92 mmol; 2.10 eq.). The reaction was stirred for 30 min and then 4-Amino-1-(tetrahydro-pyran-4-yl)-1H-pyrazole-3-carboxylic acid methyl ester (108 mg; 0.48 mmol; 1.10 eq.) was added. Stirring was continued overnight at RT, diluted with water (20 mL), extracted with DCM (40 mL×2), and the organic layer was washed with brine. The solvent was removed, got residue, provided 4-({6-[1-(6-tert-Butoxycarbonylamino-hexyl)-1H-pyrazol-4-yl]-pyridine-2-carbonyl}-amino)-1-(tetrahydro-pyran-4-yl)-1H-pyrazole-3-carboxylic acid methyl ester (100 mg, yield 38.5%). LC-MS (M+1): 596. To the above product added methanol (1 mL), then hydrogen chloride (0.65 mL; 2.62 mmol; 6.00 eq.), the reaction mixture was stirred at RT for overnight. The solvent was removed, and the residue was purified by prep HPLC (basic) (20-70% water in acetonitrile), providing the title compound (65 mg, yield 27.8%). LC-MS (M+1): 496.

Lithium 4-({6-[1-(6-Amino-hexyl)-1H-pyrazol-4-yl]-pyridine-2-carbonyl}-amino)-1-(tetrahydro-pyran-4-yl)-1H-pyrazole-3-carboxylate

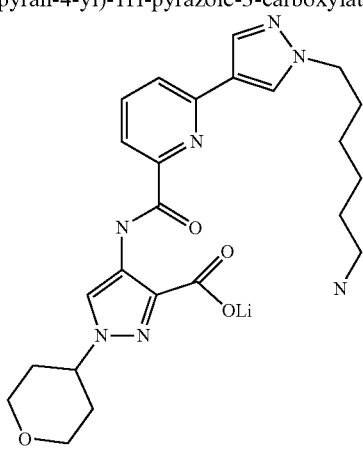

A mixture of 4-({6-[1-(6-Amino-hexyl)-1H-pyrazol-4-yl]-pyridine-2-carbonyl}-amino)-1-(tetrahydro-pyran-4-yl)-1H-pyrazole-3-carboxylic acid methyl ester (65 mg; 0.13 mmol; 1.00 eq.), lithium hydroxide hydrate (11 mg; 0.26 mmol; 2.00 eq.) in THF (2 mL) and water (2 mL) was stirred at RT for 1 hr. The solvent was removed providing an off-white solid as desired, which was directly used for the next step reaction. LC-MS (M+1): 482.

Example 12 16-(oxan-4-yl)-4,5,12,15,16,19,25-heptaazatetracyclo[19.3.1.1²,⁵.0¹⁴,¹⁸]hexacosa-1(24),2(26),3,14,17,21(25),22-heptaene-13,20-dione (12)

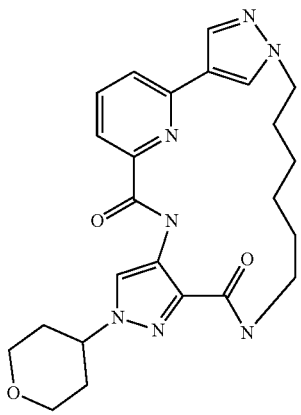 [SMILES: O=C1Nc2cn(C3CCOCC3)nc2C(=O)NCCCCCCn2cc(cn2)-c2cccc1n2]

A mixture of lithium 4-({6-[1-(6-Amino-hexyl)-1H-pyrazol-4-yl]-pyridine-2-carbonyl}-amino)-1-(tetrahydro-pyran-4-yl)-1H-pyrazole-3-carboxylate (60 mg; 0.12 mmol; 1.00 eq.), BOP (70 mg; 0.15 mmol; 1.25 eq.) and Ethyl-diisopropyl-amine (0.04 mL; 0.25 mmol; 2.00 eq.) in DMF (8 mL), was stirred at RT for 3 hr. The reaction was purified by prep HPLC (basic), providing the title compound (12 mg). LC-MS (M+1): 464.

¹H NMR (400 MHz, DMSO-d6) δ 12.78 (s, 1H), 9.14 (s, 1H), 8.64 (t, J=5.9 Hz, 1H), 8.35 (s, 1H), 8.09 (s, 1H), 8.02 (t, J=7.7 Hz, 1H), 7.89-7.74 (m, 2H), 4.65-4.47 (m, 1H), 4.21 (t, J=7.1 Hz, 2H), 4.07-3.88 (m, 3H), 3.54-3.41 (m, 2H), 3.30-3.21 (2H), 2.24-1.96 (m, 5H), 1.71 (m, 4H), 1.51 (q, J=6.5 Hz, 2H).

Example 13: 15-(oxan-4-yl)-4,5,11,14,15,18-hexaazatetracyclo[18.3.1.1²,⁵.0¹³,¹⁷]pentacosa-1(23),2(25),3,13,16,20(24),21-heptaene-12,19-dione (6)

3-[1-(5-tert-Butoxycarbonylamino-pentyl)-1H-pyrazol-4-yl]-benzoic acid methyl ester

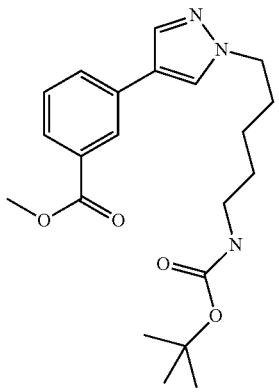 [SMILES: COC(=O)c1cccc(-c2cnn(CCCCCNC(=O)OC(C)(C)C)c2)c1]

A mixture of 3-(1H-Pyrazol-4-yl)-benzoic acid methyl ester (1000 mg; 4.95 mmol; 1.00 eq.), Methanesulfonic acid 5-tert-butoxycarbonylamino-pentyl ester (1530 mg; 5.44 mmol; 1.10 eq.), and $Cs_2CO_3$ (2416 mg; 7.42 mmol; 1.50 eq.) in DMF (10 mL) was stirred at 70° C. for 1 hr. The reaction was poured 60 mL of stirring water, a white solid precipitated out, filtered, collected 1750 mg white solid as title compound (yield 91.3%). LC-MS (M+1): 388.

Lithium 3-[1-(5-tert-Butoxycarbonylamino-pentyl)-1H-pyrazol-4-yl]-benzoate

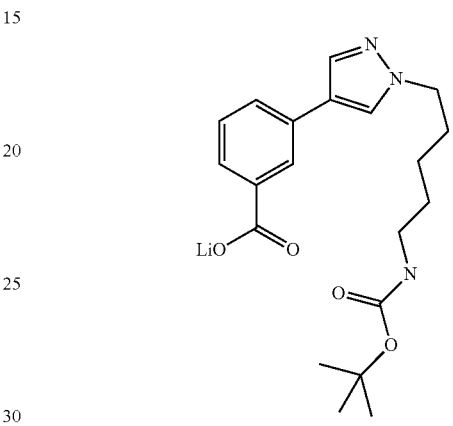

A reaction mixture of 3-[1-(5-tert-Butoxycarbonylamino-pentyl)-1H-pyrazol-4-yl]-benzoic acid methyl ester (1500 mg; 3.87 mmol; 1.00 eq.), lithium hydroxide hydrate (324 mg; 7.74 mmol; 2.00 eq.) in THF (8 mL) and water (8 mL) was stirred at RT for 2 hr, then at 40° C. for 3 hr. The mixture was added 10 mL water and 10 mL EA. Separated off organic layer, aqueous layer was evaporated off solvent, got residue, dried to provide the title compound which was directly used for the next step reaction. LC-MS (M+1): 374.

4-{3-[1-(5-tert-Butoxycarbonylamino-pentyl)-1H-pyrazol-4-yl]-benzoylamino}-1-(tetrahydro-pyran-4-yl)-1H-pyrazole-3-carboxylic acid methyl ester

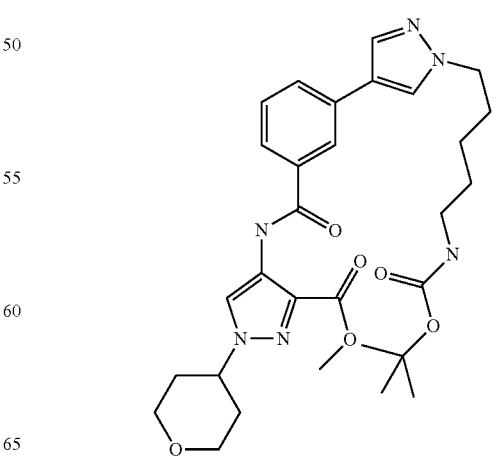

A stirred solution of 3-[1-(5-tert-Butoxycarbonylamino-pentyl)-1H-pyrazol-4-yl]-benzoic acid lithium (220.00 mg; 0.58 mmol; 1.00 eq.) and 4-Amino-1-(tetrahydro-pyran-4-yl)-1H-pyrazole-3-carboxylic acid methyl ester (156.74 mg; 0.70 mmol; 1.20 eq.) in DCM 4 ml was added Ethyl-diisopropyl-amine (0.21 ml; 1.16 mmol; 2.00 eq.), then 3-[chloro-(2-oxooxazolidin-3-yl)phosphoryl]oxazolidin-2-one (177.15 mg; 0.70 mmol; 1.20 eq.), the reaction mixture was stirred at RT for 3 h, lc-ms showed clean desired. Diluted with EA, washed with brine, sodium bicarbonate solution, brine, 10% citric acid aq, then brine, dried over MgSO$_4$ and concentrated to give the desired product. 4-{3-[1-(5-tert-Butoxycarbonylamino-pentyl)-1H-pyrazol-4-yl]-benzoylamino}-1-(tetrahydro-pyran-4-yl)-1H-pyrazole-3-carboxylic acid methyl ester. LC-MS (M+1): 581.

pyrazol-4-yl]-benzoylamino}-1-(tetrahydro-pyran-4-yl)-1H-pyrazole-3-carboxylic acid methyl ester. LC-MS (M+1): 481.

A mixture of 4-{3-[1-(5-Amino-pentyl)-1H-pyrazol-4-yl]-benzoylamino}-1-(tetrahydro-pyran-4-yl)-1H-pyrazole-3-carboxylic acid methyl ester (100.00 mg; 0.21 mmol; 1.00 eq.), lithium hydroxide hydrate (17.46 mg; 0.42 mmol; 2.00 eq.) in 1 ml THF and 1 ml water was stirred at 40° C. for 2 hr, reaction was completed. Removed off solvent, got white solid as title compound. LC-MS (M+1): 467.

15-(oxan-4-yl)-4,5,11,14,15,18-hexaazatetracyclo [18.3.1.1$^{2,5}$.0$^{13,17}$]pentacosa-1(23),2(25),3,13, 16,20 (24),21-heptaene-12,19-dione (6)

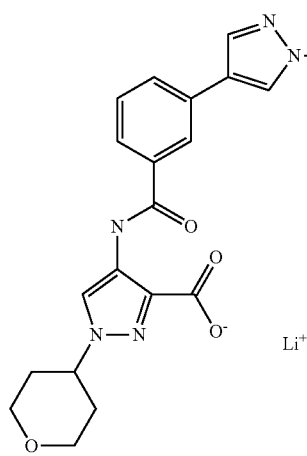

Lithium 4-{3-[1-(5-Amino-pentyl)-1H-pyrazol-4-yl]-benzoylamino}-1-(tetrahydro-pyran-4-yl)-1H-pyrazole-3-carboxylate To A solution of 4-{3-[1-(5-tert-Butoxycarbonylamino-pentyl)-1H-p 4-{3-[1-(5-Amino-pentyl)-1H-pyrazol-4-yl]-benzoylamino}-1-(tetrahydro-pyran-4-yl)-1H-pyrazole-3-carboxylic acid methyl esteryrazol-4-yl]-benzoylamino}-1-(tetrahydro-pyran-4-yl)-1H-pyrazole-3-carboxylic acid methyl ester (300.00 mg; 0.52 mmol; 1.00 eq.) in methanol 2 ml added hydrogen chloride (1.29 ml; 5.17 mmol; 10.00 eq.), stirred at RT for 3 hr, reaction was completed, purified by basic HPLC, collected 4-{3-[1-(5-Amino-pentyl)-1H-

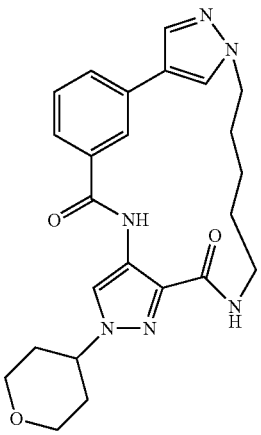 [SMILES: O=C1Nc2cn(C3CCOCC3)nc2C(=O)NCCCCCn2cc(cn2)-c2cccc1c2]

A mixture of lithium 4-{3-[1-(5-Amino-pentyl)-1H-pyrazol-4-yl]-benzoylamino}-1-(tetrahydro-pyran-4-yl)-1H-pyrazole-3-carboxylate (100 mg; 0.21 mmol; 1.00 eq.), BOP (115.81 mg; 0.25 mmol; 1.20 eq.) and Ethyl-diisopropyl-amine (0.07 mL; 0.42 mmol; 2.00 eq.) in DMF (10 mL), was stirred at 0° C. for 3 hr. The solvent was removed and the residue was purified by prep HPLC (basic, 20-70% acetonitrile in water), providing the title compound. LC-MS (M+1): 449.

1H NMR (400 MHz, DMSO-d6) δ 10.60 (s, 1H), 8.34 (s, 1H), 8.26-8.21 (m, 1H), 7.90 (m, 2H), 7.70 (d, 1H)), 7.56 (d, 1H), 7.39 (t, J=7.7 Hz, 1H), 4.55-4.50 (m, 1H), 4.24-4.20 (m, 2H), 4.02-3.90 (m, 2H), 3.53-3.48 (m, 4H), 2.04-1.98 (m, 4H), 1.87-1.80 (m, 2H), 1.58-1.50 (m, 2H), 1.26-1.24 (m, 2H).

Scheme 5

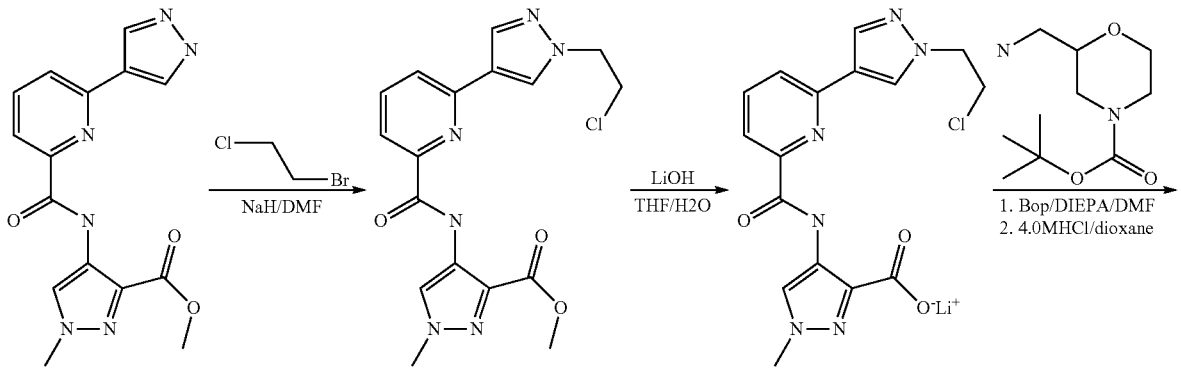

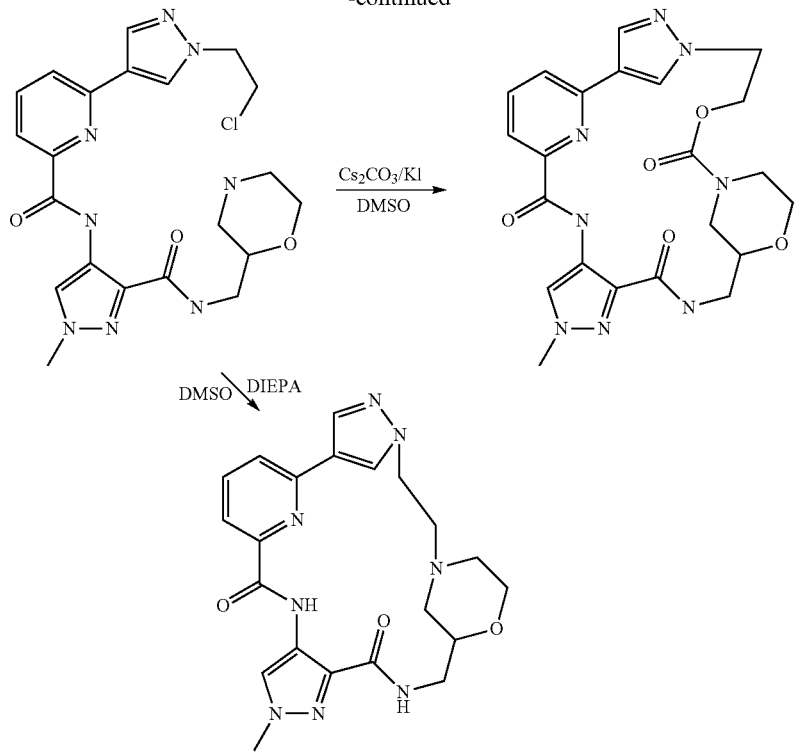

Intermediates

4-({6-[1-(2-Chloro-ethyl)-1H-pyrazol-4-yl]-pyridine-2-carbonyl}-amino)-1-methyl-1H-pyrazole-3-carboxylic acid methyl ester

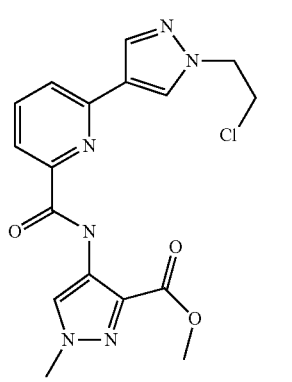 [SMILES: COC(=O)c1nn(C)cc1NC(=O)c1cccc(-c2cnn(CCCl)c2)n1]

To a solution of 1-Methyl-4-{[6-(1H-pyrazol-4-yl)-pyridine-2-carbonyl]-amino}-1H-pyrazole-3-carboxylic acid methyl ester (1200 mg; 3.68 mmol; 1.00 eq.) in DMF (15 mL) was added sodium hydride (176 mg; 7.35 mmol; 2.00 eq.). The reaction was stirred at RT for 20 min, then 1-Bromo-2-chloro-ethane (0.46 mL; 5.52 mmol; 1.50 eq.) was added, and result reaction mixture was stirred at RT overnight. The reaction was quenched with saturate ammonium chloride, then water (100 mL) was added. Solid precipitated out, filtered, collected white solid as the title compound (1200 mg, yield 84%). LC-MS (M+1): 389.

Lithium 4-({6-[1-(2-Chloro-ethyl)-1H-pyrazol-4-yl]-pyridine-2-carbonyl}-amino)-1-methyl-1H-pyrazole-3-carboxylate

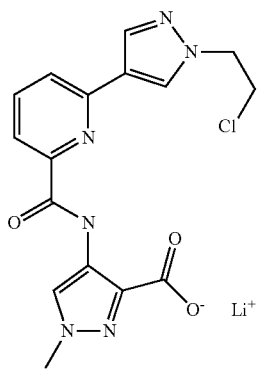 [SMILES: Cn1cc(NC(=O)c2cccc(-c3cnn(CCCl)c3)n2)c(C(=O)[O-])n1 ; [Li+]]

A mixture of 4-({6-[1-(2-Chloro-ethyl)-1H-pyrazol-4-yl]-pyridine-2-carbonyl}-amino)-1-methyl-1H-pyrazole-3-carboxylic acid methyl ester (1200 mg; 3.09 mmol; 1.00 eq.), lithium hydroxide hydrate (194 mg; 4.63 mmol; 1.50 eq.) in THF (4 mL) and water (4 mL), was stirred at 40° C. for 4 hr. The solvent was removed and the residue was dried overnight in oven, provide white solid as the title compound (quantitative yield), which was directly used for the next step. LC-MS (M+1): 375.

6-[1-(2-Chloro-ethyl)-1H-pyrazol-4-yl]-pyridine-2-carboxylic acid {1-methyl-3-[(morpholin-2-ylmethyl)-carbamoyl]-1H-pyrazol-4-yl}-amide

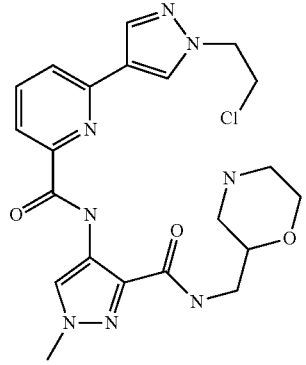 [SMILES: Cn1cc(NC(=O)c2cccc(-c3cnn(CCCl)c3)n2)c(C(=O)NCC2CNCCO2)n1]

A reaction mixture of lithium 4-({6-[1-(2-Chloro-ethyl)-1H-pyrazol-4-yl]-pyridine-2-carbonyl}-amino)-1-methyl-1H-pyrazole-3-carboxylate (150 mg; 0.39 mmol; 1.00 eq.), BOP (220 mg; 0.48 mmol; 1.22 eq.), Ethyl-diisopropyl-amine (0.14 mL; 0.79 mmol; 2.00 eq.), 2-Aminomethyl-morpholine-4-carboxylic acid tert-butyl ester (0.13 mL; 0.47 mmol; 1.20 eq.), in DMF (10 mL) was stirred at RT for 2 hr. The reaction was diluted with water, filtered, collected white off solid, which LC-MS showed desired. Above product was added hydrogen chloride (4.0M in dioxane) (0.98 mL; 3.94 mmol; 10.00 eq.) and methanol 1 mL, as result reaction mixture was stirred at RT for 2 hr. removed off solvent to provide a residue, which was dissolved in DMSO, and TEA was added to PH>=7. The compound was purified product by basic prep HPLC, providing the title compound (90 mg, yield 48%). LC-MS (M+1): 373.

Example 14 20-methyl-8,13-dioxa-4,5,10,16,19,20,23,29-octaazapentacyclo[23.3.1.1$^{2,5}$.1$^{10,14}$.0$^{18,22}$]hentriaconta-1(28),2(31),3,18,21,25(29),26-heptaene-9,17,24-trione (8)

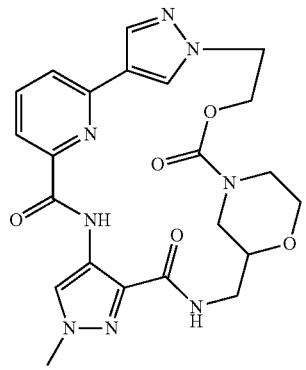 [SMILES: Cn1cc2c(n1)C(=O)NCC1CN(CCO1)C(=O)OCCn1cc(cn1)-c1cccc(n1)C(=O)N2]

A mixture of 6-[1-(2-Chloro-ethyl)-1H-pyrazol-4-yl]-pyridine-2-carboxylic acid {1-methyl-3-[(morpholin-2-ylmethyl)-carbamoyl]-1H-pyrazol-4-yl}-amide (40 mg; 0.08 mmol; 1.00 eq.), Cs$_2$CO$_3$ (33 mg; 0.10 mmol; 1.20 eq.), potassium iodide (14 mg; 0.08 mmol; 1.00 eq.) and DMSO (4 mL) was charged in sealed tube, was placed in a microwave at 110° C. for 60 min. The mixture was purified by basic prep HPLC to provide the title compound. LC-MS (M+1): 481.

1H NMR (400 MHz, DMSO-d6) δ 12.14 (s, 1H), 8.67 (s, 1H), 8.39 (d, J=5.4 Hz, 2H), 8.21 (t, J=5.9 Hz, 1H), 8.04 (t, J=7.7 Hz, 1H), 7.98-7.84 (m, 2H), 4.55 (t, J=5.6 Hz, 2H), 4.10 (m, 2H), 3.96 (s, 4H), 3.81-3.71 (m, 1H), 3.58 (td, J=9.1, 8.5, 5.5 Hz, 1H), 3.44 (td, J=10.3, 3.9 Hz, 1H), 2.84 (dd, J=12.3, 2.5 Hz, 1H), 2.65 (dd, J=9.6, 3.1 Hz, 2H), 2.43 (dd, J=12.3, 9.8 Hz, 1H).

Example 15 18-methyl-11-oxa-4,5,8,14,17,18,21,27-octaazapentacyclo[21.3.1.1$^{2,5}$.1$^{8,12}$.0$^{16,20}$]nonacosa-1(26),2(29),3,16,19,23(27),24-heptaene-15,22-dione (7)

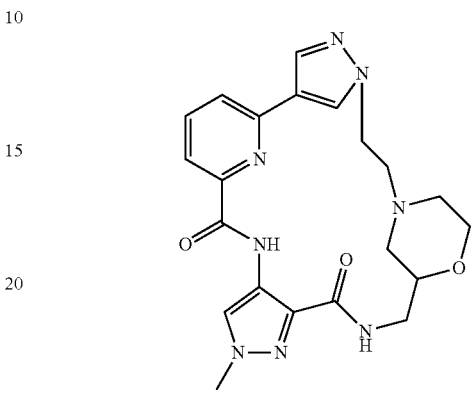

A mixture of 6-[1-(2-Chloro-ethyl)-1H-pyrazol-4-yl]-pyridine-2-carboxylic acid {1-methyl-3-[(morpholin-2-ylmethyl)-carbamoyl]-1H-pyrazol-4-yl}-amide (40.00 mg; 0.08 mmol; 1.00 eq.), Ethyl-diisopropyl-amine (0.02 mL; 0.10 mmol; 1.20 eq.) and potassium iodide (14.04 mg; 0.08 mmol; 1.00 eq.) in DMSO (4 mL) were added to a sealed tube, which was placed in a microwave at 110° C. for 60 min, still had starting material, then at 120° C. for another 60 min. The reaction was purified by HPLC, providing the title compound. LC-MS (M+1): 437.

1H NMR (400 MHz, DMSO-d6) δ 12.20 (s, 1H), 9.05 (t, J=5.3 Hz, 1H), 8.57 (s, 1H), 8.33 (s, 1H), 8.15 (d, J=0.6 Hz, 1H), 8.07-7.97 (m, 1H), 7.90 (m, 2H), 4.65 (t, J=13.1 Hz, 1H), 4.33-4.20 (m, 1H), 3.95 (s, 3H), 3.80 (d, J=11.2 Hz, 1H), 3.71 (d, J=11.0 Hz, 2H), 3.53-3.35 (m, 3H), 2.98 (m, 2H), 2.44 (d, J=13.1 Hz, 1H), 2.24-2.04 (m, 1H), 1.96-1.69 (m, 1H).

Example 16 10,17-dimethyl-8-oxa-4,5,10,13,16,17,20,26-octaazatetracyclo[20.3.1.1$^{2,5}$.0$^{15,19}$]heptacosa-1(25),2(27),3,15,18,22(26),23-heptaene-9,14,21-trione (5)

6-[1-(2-Chloro-ethyl)-1H-pyrazol-4-yl]-pyridine-2-carboxylic acid [1-methyl-3-(2-methylamino-ethyl-carbamoyl)-1H-pyrazol-4-yl]-amide

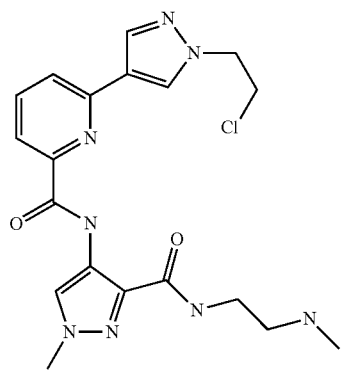 [SMILES: CNCCNC(=O)c1nn(C)cc1NC(=O)c1cccc(-c2cnn(CCCl)c2)n1]

A mixture of lithium 4-({6-[1-(2-Chloro-ethyl)-1H-pyrazol-4-yl]-pyridine-2-carbonyl}-amino)-1-methyl-1H-pyrazole-3-carboxylate (150 mg; 0.39 mmol; 1.00 eq.), BOP (220 mg; 0.47 mmol; 1.20 eq.), (2-Amino-ethyl)-methyl-carbamic acid tert-butyl ester (82 mg; 0.48 mmol; 1.22 eq.) and Ethyl-diisopropyl-amine (0.14 mL; 0.79 mmol; 2.00 eq.) in DMF (1.5 mL), was stirred at RT for 2 hr. The reaction was diluted with water, extracted with DCM, washed with brine, dried over MgSO$_4$, evaporated off solvent, provide a residue as crude (2-{[4-({6-[1-(2-Chloro-ethyl)-1H-pyrazol-4-yl]-pyridine-2-carbonyl}-amino)-1-methyl-1H-pyrazole-3-carbonyl]-amino}-ethyl)-methyl-carbamic acid tert-butyl ester. To above product added 1 mL methanol, then hydrogen chloride (4.0M in dioxane) (0.98 mL; 3.94 mmol; 10.00 eq.), the mixture was stirred at RT overnight. Filtered, collected solid, this solid was placed in 2 mL of 10% Na$_2$CO$_3$ aq, stirred at RT for 10 min. filtered again, got white solid as the title compound (55 mg, yield 32%). LC-MS (M+1): 431.

10,17-dimethyl-8-oxa-4,5,10,13,16,17,20,26-octaazatetracyclo[20.3.1.1$^{2,5}$.0$^{13,19}$]heptacosa-1(25),2(27),3,15,18,22(26),23-heptaene-9,14,21-trione (5)

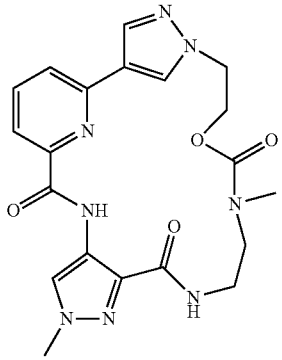 [SMILES: CN1CCNC(=O)c2nn(C)cc2NC(=O)c2cccc(n2)-c2cnn(c2)CCOC1=O]

A mixture of 6-[1-(2-Chloro-ethyl)-1H-pyrazol-4-yl]-pyridine-2-carboxylic acid [1-methyl-3-(2-methylamino-ethylcarbamoyl)-1H-pyrazol-4-yl]-amide (51 mg; 0.12 mmol; 1.00 eq.), Cs$_2$CO$_3$ (38 mg; 0.12 mmol; 1.00 eq.), potassium iodide (20 mg; 0.12 mmol; 1.00 eq.) and DMSO (5 mL) were added to a sealed tube and was placed in a microwave at 110° C. for 60 min. The reaction was purified by prep HPLC to afford the title compound. LC-MS (M+1): 439.

$^1$H NMR (400 MHz, DMSO-d6) δ 12.19 (s, 1H), 8.97 (s, 1H), 8.51 (s, 1H), 8.40 (s, 1H), 8.23 (t, J=6.0 Hz, 1H), 8.08 (t, J=7.7 Hz, 1H), 7.99-7.90 (m, 2H), 7.31 (dd, J=15.6, 8.9 Hz, 1H), 3.96 (s, 3H), 3.53-3.37 (m, 6H), 2.69 (t, J=6.4 Hz, 2H), 2.32 (s, 3H).

Example 17 8,15-dimethyl-4,5,8,11,14,15,18,24-octaazatetracyclo[18.3.1.1$^{2,5}$.0$^{13,17}$]pentacosa-1(23),2(25),3,13,16,20(24),21-heptaene-12,19-dione (10)

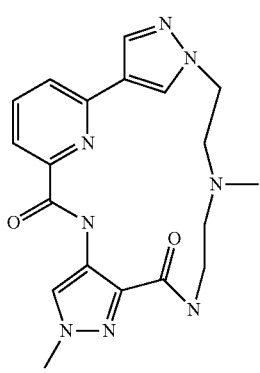 [SMILES: CN1CCNC(=O)c2nn(C)cc2NC(=O)c2cccc(n2)-c2cnn(c2)CC1]

A mixture of 6-[1-(2-Chloro-ethyl)-1H-pyrazol-4-yl]-pyridine-2-carboxylic acid [1-methyl-3-(2-methylamino-ethylcarbamoyl)-1H-pyrazol-4-yl]-amide (50 mg; 0.12 mmol; 1.00 eq.), Ethyl-diisopropyl-amine (0.03 mL; 0.17 mmol; 1.50 eq.), potassium iodide (19 mg; 0.12 mmol; 1.00 eq.) and DMSO (5 mL) were added to a sealed tube, then placed in a microwave at 125° C. for 60 min., 130° C. for another 60 min. reaction mixture was isolated by prep HPLC, providing the title compound. LC-MS (M+1): 395.

$^1$H NMR (500 MHz, DMSO-d6) δ 12.80 (s, 1H), 9.23 (s, 1H), 8.75 (t, J=5.8 Hz, 1H), 8.21 (s, 1H), 8.11 (s, 1H), 7.99 (t, J=7.8 Hz, 1H), 7.87 (d, J=7.8 Hz, 1H), 7.76 (d, J=7.6 Hz, 1H), 4.40-4.23 (m, 2H), 3.93 (s, 3H), 3.42 (q, J=5.7 Hz, 4H), 3.03 (t, J=5.1 Hz, 2H), 2.14 (s, 3H).

Example 18 8,16-dimethyl-4,5,8,12,15,16,19,25-octaazatetracyclo[19.3.1.1$^{2,5}$.0$^{14,18}$]hexacosa-1(24),2(26),3,14,17,21(25),22-heptaene-13,20-dione (11)

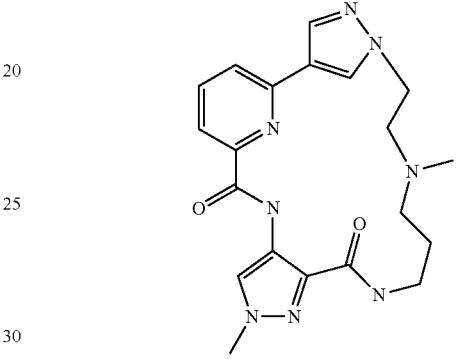

A mixture of 6-[1-(2-Chloro-ethyl)-1H-pyrazol-4-yl]-pyridine-2-carboxylic acid [1-methyl-3-(3-methylamino-propylcarbamoyl)-1H-pyrazol-4-yl]-amide (40 mg; 0.09 mmol; 1.00 eq.), Ethyl-diisopropyl-amine (0.02 mL; 0.11 mmol; 1.20 eq.), potassium iodide (15 mg; 0.09 mmol; 1.00 eq.) and DMSO (4 mL) were added to a sealed tube, then placed in a microwave at 130° C. for 60 min. The reaction mixture was isolated by HPLC, providing the title compound.

1H NMR (500 MHz, DMSO-d6) δ 12.93 (s, 1H), 9.43 (s, 1H), 8.81 (t, J=5.9 Hz, 1H), 8.27 (s, 1H), 8.10-7.93 (m, 2H), 7.83 (dd, J=35.7, 7.7 Hz, 2H), 4.43-4.17 (m, 2H), 3.94 (s, 3H), 3.37 (dt, J=11.2, 6.0 Hz, 2H), 3.00-2.80 (m, 2H), 2.44 (t, J=6.1 Hz, 2H), 2.21 (s, 3H), 1.77 (dq, J=11.8, 6.2 Hz, 2H).

Example 19: 17-methyl-4,5,8,13,16,17,20,26-octaazapentacyclo[20.3.1.1$^{2,5}$.1$^{8,11}$.0$^{13,17}$]octacosa-1(25),2(28),3,15,18,22(26),23-heptaene-14,21-dione (9)

6-[1-(2-Chloro-ethyl)-1H-pyrazol-4-yl]-pyridine-2-carboxylic acid {1-methyl-3-[(pyrrolidin-3-ylmethyl)-carbamoyl]-1H-pyrazol-4-yl}-amide

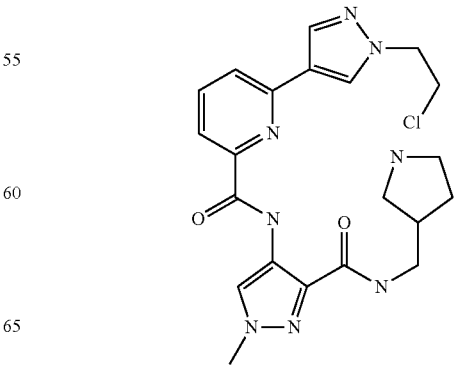

A mixture of lithium 4-({6-[1-(2-Chloro-ethyl)-1H-pyrazol-4-yl]-pyridine-2-carbonyl}-amino)-1-methyl-1H-pyrazole-3-carboxylate (150 mg; 0.39 mmol; 1.00 eq.), BOP (220 mg; 0.48 mmol; 1.22 eq.), Ethyl-diisopropyl-amine (0.14 mL; 0.79 mmol; 2.00 eq.), and 3-Aminomethyl-pyrrolidine-1-carboxylic acid tert-butyl ester (95 mg; 0.47 mmol; 1.20 eq.) in DMF (2 mL) was stirred at RT for 2 hr. The reaction mixture was diluted with water, solid precipitated out, filtered, collected product, which was added hydrogen chloride (0.98 mL; 3.94 mmol; 10.00 eq.), 1 mL methanol, and stirred at RT for 2 hr. removed off solvent, got residue, purified by basic prep HPLC, providing the title compound. LC-MS (M+1): 457.

17-methyl-4,5,8,13,16,17,20,26-octaazapentacyclo[20.3.1.1$^{2,5}$.1$^{8,11}$.0$^{15,19}$]octacosa-1(25),2(28),3,15,18,22(26),23-heptaene-14,21-dione (9)

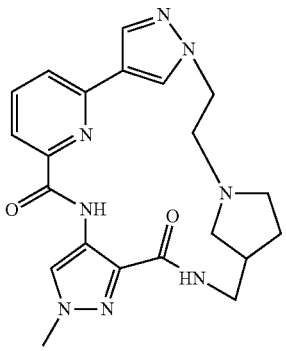 [SMILES: Cn1cc2c(n1)C(=O)NCC1CCN(CCn3cc(cn3)-c3cccc(n3)C(=O)N2)C1]

A mixture of 6-[1-(2-Chloro-ethyl)-1H-pyrazol-4-yl]-pyridine-2-carboxylic acid {1-methyl-3-[(pyrrolidin-3-ylmethyl)-carbamoyl]-1H-pyrazol-4-yl}-amide (60 mg; 0.13 mmol; 1.00 eq.), Ethyl-diisopropyl-amine (0.03 mL; 0.16 mmol; 1.20 eq.), potassium iodide (22 mg; 0.13 mmol; 1.00 eq.) and DMSO (6 mL) were added to a sealed tube then placed tube in a microwave at 125° C. for 2 hr. The reaction mixture was isolated by prep HPLC, providing the title compound. LC-MS (M+1): 421.

1H NMR (500 MHz, DMSO-d6) δ 12.92 (s, 1H), 8.89 (s, 1H), 8.65 (dd, J=7.6, 5.0 Hz, 1H), 8.25 (s, 1H), 8.12 (s, 1H), 7.98 (t, J=7.7 Hz, 1H), 7.90 (d, J=7.7 Hz, 1H), 7.79 (d, J=7.5 Hz, 1H), 4.37-4.21 (m, 2H), 3.93 (s, 3H), 3.86-3.73 (m, 1H), 3.26-3.13 (m, 2H), 3.12-3.01 (m, 1H), 2.81 (dd, J=14.0, 5.5 Hz, 2H), 2.24 (m, 2H), 2.14-2.00 (m, 1H), 1.91 (dt, J=8.2, 3.8 Hz, 1H), 1.45-1.33 (m, 1H).

Example 20 26-hydroxy-6-methyl-22-oxa-2,5,6,9,18,19,24,30-octaazapentacyclo[22.2.2.1$^{11,1^5}$.1$^{16,1^9}$.0$^{4,8}$]triaconta-4,7,11(30),12,14,16(29),17-heptaene-3,10,23-trione (21)

6-[1-(2-Chloro-ethyl)-1H-pyrazol-4-yl]-pyridine-2-carboxylic acid [3-((R)-3-hydroxy-piperidin-4-ylcarbamoyl)-1-methyl-1H-pyrazol-4-yl]-amide

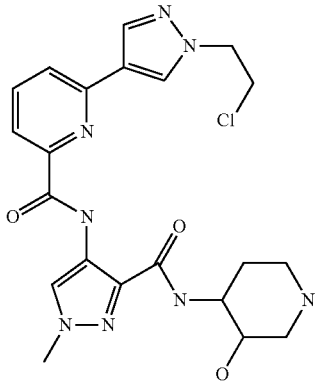 [SMILES: Cn1cc(NC(=O)c2cccc(-c3cnn(CCCl)c3)n2)c(C(=O)NC2CCNCC2O)n1]

A mixture of lithium 4-({6-[1-(2-Chloro-ethyl)-1H-pyrazol-4-yl]-pyridine-2-carbonyl}-amino)-1-methyl-1H-pyrazole-3-carboxylate (223 mg; 0.59 mmol; 1.00 eq.), HATU (245 mg; 0.64 mmol; 1.10 eq.) in DMF (4 mL), was stirred at RT for 15 min, and 4-Amino-3-hydroxy-piperidine-1-carboxylic acid tert-butyl ester (139 mg; 0.64 mmol; 1.10 eq.) (trans racemic) was added. The mixture was stirred at RT for 2 hr, poured into water (20 mL), extracted with DCM (30 mL×3), separated, washed with brine (20 mL), dried, and the solvent was removed. To the residue added methanol (2 mL), then hydrogen chloride (4.0M in dioxane) (1.03 mL; 4.10 mmol; 7.00 eq.), and the mixture was stirred at RT overnight. Another 1 mL of 4.0M HCl in dioxane was added and stirred for another 3 hr. The solvent was removed and got white solid, which was dissolved in DMSO (5 mL), 1 mL TEA was added, and the resulting solution was subjected to prep HPLC to provide the title compound (110 mg, yield 40%). LC-MS (M+1): 473.

26-hydroxy-6-methyl-22-oxa-2,5,6,9,18,19,24,30-octaazapentacyclo[22.2.2.1$^{11,1^5}$.1$^{16,1^9}$.0$^{4,8}$]triaconta-4,7,11(30),12,14,16(29),17-heptaene-3,10,23-trione (21)

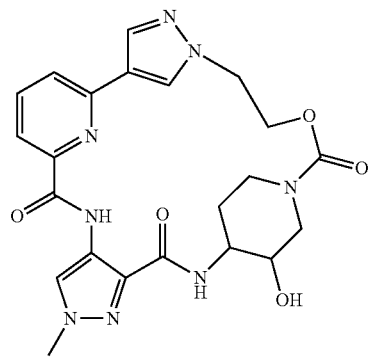 [SMILES: Cn1cc2c(n1)C(=O)NC1CCN(CC1O)C(=O)OCCn1cc(cn1)-c1cccc(n1)C(=O)N2]

A mixture of 6-[1-(2-Chloro-ethyl)-1H-pyrazol-4-yl]-pyridine-2-carboxylic acid [3-((R)-3-hydroxy-piperidin-4-ylcarbamoyl)-1-methyl-1H-pyrazol-4-yl]-amide (50 mg; 0.11 mmol; 1.00 eq.), Cs$_2$CO$_3$ (45 mg; 0.14 mmol; 1.30 eq.), potassium iodide (17 mg; 0.11 mmol; 1.00 eq.) and DMSO (5 mL) were added to a sealed tube, which was placed in a microwave at 110° C. for 60 min. The mixture was isolated by prep HPLC, providing the title compound (12 mg, yield 23.6%). LC-MS (M+1): 437.

$^1$H NMR (400 MHz, DMSO-d6) δ 12.11 (d, J=38.0 Hz, 1H), 8.52 (d, J=6.2 Hz, 1H), 8.39-8.18 (m, 3H), 8.06-7.79 (m, 3H), 5.23 (s, 1H), 5.04 (s, 1H), 4.73 (s, 2H), 4.49 (s, 2H), 4.17 (d, J=14.7 Hz, 1H), 3.93 (s, 3H), 3.08 (s, 1H), 2.40-2.27 (m, 3H), 1.69 (s, 1H).

Scheme 6
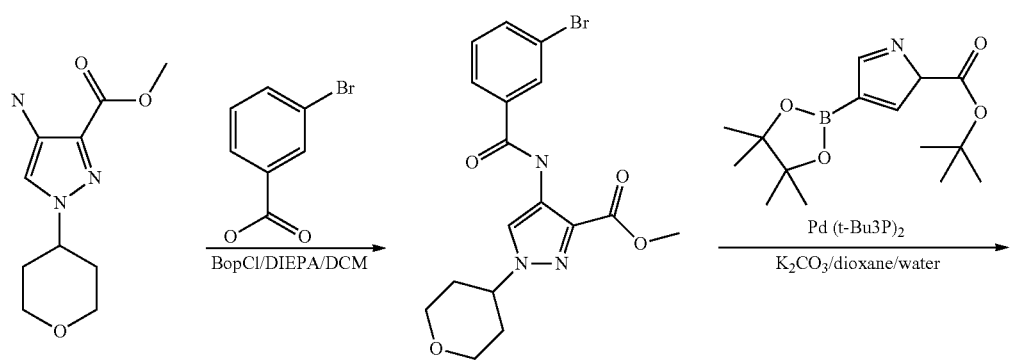
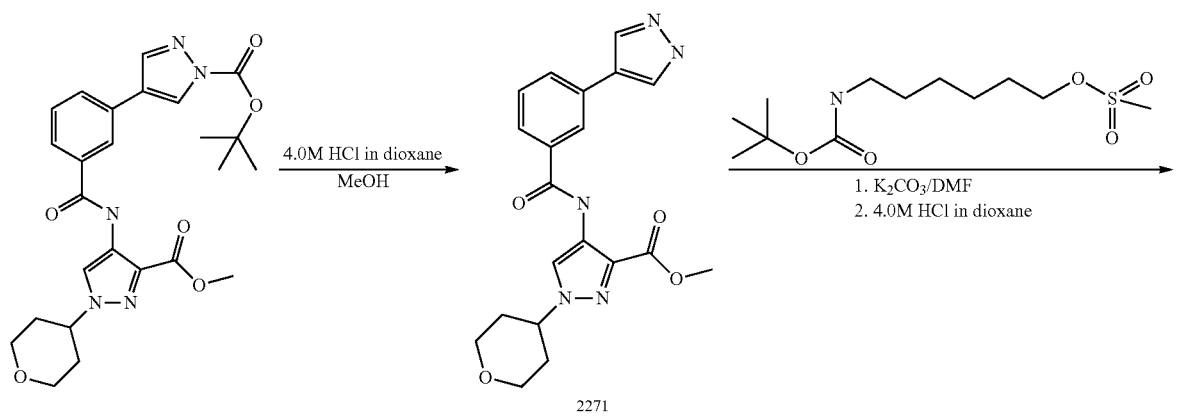
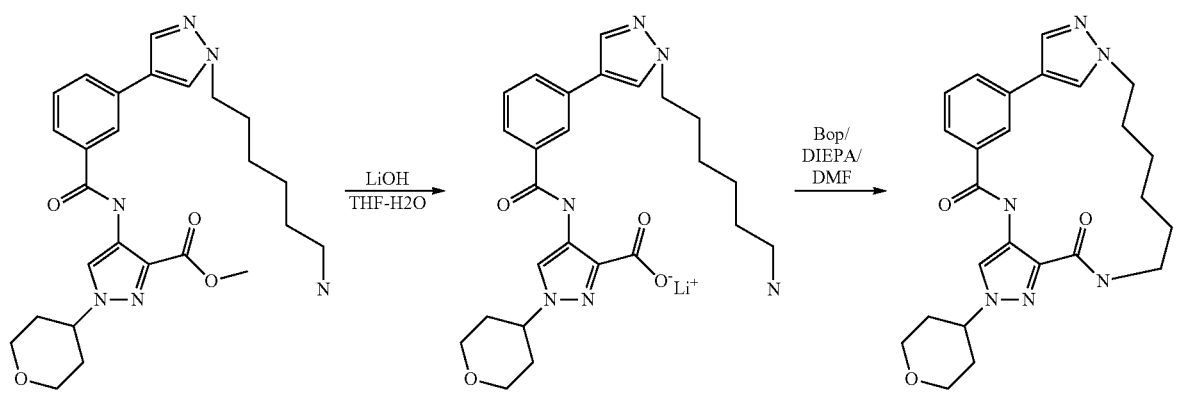

Intermediates

4-(3-Bromo-benzoylamino)-1-(tetrahydro-pyran-4-yl)-1H-pyrazole-3-carboxylic acid methyl ester

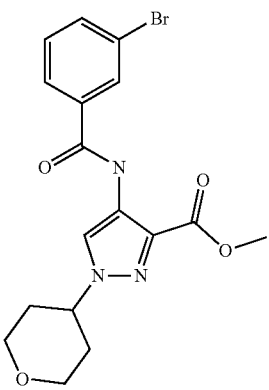 [SMILES: COC(=O)c1nn(C2CCOCC2)cc1NC(=O)c1cccc(Br)c1]

A mixture of 3-Bromo-benzoic acid (1900. mg; 9.26 mmol; 1.00 eq.), Ethyl-diisopropyl-amine (3.61 mL; 20.38 mmol; 2.20 eq.), methyl 4-amino-1-(tetrahydro-2h-pyran-4-yl)-1h-pyrazole-3-carboxylate (2190 mg; 9.73 mmol; 1.05 eq.) and 3-[chloro-(2-oxooxazolidin-3-yl)phosphoryl]oxazolidin-2-one (2829 mg; 11.12 mmol; 1.20 eq.) in DCM (100 mL) was stirred at RT for 3 hr. The reaction mixture was washed with brine, dried over $Na_2SO_4$, and the solvent was evaporated off, to provide the title compound as a white solid 3850 mg (quantitative yield). LC-MS (M+1): 408/410.

4-[3-(1-tert-Butoxycarbonyl-1H-pyrazol-4-yl)-benzoylamino]-1-(tetrahydro-pyran-4-yl)-1H-pyrazole-3-carboxylic acid methyl ester

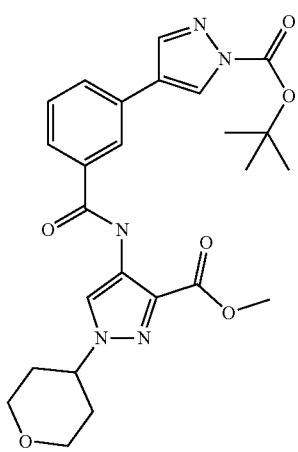 [SMILES: COC(=O)c1nn(C2CCOCC2)cc1NC(=O)c1cccc(-c2cnn(C(=O)OC(C)(C)C)c2)c1]

A mixture of 4-(3-Bromo-benzoylamino)-1-(tetrahydro-pyran-4-yl)-1H-pyrazole-3-carboxylic acid methyl ester (1889 mg; 4.63 mmol; 1.00 eq.), 4-(4,4,5,5-Tetramethyl-[1,3,2]dioxaborolan-2-yl)-pyrazole-1-carboxylic acid tert-butyl ester (1497 mg; 5.09 mmol; 1.10 eq.), dipotassium carbonate (703 mg; 5.09 mmol; 1.10 eq.) in dioxane (130 mL) and water (13 mL) was degassed, the added palladium; tritert-butylphosphane (118 mg; 0.23 mmol; 0.05 eq.). The mixture was stirred at 40° C. for 24 hr, diluted with EA (100 mL), washed with brine (100 mL×2), dried over $MgSO_4$, evaporated off solvent to provide a residue, which was purified by SNAP column (100 g) (eluted with EA in hexane (20% to 80%). Collected title compound (1500 mg, yield 65%). LC-MS (M+1): 496.

4-[3-(1H-Pyrazol-4-yl)-benzoylamino]-1-(tetrahydro-pyran-4-yl)-1H-pyrazole-3-carboxylic acid methyl ester

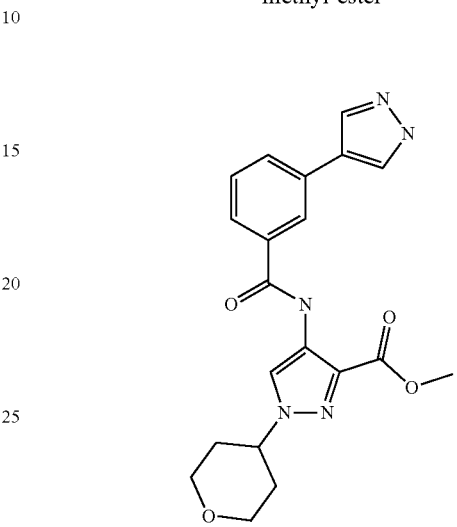

To a solution of 4-[3-(1-tert-Butoxycarbonyl-1H-pyrazol-4-yl)-benzoylamino]-1-(tetrahydro-pyran-4-yl)-1H-pyrazole-3-carboxylic acid methyl ester (1500 mg; 3.03 mmol; 1.00 eq.) in methanol (5 mL) was added hydrogen chloride (6 mL; 24.22 mmol; 8.00 eq.), the mixture was stirred for 4 hr at RT. The solvent was removed, providing a white solid, to which 10 mL of 5% $Na_2CO_3$ (aq) was added. The mixture was stirred at RT for 30 min and filtered to give the title compound as a white solid. LC-MS (M+1): 396.

4-{3-[1-(6-Amino-hexyl)-1H-pyrazol-4-yl]-benzoylamino}-1-(tetrahydro-pyran-4-yl)-1H-pyrazole-3-carboxylic acid methyl ester

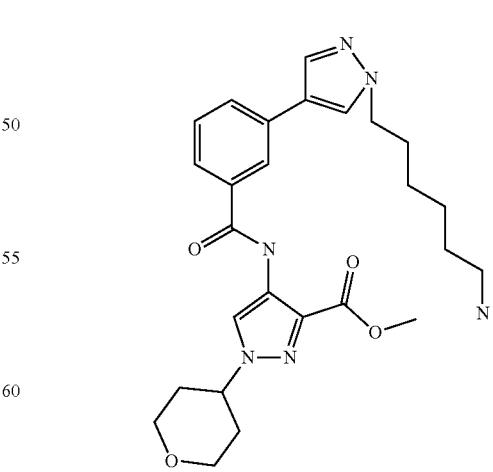

A mixture of 4-[3-(1H-Pyrazol-4-yl)-benzoylamino]-1-(tetrahydro-pyran-4-yl)-1H-pyrazole-3-carboxylic acid methyl ester (130. mg; 0.33 mmol; 1.00 eq.), Methanesulfonic acid 6-tert-butoxycarbonylamino-hexyl ester (102 mg; 0.35 mmol; 1.05 eq.) and dipotassium carbonate (50 mg; 0.36 mmol; 1.10 eq.) in DMF (2 mL) was stirred at 80° C. for 2 hr. The mixture was diluted with water, extracted with EA, the organic layer was washed with brine, dried, and the solvent was removed. To the residue was added methanol (1 mL), and hydrogen chloride (4.0M in dioxane) (0.82 mL; 3.29 mmol; 10.00 eq.), and the mixture was stirred at RT for overnight. The solvent was removed, the residue was dissolved in DMSO, neutralized with TEA, and purified by prep HPLC to provide the title compound. LC-MS (M+1): 495.

Lithium 4-{3-[1-(6-Amino-hexyl)-1H-pyrazol-4-yl]-benzoylamino}-1-(tetrahydro-pyran-4-yl)-1H-pyrazole-3-carboxylate

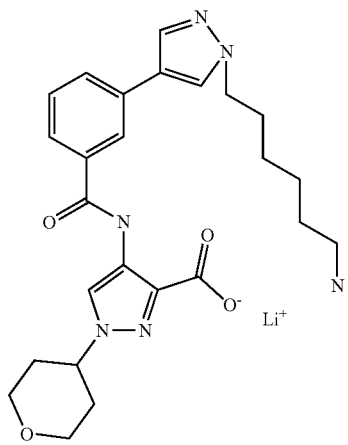 [SMILES: NCCCCCCn1cc(-c2cccc(C(=O)Nc3cn(C4CCOCC4)nc3C(=O)[O-])c2)cn1 ; [Li+]]

A mixture of 4-{3-[1-(6-Amino-hexyl)-1H-pyrazol-4-yl]-benzoylamino}-1-(tetrahydro-pyran-4-yl)-1H-pyrazole-3-carboxylic acid methyl ester (37 mg; 0.07 mmol; 1.00 eq.), lithium hydroxide hydrate (6.3 mg; 0.15 mmol; 2.00 eq.) in THF (1 mL) and water (1 mL) was stirred at RT overnight. The solvent was removed and the residue was dried and used directly in the next step. LC-MS (M+1): 481.

Example 21 16-(oxan-4-yl)-4,5,12,15,16,19-hexaazatetracyclo[19.3.1.1$^{2,5}$.0$^{14,1^{8}}$]hexacosa-1(24),2(26),3,14,17,21(25),22-heptaene-13,20-dione (24)

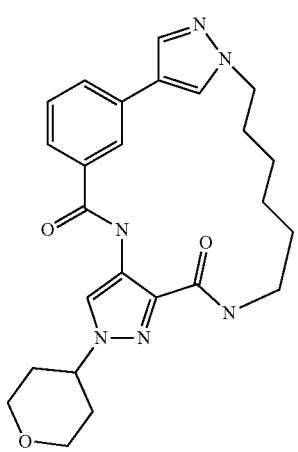 [SMILES: O=C1Nc2cn(C3CCOCC3)nc2C(=O)NCCCCCCn2cc(cn2)-c2cccc1c2]

To a mixture of lithium 4-{3-[1-(6-Amino-hexyl)-1H-pyrazol-4-yl]-benzoylamino}-1-(tetrahydro-pyran-4-yl)-1H-pyrazole-3-carboxylate (34 mg; 0.07 mmol; 1.00 eq.), Ethyl-diisopropyl-amine (0.01 mL; 0.08 mmol; 1.20 eq.) in DMF (8 mL) was added (Benzotriazol-1-yloxy) tris(dimethylamino) phosphonium hexafluorophosphate (38 mg; 0.08 mmol; 1.20 eq.). The reaction was stirred at RT for 2 hr. The solvent was removed, and purified by prep HPLC to provide the title compound. LC-MS (M+1): 463.

$^{1}$H NMR (400 MHz, Methanol-d4) δ 8.30-8.20 (m, 2H), 8.17 (s, 1H), 7.87-7.69 (m, 3H), 7.57 (t, J=7.7 Hz, 1H), 4.65-4.42 (m, 2H), 4.39-4.28 (m 2H), 4.16-4.03 (m, 2H), 3.61 (td, J=11.8, 2.4 Hz, 2H), 3.43 (t, J=7.2 Hz, 2H), 2.27-2.03 (m, 3H), 1.95 (dt, J=11.5, 7.1 Hz, 2H), 1.85-1.70 (m, 2H), 1.60 (dq, J=23.6, 7.9 Hz, 4H).

Example 22 15-(oxan-4-yl)-8-oxa-4,5,11,14,15,18-hexaazatetracyclo[18.3.1.1$^{2,5}$.0$^{13,1^{7}}$]pentacosa-1(23),2(25),3,13,16,20(24),21-heptaene-12,19-dione (20)

4-(3-{11-[2-(2-Amino-ethoxy)-ethyl]-1H-pyrazol-4-yl}-benzoylamino)-1-(tetrahydro-pyran-4-yl)-1H-pyrazole-3-carboxylic acid methyl ester

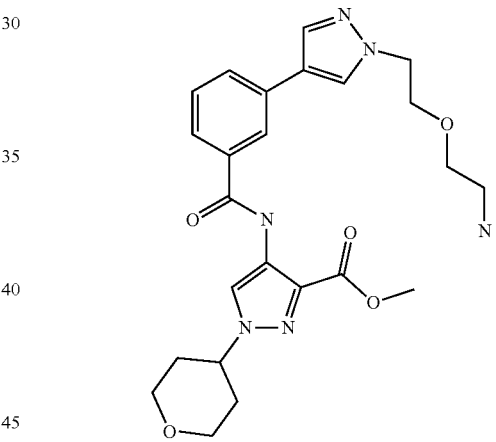

A mixture of 4-[3-(1H-Pyrazol-4-yl)-benzoylamino]-1-(tetrahydro-pyran-4-yl)-1H-pyrazole-3-carboxylic acid methyl ester hydrochloride (3) (300 mg; 0.59 mmol; 1.00 eq.), and Cs$_2$CO$_3$ (484 mg; 1.49 mmol; 2.50 eq.) in DMF (5 mL) was stirred at RT for 30 min. To it added Methanesulfonic acid 2-(2-tert-butoxycarbonylamino-ethoxy)-ethyl ester (185.23 mg; 0.65 mmol; 1.10 eq.), and the reaction was heated at 80° C. stirring for 1 hr. The mixture was cooled, poured into water, extracted with EA (30 mL×3), dried over MgSO$_4$, evaporated off solvent to provide 4-(3-{1-[2-(2-tert-Butoxycarbonylamino-ethoxy)-ethyl]-1H-pyrazol-4-yl}-benzoylamino)-1-(tetrahydro-pyran-4-yl)-1H-pyrazole-3-carboxylic acid methyl ester. To the above product added methanol (2 mL), then hydrogen chloride (4.0M in dioxane) (1.19 mL; 4.75 mmol; 8.00 eq.), as resulting mixture was stirred at RT for 3 hr. The solvent was removed to provide a residue which was subjected to prep HPLC (basic) for isolation, affording the title compound (140 mg, yield 48.8%). LC-MS (M+1): 483.

Lithium 4-(3-{1-[2-(2-Amino-ethoxy)-ethyl]-1H-pyrazol-4-1}-benzoylamino)-1-(tetrahydro-pyran-4-yl)-1H-pyrazole-3-carboxylate

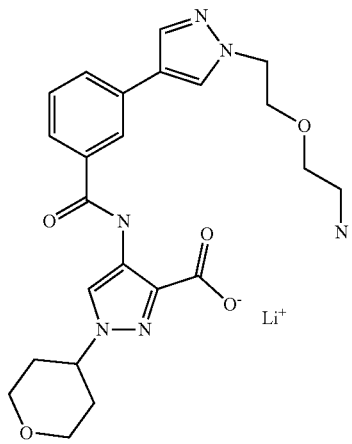 [SMILES: NCCOCCn1cc(-c2cccc(C(=O)Nc3cn(C4CCOCC4)nc3C(=O)[O-])c2)cn1 ; [Li+]]

A mixture of 4-(3-{1-[2-(2-Amino-ethoxy)-ethyl]-1H-pyrazol-4-yl}-benzoylamino)-1-(tetrahydro-pyran-4-yl)-1H-pyrazole-3-carboxylic acid methyl ester (142.00 mg; 0.29 mmol; 1.00 eq.), lithium hydroxide hydrate (24.70 mg; 0.59 mmol; 2.00 eq.) in THF (2 mL) and water (2 mL) was stirred at RT for 20 min. The solvent was removed and dried to provide a white solid as the title compound, which was directly used in the next step. LC-MS (M+1): 476.

15-(oxan-4-yl)-8-oxa-4,5,11,14,15,18-hexaazatetracyclo[18.3.1.1$^{2,5}$.0$^{13,1}$]pentacosa-1(23),2(25),3,13,16,20(24),21-heptaene-12,19-dione (20)

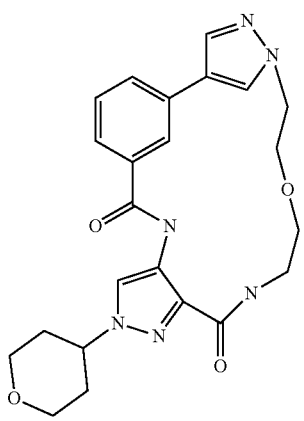 [SMILES: O=C1Nc2cn(C3CCOCC3)nc2C(=O)NCCOCCn2cc(cn2)-c2cccc1c2]

A mixture of lithium 4-(3-{1-[2-(2-Amino-ethoxy)-ethyl]-1H-pyrazol-4-yl}-benzoylamino)-1-(tetrahydro-pyran-4-yl)-1H-pyrazole-3-carboxylate (138 mg; 0.29 mmol; 1.00 eq.), BOP (159 mg; 0.35 mmol; 1.20 eq.) and Ethyl-diisopropyl-amine (0.06 mL; 0.35 mmol; 1.20 eq.) in DMF (14 mL) was stirred at RT for 20 min. The solvent was removed, and the residue was dissolved in DMSO, then subjected to prep HPLC to afford the title compound (28 mg, yield 21.8%). LC-MS (M+1): 451.
$^1$H NMR (400 MHz, DMSO-d6) δ 10.36 (s, 1H), 8.21-8.09 (m, 2H), 7.89 (t, J=5.7 Hz, 1H), 7.86-7.76 (m, 2H), 7.57 (dt, J=7.7, 1.3 Hz, 1H), 7.40 (dt, J=7.8, 1.5 Hz, 1H), 7.28 (t, J=7.7 Hz, 1H), 4.40-4.20 (m, 3H), 4.00-3.89 (m, 2H), 3.85 (t, J=4.9 Hz, 2H), 3.58 (t, J=5.4 Hz, 2H), 3.53-3.35 (m, 4H), 1.93 (m, 4H).

Scheme 7

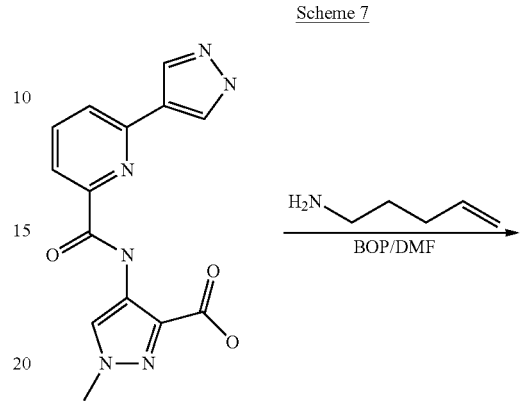

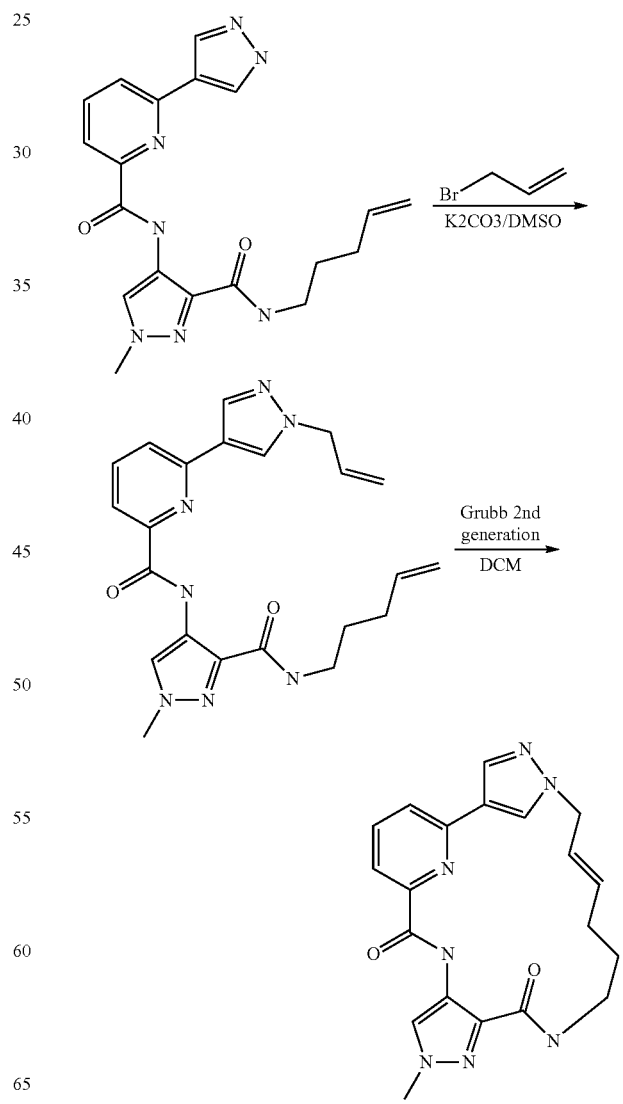

Intermediates

6-(1H-Pyrazol-4-yl)-pyridine-2-carboxylic acid (1-methyl-3-pent-4-enylcarbamoyl-1H-pyrazol-4-yl)-amide

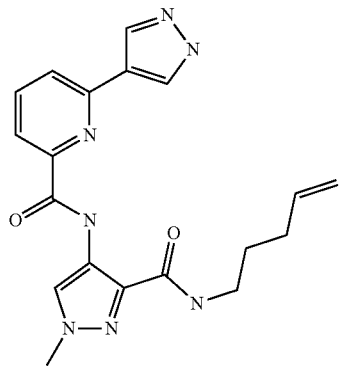 [SMILES: C=CCCCNC(=O)c1nn(C)cc1NC(=O)c1cccc(-c2cn[nH]c2)n1]

A mixture of lithium 1-Methyl-4-{[6-(1H-pyrazol-4-yl)-pyridine-2-carbonyl]-amino}-1H-pyrazole-3-carboxylate (300.00 mg; 0.94 mmol; 1.00 eq.), (Benzotriazol-1-yloxy)tris(dimethylamino) phosphonium hexafluorophosphate (515.83 mg; 1.13 mmol; 1.20 eq.) And Ethyl-diisopropyl-amine (0.20 mL; 1.13 mmol; 1.20 eq.) in DMF (4 mL) were stirred at RT for 20 min. The solvent was removed to afford a residue which was dissolved in DMSO and subjected to prep HPLC to provide the title compound (158 mg, yield 44%). LC-MS (M+1): 380.

6-(1-Allyl-1H-pyrazol-4-yl)-pyridine-2-carboxylic acid (1-methyl-3-pent-4-enylcarbamoyl-1H-pyrazol-4-yl)-amide

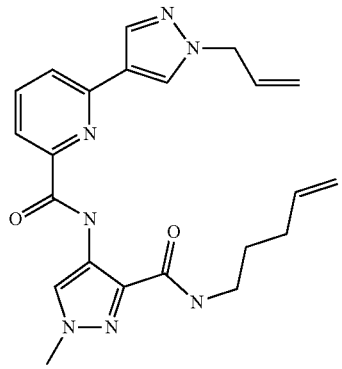 [SMILES: C=CCCCNC(=O)c1nn(C)cc1NC(=O)c1cccc(-c2cnn(CC=C)c2)n1]

A mixture of 6-(1H-Pyrazol-4-yl)-pyridine-2-carboxylic acid (1-methyl-3-pent-4-enylcarbamoyl-1H-pyrazol-4-yl)-amide (150 mg; 0.40 mmol; 1.00 eq.), 3-Bromo-propene (0.07 mL; 0.79 mmol; 2.00 eq.), and $Cs_2CO_3$ (155 mg; 0.47 mmol; 1.20 eq.) were stirred at RT for 4 hr. The reaction was quenched with aqueous $NH_4Cl$, then diluted with water, and a white solid precipitated out, filtered to provide an off white solid as title compound (120 mg, yield 72.4%). LC-MS (M+1): 420.

Example 23 (7E)-16-methyl-4,5,12,15,16,19,25-heptaazatetracyclo[19.3.1.1$^{2,5}$.0$^{14,18}$]hexacosa-1(24),2(26),3,7,14,17,21(25),22-octaene-13,20-dione (25)

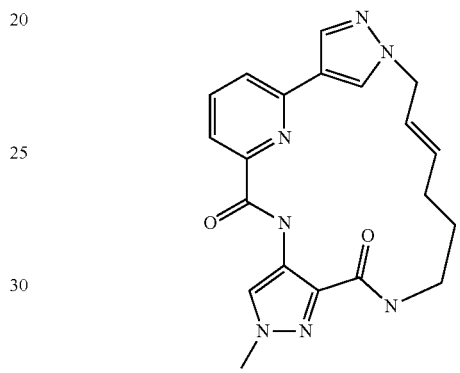

To a solution of 6-(1-Allyl-1H-pyrazol-4-yl)-pyridine-2-carboxylic acid (1-methyl-3-pent-4-enylcarbamoyl-1H-pyrazol-4-yl)-amide (60 mg; 0.14 mmol; 1.00 eq.) and DCM (10 mL) was added benzylidene-[1,3-bis(2,4,6-trimethyl-phenyl)imidazolidin-2-ylidene]-dichloro-ruthenium; tricyclohexylphosphane (24 mg; 0.03 mmol; 0.20 eq.). The mixture was stirred at 40° C. for 2 days. The solvent was removed and the residue was purified by prep HPLC to afford the title compound. LC-MS (M+1): 392.

$^1$H NMR (500 MHz, DMSO-d6) δ 12.86 (s, 1H), 8.95 (s, 1H), 8.73 (d, J=5.8 Hz, 1H), 8.28 (s, 1H), 8.17 (s, 1H), 8.08-7.97 (m, 1H), 7.93 (s, 1H), 7.81 (d, J=7.5 Hz, 1H), 6.33 (d, J=15.3 Hz, 1H), 5.87 (dd, J=15.2, 7.6 Hz, 1H), 4.80 (d, J=7.0 Hz, 2H), 3.93 (s, 3H), 2.10 (s, 2H), 1.73 (s, 2H), 2.41-2.28 (m, 2H).

Scheme 8

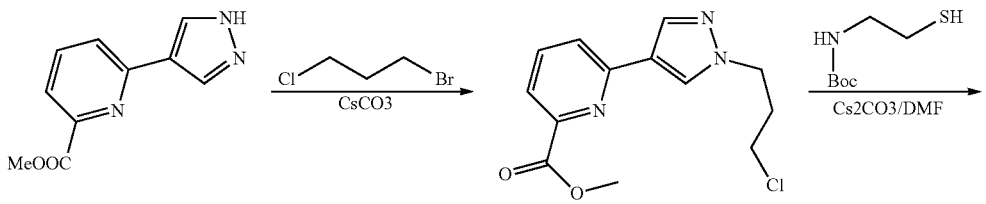

-continued
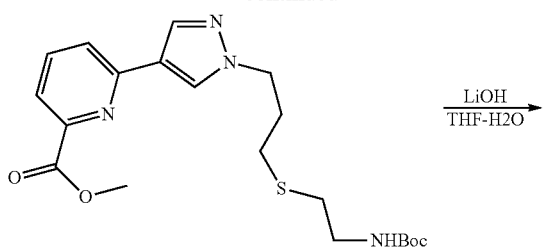
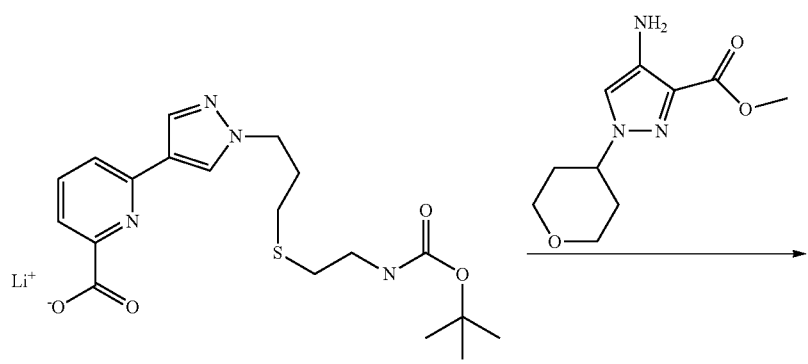
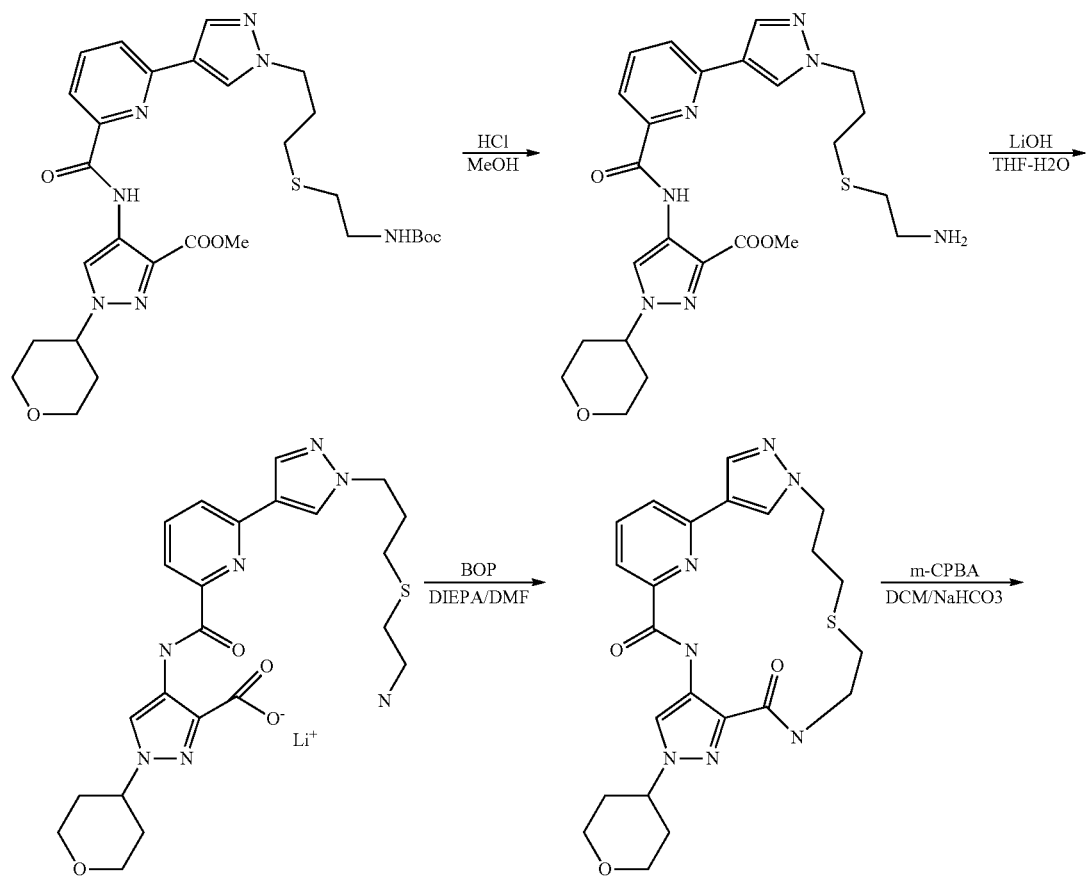

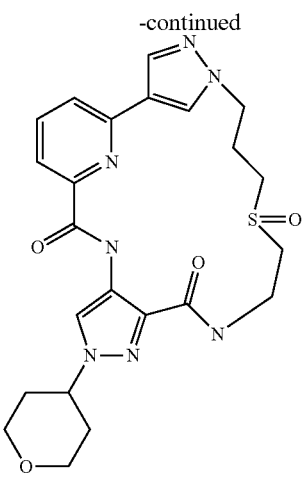

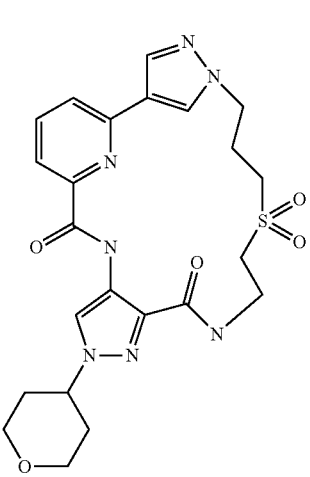

+

Intermediates

6-[1-(3-Chloro-propyl)-1H-pyrazol-4-yl]-pyridine-2-carboxylic acid methyl ester

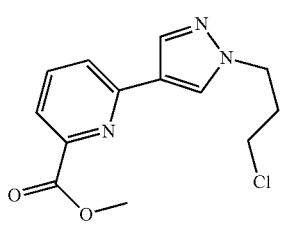 [SMILES: COC(=O)c1cccc(-c2cnn(CCCCl)c2)n1]

A mixture of 6-(1H-Pyrazol-4-yl)-pyridine-2-carboxylic acid methyl ester (500.00 mg; 2.46 mmol; 1.00 eq.), 1-Bromo-3-chloro-propane (0.49 mL; 4.92 mmol; 2.00 eq.) and $Cs_2CO_3$ (1603 mg; 2.95 mmol; 1.20 eq.) was stirred at 80° C. for 20 min. The reaction was cooled, poured into water, extracted with EA, washed with brine, dried over $MgSO_4$, and evaporated off solvent gave crude product, which was subjected to SNAP column (25 g, eluted with 10%-80% EA in hexane) to provide the title product (600 mg, yield 87%). LC-MS (M+1): 280.

6-{1-[3-(2-tert-Butoxycarbonylamino-ethylsulfanyl)-propyl]-1H-pyrazol-4-yl}-pyridine-2-carboxylic acid methyl ester

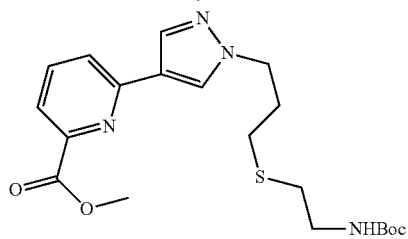

A mixture of (2-Mercapto-ethyl)-carbamic acid tert-butyl ester (0.29 mL; 1.68 mmol; 1.30 eq.), $Cs_2CO_3$ (548 mg; 1.68 mmol; 1.30 eq.) and 6-[1-(3-Chloro-propyl)-1H-pyrazol-4-yl]-pyridine-2-carboxylic acid methyl ester (362 mg; 1.29 mmol; 1.00 eq.) in DMF (3 mL) was stirred at 60° C. for 3 hr. The reaction mixture was diluted with water, extracted with EA, concentrated, got residue was purified by SNAP column (25 g, eluent with 20%-100% EA in hexane), providing the title compound (440 mg, yield 80.8%). LC-MS (M+1): 421.

Lithium 6-{1-[3-(2-tert-Butoxycarbonylamino-ethylsulfanyl)-propyl]-1H-pyrazol-4-yl}-pyridine-2-carboxylate

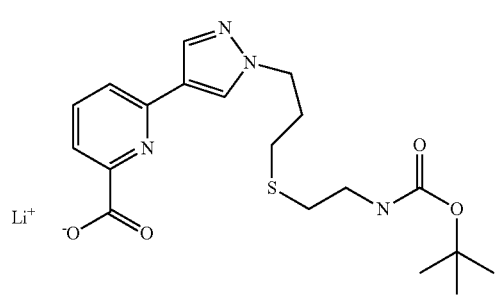

A mixture of 6-{1-[3-(2-tert-Butoxycarbonylamino-ethylsulfanyl)-propyl]-1H-pyrazol-4-yl}-pyridine-2-carboxylic acid methyl ester (260 mg; 0.62 mmol; 1.00 eq.), lithium hydroxide hydrate (52 mg; 1.24 mmol; 2.00 eq.) in THF (2 mL) and water (2 mL) was stirred at RT for 1 hr. The solvent was removed, dried in vacuum oven, providing a white solid which was directly used in the next step. LC-MS (M+1): 407.

4-[(6-{1-[3-(2-Amino-ethylsulfanyl)-propyl]-1H-pyrazol-4-yl}-pyridine-2-carbonyl)-amino]-1-(tetrahydro-pyran-4-yl)-1H-pyrazole-3-carboxylic acid methyl ester

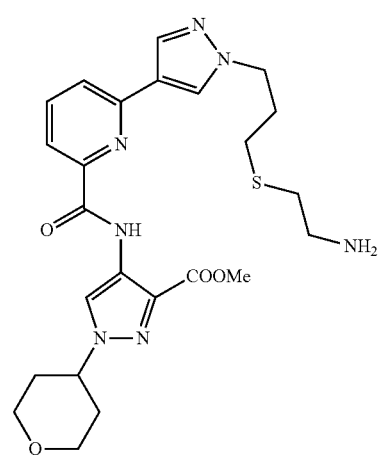 [SMILES: COC(=O)c1nn(C2CCOCC2)cc1NC(=O)c1cccc(-c2cnn(CCCSCCN)c2)n1]

To a solution of 6-{1-[3-(2-tert-Butoxycarbonylamino-ethylsulfanyl)-propyl]-1H-pyrazol-4-yl}-pyridine-2-carboxylic acid lithium (256 mg; 0.62 mmol; 1.00 eq.), Ethyl-diisopropyl-amine (0.23 mL; 1.30 mmol; 2.10 eq.) in DCM (6 mL), was added 3-[chloro-(2-oxooxazolidin-3-yl)phosphoryl]oxazolidin-2-one (189 mg; 0.74 mmol; 1.20 eq.). The mixture were stirred for 15 min at RT, then 4-Amino-1-(tetrahydro-pyran-4-yl)-1H-pyrazole-3-carboxylic acid methyl ester (154 mg; 0.68 mmol; 1.10 eq.) was added, cintined stir at RT for 24 hr. Additional BopCl (50 mg) and DIEPA 0.05 mL were added, stirred for another 2 days. Water (5 mL) and DCM (30 mL) were added to the reaction solution, which was washed with 5 mL 5% NaHCO$_3$ (aq), then brine, the organic layer was separated out, dried over Na$_2$SO$_4$, evaporated off solvent, providing 4-[(6-{1-[3-(2-tert-Butoxycarbonylamino-ethylsulfanyl)-propyl]-1H-pyrazol-4-yl}-pyridine-2-carbonyl)-amino]-1-(tetrahydro-pyran-4-yl)-1H-pyrazole-3-carboxylic acid methyl ester as a residue. LC-MS (M+1): 614. To the above product was added methanol (2 mL), then hydrogen chloride (1.24 mL; 4.96 mmol; 8.00 eq.), the mixture was stirred at RT for overnight. The solvent was removed, providing an off white solid, which was added 3 mL 10% Na$_2$CO$_3$ (aq), and mixture was stirred at RT for 30 min, filtered to provide 318 mg of the tittle compound as a white solid (quantitative yield). LC-MS (M+1): 514.

Lithium 4-[(6-{1-[3-(2-Amino-ethylsulfanyl)-propyl]-1H-pyrazol-4-yl}-pyridine-2-carbonyl)-amino]-1-(tetrahydro-pyran-4-yl)-1H-pyrazole-3-carboxylate

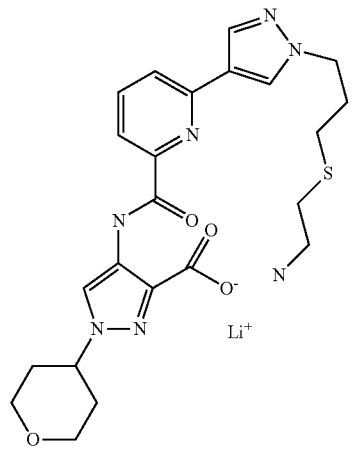 [SMILES: NCCSCCCn1cc(-c2cccc(C(=O)Nc3cn(C4CCOCC4)nc3C(=O)[O-])n2)cn1 ; [Li+]]

A mixture of 4-[(6-{1-[3-(2-Amino-ethylsulfanyl)-propyl]-1H-pyrazol-4-yl}-pyridine-2-carbonyl)-amino]-1-(tetrahydro-pyran-4-yl)-1H-pyrazole-3-carboxylic acid methyl ester (308.17 mg; 0.60 mmol; 1.00 eq.), lithium hydroxide hydrate (50. mg; 1.20 mmol; 2.00 eq.) in THF (2 mL) and water (2 mL) was stirred at RT overnight. The solvent was removed and dried to provide an off white solid as title compound, which was directly used in the next step. LC-MS (M+1): 500.

Example 24 6-(oxan-4-yl)-9-thia-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (13)

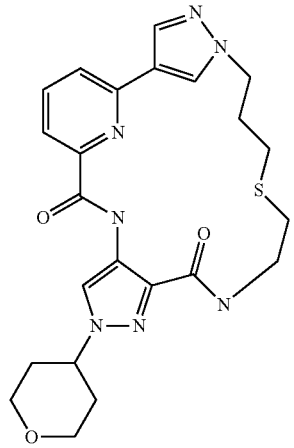 [SMILES: O=C1Nc2cn(C3CCOCC3)nc2C(=O)NCCSCCCn2cc(cn2)-c2cccc1n2]

A mixture of lithium 4-[(6-{1-[3-(2-Amino-ethylsulfanyl)-propyl]-1H-pyrazol-4-yl}-pyridine-2-carbonyl)-amino]-1-(tetrahydro-pyran-4-yl)-1H-pyrazole-3-carboxylate (303 mg; 0.60 mmol; 1.00 eq.), (Benzotriazol-1-yloxy)tris(dimethylamino)phosphonium hexafluorophosphate (328 mg; 0.72 mmol; 1.20 eq.) and Ethyl-diisopropyl-amine (0.13 mL; 0.72 mmol; 1.20 eq.) in DMF (40 mL) were stirred at RT for 20 min. The solvent was removed and the residue was dissolved in DMSO, subjected to prep HPLC, providing the title compound (58 mg, yield 20%). LC-MS (M+1): 482.

$^1$H NMR (400 MHz, DMSO-d6) δ 12.74 (s, 1H), 9.19 (s, 1H), 8.81 (t, J=5.9 Hz, 1H), 8.37 (s, 1H), 8.11 (s, 1H), 8.03 (t, J=7.7 Hz, 1H), 7.91 (dd, J=7.9, 1.0 Hz, 1H), 7.83 (dd, J=7.5, 0.9 Hz, 1H), 4.56 (p, J=7.9 Hz, 1H), 4.29 (t, J=7.4 Hz, 2H), 4.01 (m, 2H), 3.54-3.34 (m, 4H), 2.84-2.68 (m, 4H), 2.51-2.40 (m, 2H), 2.05 (m, 4H).

Example 25 16-(oxan-4-yl)-9λ$^4$-thia-4,5,12,15,16,19,25-heptaazatetracyclo[19.3.1.1$^{2,5}$.0$^{14,18}$]hexacosa-1(24),2(26),3,14,17,21(25),22-heptaene-9,13,20-trione (14)

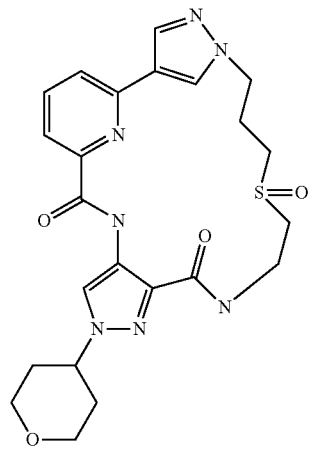 [SMILES: O=C1Nc2cn(C3CCOCC3)nc2C(=O)NCCS(=O)CCCn2cc(cn2)-c2cccc1n2]

To a solution of 6-{1-[3-(2-tert-Butoxycarbonylamino-ethylsulfanyl)-propyl]-1H-pyrazol-4-yl}-pyridine-2-carboxylic acid methyl ester (50 mg; 0.10 mmol; 1.00 eq.) in DCM (4 mL) was added sodium hydrogen carbonate (45 mg; 0.54 mmol; 5.16 eq.). then 3-chloroperbenzoic acid (29 mg; 0.12 mmol; 1.20 eq.), the mixture was stirred at RT for 1 hr. removed off solvent, got residue was purified by prep HPLC providing the title compound. LC-MS (M+1): 498.

$^1$H NMR (400 MHz, DMSO-d6) δ 12.60 (s, 1H), 8.96 (s, 1H), 8.82 (t, J=5.9 Hz, 1H), 8.39 (s, 1H), 8.13 (s, 1H), 8.04 (t, J=7.7 Hz, 1H), 7.91 (dd, J=7.9, 1.0 Hz, 1H), 7.85 (dd, J=7.6, 0.9 Hz, 1H), 4.56 (q, J=8.0 Hz, 1H), 4.40 (m, 2H), 3.99 (m, 2H), 3.85 (m, 2H), 3.59-3.37 (m, 2H), 3.19 (m, 2H), 3.07-2.89 (m, 2H), 2.39 (m, 2H), 2.05 (m, 4H).

Example 26 16-(oxan-4-yl)-9λ$^6$-thia-4,5,12,15,16,19,25-heptaazatetracyclo[19.3.1.1$^{2,5}$.0$^{14,18}$]hexacosa-1(24),2(26),3,14,17,21(25),22-heptaene-9,9,13,20-tetrone (15)

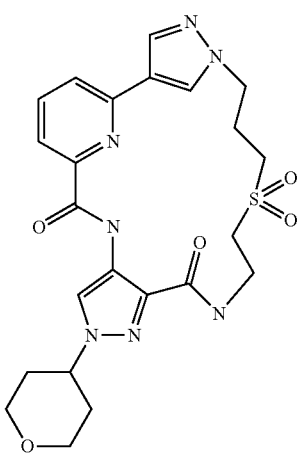 [SMILES: O=C1Nc2cn(C3CCOCC3)nc2C(=O)NCCS(=O)(=O)CCCn2cc(cn2)-c2cccc1n2]

To a solution of 6-{1-[3-(2-tert-Butoxycarbonylamino-ethylsulfanyl)-propyl]-1H-pyrazol-4-yl}-pyridine-2-carboxylic acid methyl ester (50 mg; 0.10 mmol; 1.00 eq.) in DCM (4 mL) was added sodium hydrogen carbonate (45 mg; 0.54 mmol; 5.16 eq.), Then 3-chloroperbenzoic acid (29 mg; 0.12 mmol; 1.20 eq.), the mixture was stirred at RT for 1 hr. removed off solvent, got residue was purified by prep HPLC providing the title compound. LC-MS (M+1): 514.

$^1$H NMR (400 MHz, DMSO-d6) δ 12.59 (s, 1H), 9.08 (s, 1H), 8.81 (t, J=5.8 Hz, 1H), 8.41 (s, 1H), 8.18-7.96 (m, 2H), 7.88 (m, 2H), 4.65-4.46 (m, 1H), 4.38 (t, J=7.4 Hz, 2H), 4.08-3.93 (m, 4H), 3.69 (dd, J=9.8, 5.4 Hz, 2H), 3.49 (m, 6H), 2.06 (m, 4H).

Example 27 (8Z)-16-methyl-4,5,12,15,16,19,25-heptaazatetracyclo[19.3.1.1$^{2,5}$.0$^{14,18}$]hexacosa-1(24),2(26),3,8,14,17,21(25),22-octaene-13,20-dione (27)

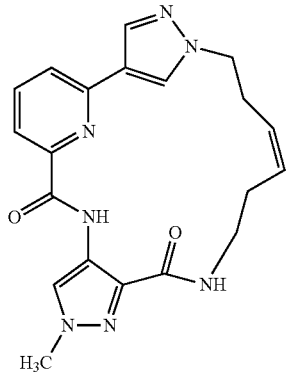 [SMILES: Cn1cc2c(n1)C(=O)NCC/C=C\CCn1cc(cn1)-c1cccc(n1)C(=O)N2]

The title compound was prepared in the same manner as Example 23, substituting compound 6-(1-Allyl-1H-pyrazol-4-yl)-pyridine-2-carboxylic acid (1-methyl-3-pent-4-enyl-carbamoyl-1H-pyrazol-4-yl)-amide with compound 6-(1-But-3-enyl-1H-pyrazol-4-yl)-pyridine-2-carboxylic acid (3-but-3-enylcarbamoyl-1-methyl-1H-pyrazol-4-yl)-amide in the last step cyclization.

LC-MS (M+1): 392. $^1$H NMR (400 MHz, Chloroform-d) δ 12.96 (s, 1H), 9.66 (t, J=1.7 Hz, 1H), 8.20 (s, 1H), 7.97-7.83 (m, 2H), 7.61 (dd, J=7.6, 2.1 Hz, 1H), 7.28 (d, J=1.9 Hz, 1H), 7.08 (s, 1H), 5.74-5.63 (m, 2H), 4.28 (dt, J=8.8, 4.4 Hz, 2H), 3.96 (t, J=1.8 Hz, 3H), 3.43 (d, J=9.0 Hz, 2H), 3.21-3.11 (m, 2H), 2.61 (d, J=9.3 Hz, 2H).

Example 28 (8E)-16-methyl-4,5,12,15,16,19,25-heptaazatetracyclo[19.3.1.1$^{2,5}$.0$^{14,18}$]hexacosa-1(24),2(26),3,8,14,17,21(25),22-octaene-13,20-dione (28)

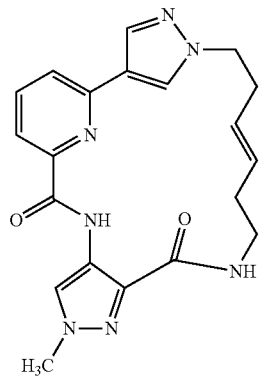 [SMILES: Cn1cc2c(n1)C(=O)NCC/C=C/CCn1cc(cn1)-c1cccc(n1)C(=O)N2]

The title compound (the geometric isomer of Example 27), was obtained during the preparation of Example 27. LC-MS (M+1): 392. $^1$H NMR (400 MHz, Chloroform-d) δ 8.98 (d, J=0.7 Hz, 1H), 8.20 (s, 1H), 7.99-7.79 (m, 2H), 7.61 (dd, J=7.6, 2.1 Hz, 1H), 7.28 (d, J=1.9 Hz, 1H), 7.08 (s, 1H) 6.07-5.91 (m, 1H), 5.90-5.70 (m, 1H), 4.48-4.28 (m, 2H), 3.95 (s, 3H), 3.51 (q, J=6.3 Hz, 2H), 2.58 (q, J=12.6, 8.8 Hz, 2H), 2.40 (q, J=6.6 Hz, 2H).

Example 29 (9E)-16-methyl-4,5,12,15,16,19,25-heptaazatetracyclo[19.3.1.1$^{2,5}$.0$^{14,18}$]hexacosa-1(24),2(26),3,9,14,17,21(25),22-octaene-13,20-dione (29)

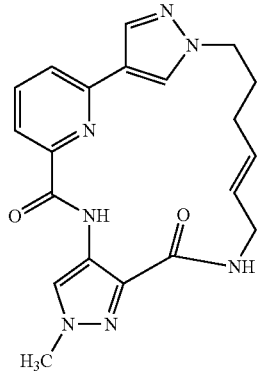 [SMILES: Cn1cc2c(n1)C(=O)NC/C=C/CCCn1cc(cn1)-c1cccc(n1)C(=O)N2]

The title compound was prepared in the same manner as Example 23, substituting compound 6-(1-Allyl-1H-pyrazol-4-yl)-pyridine-2-carboxylic acid (1-methyl-3-pent-4-enyl-carbamoyl-1H-pyrazol-4-yl)-amide with compound of 6-(1-Pent-4-enyl-1H-pyrazol-4-yl)-pyridine-2-carboxylic acid (3-allylcarbamoyl-1-methyl-1H-pyrazol-4-yl)-amide in the last step cyclization.

LC-MS (M+1): 392. 1H NMR (400 MHz, DMSO-d6) δ 12.28 (s, 1H), 8.81-8.66 (m, 2H), 8.29 (s, 1H), 8.15 (d, J=0.7 Hz, 1H), 8.07-7.95 (m, 1H), 7.90 (dt, J=7.9, 2.1 Hz, 1H), 7.83 (dd, J=7.5, 1.0 Hz, 1H), 5.80 (d, J=15.5 Hz, 1H), 5.61-5.48 (m, 1H), 4.28 (t, J=5.9 Hz, 2H), 3.99 (s, 3H), 2.65 (s, 2H), 2.38-2.28 (m, 2H), 2.06-1.76 (m, 2H).

Example 30 (9Z)-16-methyl-4,5,12,15,16,19,25-heptaazatetracyclo[19.3.1.1$^{2,5}$.0$^{14,18}$]hexacosa-1(24),2(26),3,9,14,17,21(25),22-octaene-13,20-dione (30)

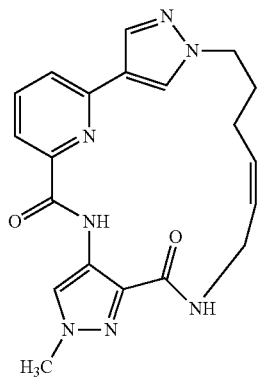 [SMILES: Cn1cc2c(n1)C(=O)NC/C=C\CCCn1cc(cn1)-c1cccc(n1)C(=O)N2]

The title compound (the geometric isomer of Example 29), was obtained during the preparation of Example 29. LC-MS (M+1): 392. 1H NMR (400 MHz, DMSO-d6) δ 12.70 (s, 1H), 8.88 (s, 1H), 8.77 (t, J=6.1 Hz, 1H), 8.37-8.22 (m, 1H), 8.11 (d, J=1.6 Hz, 1H), 8.02 (t, J=8.0 Hz, 1H), 7.94-7.76 (m, 2H), 5.55 (dd, J=8.2, 4.4 Hz, 1H), 5.40 (t, J=9.0 Hz, 1H), 4.28 (t, J=6.0 Hz, 2H), 3.96 (s, 3H), 3.89-3.68 (t, 2H), 2.77-2.56 (s, 2H), 2.19-2.01 (m, 2H).

Scheme 9:

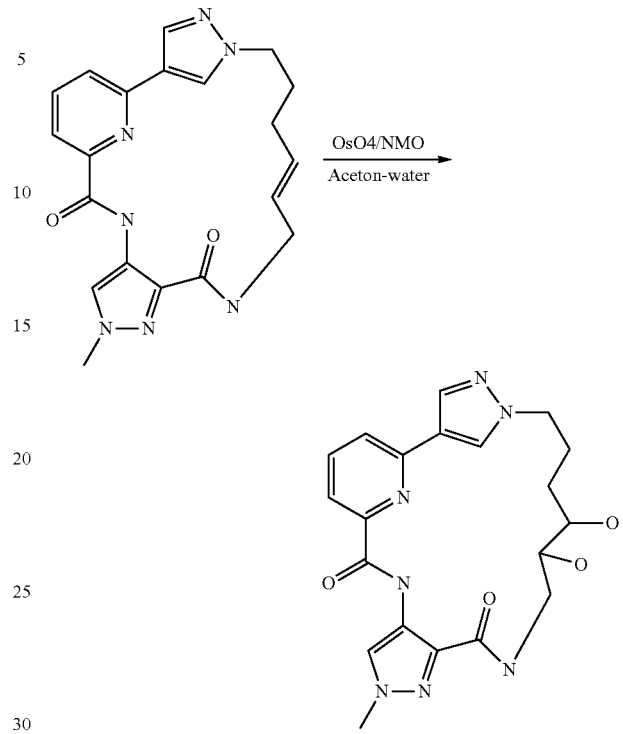

Example 31 9,10-dihydroxy-16-methyl-4,5,12,15,16,19,25-heptaazatetracyclo[19.3.1.1$^{2,5}$.0$^{14,18}$]hexacosa-1(24),2(26),3,14,17,21(25),22-heptaene-13,20-dione (31)

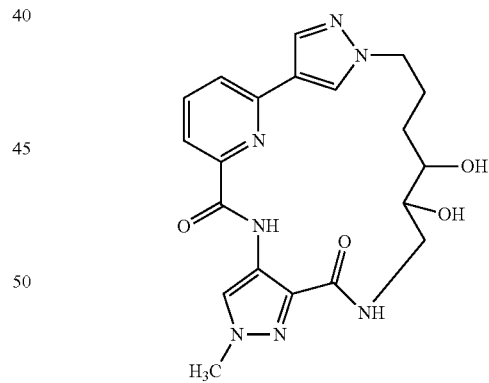

To a stirring solution of Example 29 (30. mg; 0.08 mmol; 1.00 eq.) in a mixture of acetone (2 mL) and water (0.2 ml), were added osmium tetroxide (155 mg; 0.02 mmol, 2.5% in isopropanol); 0.20 eq.) and 4-methylmorpholine n-oxide (17 mg; 0.15 mmol; 2.00 eq.). The mixture was stirred at RT overnight, reaction was completed. After removal of the solvents, the crude was purified by prep HPLC (20-80% ACN in water) to yield the title compound. LC-MS (M+1): 426. 1H NMR (400 MHz, DMSO-d6) δ 12.73 (s, 1H), 9.11 (s, 1H), 8.64-8.53 (m, 1H), 8.32 (s, 1H), 8.15-7.94 (m, 2H), 7.85-7.88 (m, 2H), 4.75 (s, 1H), 4.58 (m, 1H), 4.30 (s, 1H), 4.16-4.05 (m, 2H), 3.96 (s, 3H), 3.70-3.71 (m, 1H), 3.68 (s, 1H). 3.04-2.81 (m, 1H), 2.71-2.64 (m, 1H), 2.34-2.28 (m, 1H), 2.15-2.10 (m, 1H), 1.90-1.84 (m, 1H).

Example 32 7,8-dihydroxy-16-methyl-4,5,12,15,16, 19,25-heptaazatetracyclo[19.3.1.1$^{2,5}$.0$^{14,18}$]hexacosa-1(24),2(26),3,14,17,21(25),22-heptaene-13,20-dione (32)

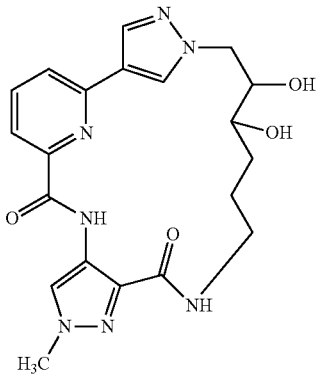 [SMILES: Cn1cc2c(n1)C(=O)NCCCC(O)C(O)Cn1cc(cn1)-c1cccc(n1)C(=O)N2]

The title compound was prepared in the same manner as Example 31, substituting Example 29 with Example 23 for the oxidation reaction. LC-MS (M+1): 426.
$^1$H NMR (400 MHz, DMSO-d$_6$) δ 12.83 (s, 1H), 9.41 (d, J=2.8 Hz, 1H), 8.80 (s, 1H), 8.32 (d, J=2.7 Hz, 1H), 8.08-7.98 (m, 2H), 7.85 (dt, J=28.5, 4.9 Hz, 2H), 4.79 (s, 1H), 4.68 (d, J=7.6 Hz, 1H), 4.46 (d, J=6.5 Hz, 1H), 4.33-4.17 (m, 2H), 3.95 (d, J=2.8 Hz, 3H), 3.89 (s, 1H), 3.56 (s, 1H), 2.96 (s, 2H), 1.74 (d, J=12.2 Hz, 1H), 1.64 (s, 1H), 1.56-1.54 (m, 2H).

Example 33 8,9-dihydroxy-16-methyl-4,5,12,15,16, 19,25-heptaazatetracyclo[19.3.1.1$^{2,5}$.0$^{14,18}$]hexacosa-1(24),2(26),3,14,17,21(25),22-heptaene-13,20-dione (33)

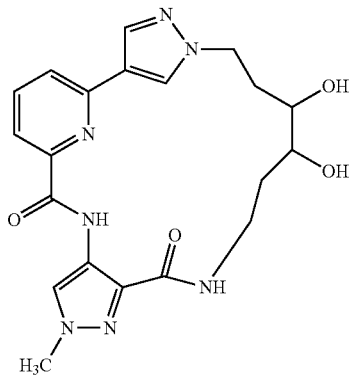 [SMILES: Cn1cc2c(n1)C(=O)NCCC(O)C(O)CCn1cc(cn1)-c1cccc(n1)C(=O)N2]

The title compound was prepared in the same manner as Example 31, substituting Example 29 with Example 28 for the oxidation reaction. LC-MS (M+1): 426. $^1$H NMR (400 MHz, Methanol-d4) δ 9.39 (s, 1H), 8.23 (d, J=3.1 Hz, 1H), 8.00-7.97 (m, 2H), 7.89 (d, J=7.1 Hz, 1H), 7.80 (d, J=7.8 Hz, 1H), 4.51-4.49 (m, 1H), 4.35-4.30 (m, 1H), 4.05-4.01 (m, 1H), 3.98 (s, 3H), 3.82 (d, J=7.6 Hz, 1H), 3.63-3.59 (m, 1H), 3.52 (s, 1H), 3.15 (s, 1H), 2.67 (s, 2H), 2.36 (s, 1H), 2.05-1.92 (m, 2H).

Example 34 (9E)-17-methyl-4,5,13,16, 17,20,26-heptaazatetracyclo[20.3.1.1$^{2,5}$.0$^{15,19}$]heptacosa-1(25),2(27),3,9,15,18,22(26),23-octaene-14,21-dione (34)

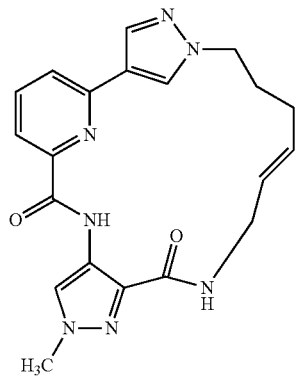 [SMILES: Cn1cc2c(n1)C(=O)NC/C=C/CCCn1cc(cn1)-c1cccc(n1)C(=O)N2]

The title compound was prepared in the same manner as Example 23, substituting compound 6-(1-Allyl-1H-pyrazol-4-yl)-pyridine-2-carboxylic acid (1-methyl-3-pent-4-enyl-carbamoyl-1H-pyrazol-4-yl)-amide with compound 6-(1-Pent-4-enyl-1H-pyrazol-4-yl)-pyridine-2-carboxylic acid (3-but-3-enylcarbamoyl-1-methyl-1H-pyrazol-4-yl)-amide in the last step cyclization.
LC-MS (M+1): 406. 1H NMR (400 MHz, Chloroform-d) δ 12.69 (s, 1H), 9.0 (s, 1H), 8.27 (s, 1H), 8.05-7.90 (m, 2H), 7.90-7.78 (m, 1H), 7.64 (dd, J=7.8, 1.7 Hz, 1H), 7.06 (d, J=8.4 Hz, 1H), 6.06 (dt, J=14.9, 7.3 Hz, 1H), 5.37 (dt, J=14.7, 6.7 Hz, 1H), 4.32 (d, J=7.2 Hz, 2H), 3.96 (s, 3H). 3.61 (d, J=8.3 Hz, 2H), 3.38-3.30 (m, 1H), 2.59 (d, J=8.7 Hz, 1H), 2.39 (dt, J=28.5, 8.0 Hz, 2H), 2.23-2.11 (m, 2H).

Example 35 17-methyl-4,5,13,16,17,20,26-heptaaza-tetracyclo[20.3.1.1$^{2,5}$.0$^{15,19}$]heptacosa-1(25),2(27),3, 15,18,22(26),23-heptaene-14,21-dione (35)

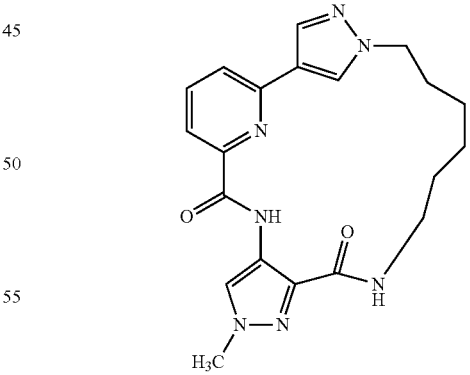

To a solution of Example 34 (15 mg) in a mixture of MeOH (5 ml) and EA (20 ml), was added 15 mg of 10% Pd/C wet. The mixture was put on parr shaker for 1 hr at 40 psi. The reaction mixture was filtered. The title compound was yielded as a white solid after the removal of the solvents. LC-MS (M+1): 408.
1H NMR (400 MHz, Chloroform-d) δ 12.44 (s, 1H), 8.81 (d, J=0.7 Hz, 1H), 8.28 (s, 1H), 8.06-7.92 (m, 2H), 7.85 (t, J=7.8 Hz, 1H), 7.63 (dd, J=7.8, 1.0 Hz, 1H), 6.99 (t, J=6.9 Hz, 1H), 4.48-4.29 (m, 2H), 3.99 (s, 3H), 3.56 (q, J=6.5 Hz, 2H), 2.03-1.83 (m, 2H), 1.76-1.61 (m, 4H), 1.56-1.45 (m, 2H), 0.96-0.73 (m, 2H).

Example 36 9,10-dihydroxy-17-methyl-4,5,13,16,17,20,26-heptaazatetracyclo[20.3.1.1$^{2,5}$.0$^{13,19}$]heptacosa-1(25),2(27),3,15,18,22(26),23-heptaene-14,21-dione (36)

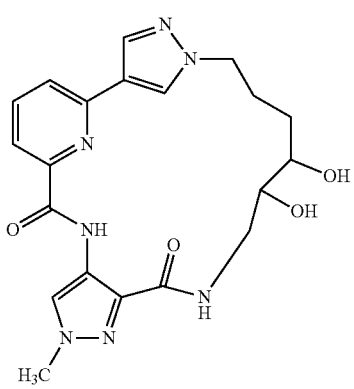 [SMILES: Cn1cc2c(n1)C(=O)NCC(O)C(O)CCCn1cc(cn1)-c1cccc(n1)C(=O)N2]

The title compound was prepared in the same manner as Example 31, substituting Example 29 with Example of 34. LC-MS (M+1): 439
$^1$H NMR (400 MHz, DMSO-d$_6$) δ 12.79 (s, 1H), 8.75 (d, J=8.5 Hz, 1H), 8.67 (s, 1H), 8.63 (s, 1H), 8.36 (s, 1H), 8.20-8.15 (m, 1H), 7.93 (d, J=8.1 Hz, 1H), 7.85 (d, J=7.7 Hz, 1H), 4.34-4.26 (m, 2H), 3.99 (s, 3H), 3.75-3.70 (m, 2H), 2.75 (s, 1H), 2.42 (s, 1H). 2.20-2.03 (m, 2H), 1.89-1.80 (m, 2H), 1.72-1.65 (m, 2H), 1.48-1.40 (m, 2H).

Example 37 (7Z)-16-methyl-4,5,12,15,16,19,25-heptaazatetracyclo[19.3.1.1$^{2,5}$.0$^{14,18}$]hexacosa-1(24),2(26),3,7,14,17,21(25),22-octaene-13,20-dione (37)

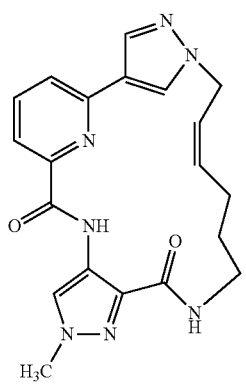 [SMILES: Cn1cc2c(n1)C(=O)NCCC/C=C\Cn1cc(cn1)-c1cccc(n1)C(=O)N2]

The title compound (the geometric isomer of Example 23) was yielded as the minor product during the preparation of Example 23. LC-MS (M+1): 392. 1H NMR (400 MHz, DMSO-d6) δ 12.87 (s, 1H), 8.96 (s, 1H), 8.74 (t, J=6.1 Hz, 1H), 8.29 (s, 1H), 8.18 (s, 1H), 8.01 (t, J=7.7 Hz, 1H), 7.93 (d, J=7.8 Hz, 1H), 7.83 (d, J=7.6 Hz, 1H), 6.34 (dt, J=14.5, 7.0 Hz, 1H), 5.87 (dt, J=14.7, 6.9 Hz, 1H), 4.82 (d, J=7.0 Hz, 2H), 3.94 (s, 3H), 3.42-3.27 (d, J=20.1 Hz, 2H), 2.17-2.05 (m, 2H), 1.81-1.68 (m, 2H).

Scheme 10

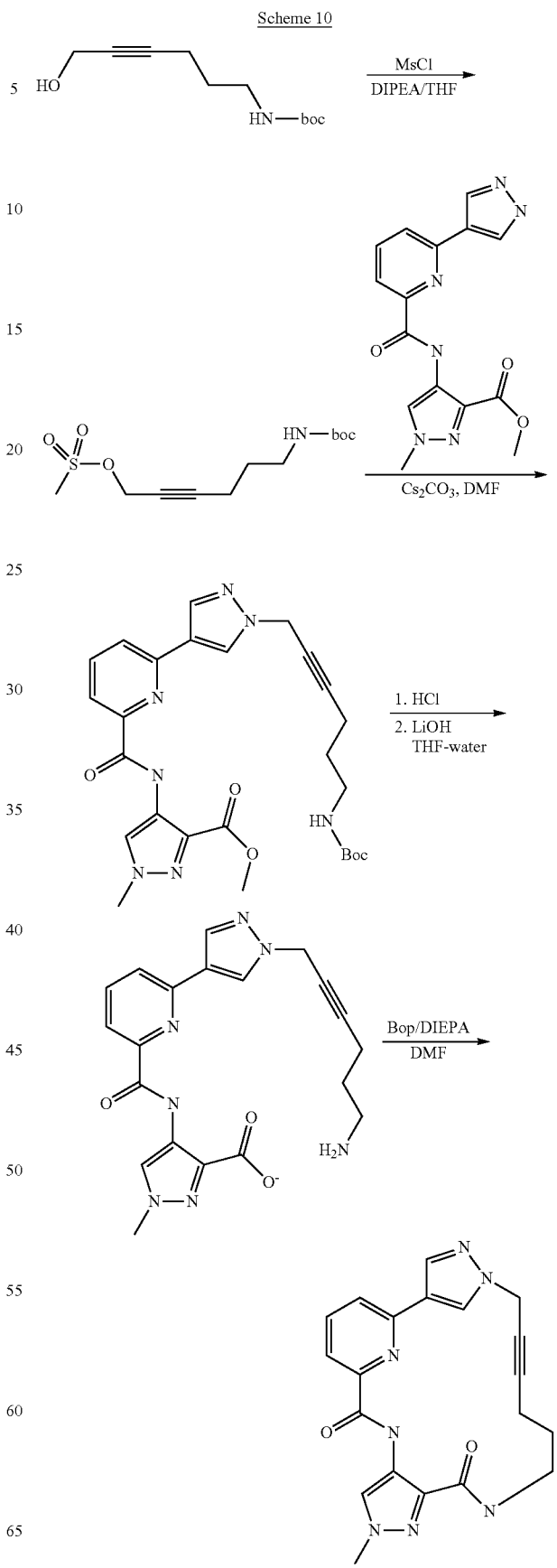

103

Methanesulfonic acid
6-tert-butoxycarbonylamino-hex-2-ynyl ester

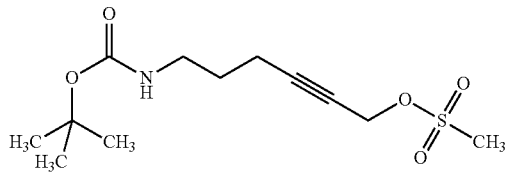 [SMILES: CC(C)(C)OC(=O)NCCCC#CCOS(C)(=O)=O]

To a stirring solution of (6-hydroxy-hex-4-ynyl)-carbamic acid tert-butyl ester (100. mg; 0.47 mmol; 1.00 eq.) and ethyl-diisopropyl-amine (0.12 ml; 0.70 mmol; 1.50 eq.) in THF (6.0 ml), was added methanesulfonyl chloride (0.05 ml; 0.59 mmol; 1.25 eq.) dropwise at rt and stirred for 2 h. The reaction mixture was diluted with EA, washed with brine, dried and concentrated to yield the crude title compound (136. mg; 0.47 mmol), which was used directly for the next step reaction. LC-MS (M+1): 292.

4-({6-[1-(6-tert-Butoxycarbonylamino-hex-2-ynyl)-1H-pyrazol-4-yl]-pyridine-2-carbonyl}-amino)-1-methyl-1H-pyrazole-3-carboxylic acid methyl ester

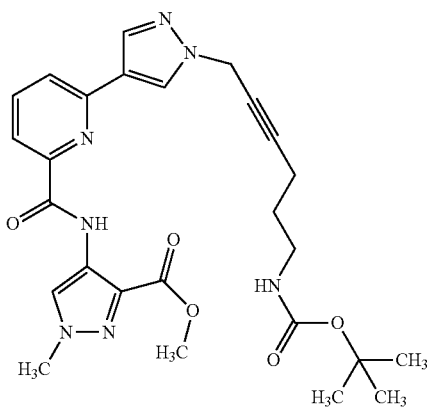 [SMILES: COC(=O)c1nn(C)cc1NC(=O)c1cccc(-c2cnn(CC#CCCCNC(=O)OC(C)(C)C)c2)n1]

A reaction mixture of cesium carbonate (304. mg; 0.93 mmol; 2.00 eq.) and 1-methyl-4-{[6-(1H-pyrazol-4-yl)-pyridine-2-carbonyl]-amino}-1H-pyrazole-3-carboxylic acid methyl ester (152 mg; 0.47 mmol; 1.00 eq.) in DMF (1.0 ml) was stirred at rt for 15 min. added methanesulfonic acid 6-tert-butoxycarbonylamino-hex-2-ynyl ester (136 mg; 0.47 mmol; 1.00 eq.). The resulting mixture was stirred at 60° C. for 2 h. The reaction mixture was poured into water, exacted with EtOAc and washed with brine, dried and concentrated to give the crude title compound (216 mg, yield 89%), which was used directly for the next step reaction. LC-MS (M+1): 522.

104

4-({6-[1-(6-Amino-hex-2-ynyl)-1H-pyrazol-4-yl]-pyridine-2-carbonyl}-amino)-1-methyl-1H-pyrazole-3-carboxylic acid methyl ester

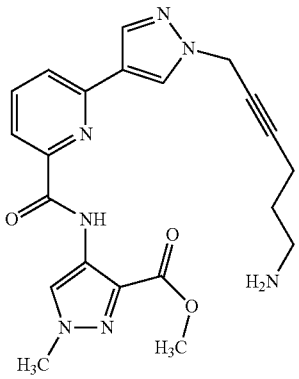 [SMILES: COC(=O)c1nn(C)cc1NC(=O)c1cccc(-c2cnn(CC#CCCCN)c2)n1]

To a solution of the crude 4-({6-[1-(6-tert-Butoxycarbonylamino-hex-2-ynyl)-1H-pyrazol-4-yl]-pyridine-2-carbonyl}-amino)-1-methyl-1H-pyrazole-3-carboxylic acid methyl ester (210 mg; 0.40 mmol; 1.00 eq.) in methanol (2.0 ml) added 4.0M HCl in dioxane hydrogen chloride (1.61 ml; 6.44 mmol; 16.00 eq.) at rt, the mixture was stirred at rt for 2 h. The reaction mixture was concentrated and purified by prep-HPLC (Waters, basic, 10-50% ACN in water) to yield the title compound (96 mg; yield 57%). LC-MS (M+1): 422.

Lithium 4-({6-[1-(6-amino-hex-2-ynyl)-1H-pyrazol-4-yl]-pyridine-2-carbonyl}-amino)-1-methyl-1H-pyrazole-3-carboxylate

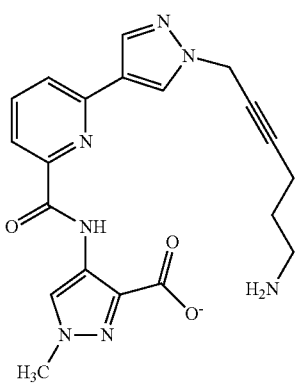 [SMILES: Cn1cc(NC(=O)c2cccc(-c3cnn(CC#CCCCN)c3)n2)c(C(=O)[O-])n1]

A mixture of 4-({6-[1-(6-amino-hex-2-ynyl)-1H-pyrazol-4-yl]-pyridine-2-carbonyl}-amino)-1-methyl-1H-pyrazole-3-carboxylic acid methyl ester (94 mg; 0.22 mmol; 1.00 eq.) and lithium hydroxide hydrate (18 mg; 0.45 mmol; 2.00 eq.) in THF (2.00 ml) and water (2.00 ml) was stirred at 40° C. for 1.5 h. The reaction mixture was concentrated to dryness to yield an off-white solid as the title compound. LC-MS (M+1): 407.

Example 38 16-methyl-4,5,12,15,16,19,25-heptaaza-tetracyclo[19.3.1.1$^{2,5}$.0$^{14,18}$]hexacosa-1(24),2(26),3,14,17,21 (25),22-heptaen-7-yne-13,20-dione (38)

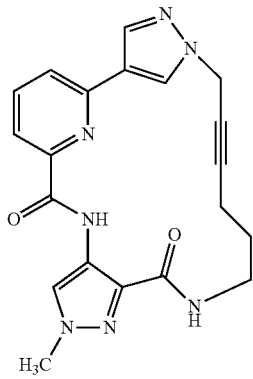 [SMILES: Cn1cc2c(n1)C(=O)NCCCC#CCn1cc(cn1)-c1cccc(n1)C(=O)N2]

A mixture of lithium 4-({6-[1-(6-amino-hex-2-ynyl)-1H-pyrazol-4-yl]-pyridine-2-carbonyl}-amino)-1-methyl-1H-pyrazole-3-carboxylate (90 mg; 0.20 mmol; 1.00 eq.) (benzotriazol-1-yloxy)tris(dimethylamino)phosphonium hexafluorophosphate (109.60 mg; 0.24 mmol; 1.20 eq.) and ethyl-diisopropyl-amine (0.07 ml; 0.40 mmol; 2.00 eq.) in DMF (18.00 ml; 200 V) was stirred at rt for 1.5 h. The reaction mixture was concentrated and the crude was purified by prep-HPLC (Waters, basic, 20-60% ACN in water) to yield the title compound as a white amorphous powder (15.00 mg; yield 19.2%). LC-MS (M+1): 390. 1H NMR (400 MHz, DMSO-d6) δ 13.03 (s, 1H), 9.39 (s, 1H), 8.67 (s, 1H), 8.31 (s, 1H), 8.23 (s, 1H), 8.13-7.75 (m, 3H), 5.13 (s, 2H), 3.97 (s, 3H), 3.59 (bs, 2H), 2.36 (bs, 2H), 1.71 (bs, 2H).

Example 39: Enzymatic Assays

IRAK4 Enzymatic Assay:

IRAK4 is a human purified recombinant enzyme (His-TEV-IRAK4 (1-460)).

In this assay, IRAK4 hydrolyses ATP, autophosphorylates and phosphorylates a Serine/Threonine generic peptidic substrate (STK: 61ST1BLC from CisBio International). Measurement of IRAK-4 inhibition is performed in 384-well format based on a luminescence assay (ADP-Glo™ Kinase Assay from Promega). Purified human recombinant IRAK4 (0.3 µg/ml) and serial diluted compounds in DMSO (range of concentration from 10 µM to 0.5 nM) or controls (1% DMSO) are incubated for 15 minutes at RT in assay buffer containing 50 mM Hepes pH 7.0, Fatty acid-free BSA 0.1%, Dithiothreitol (DTT) 2 mM, MgCl2 10 mM, EGTA 0.5 mM, Triton X-100 0.01%, MnCl2 5 mM. The kinase reaction is then initiated by the addition of ATP (2 µM) and the peptidic substrate STK1-biotin peptide (300 nM). After 2 hours of incubation at RT, the reaction is stopped and the unconsumed ATP depleted by the addition of ADP-Glo™ Reagent according to supplier instructions. After 40 minutes of incubation at RT, the Kinase Detection Reagent is then added to the assay plate according to supplier instructions. After 20 minutes of incubation at RT, the luminescence signal is measured with a plate-reading luminometer (PerkinElmer Envision or equivalent reader).

IRAK1 Enzymatic Assay:

IRAK1 is a human purified recombinant enzyme (His-TEV-IRAK1 (194-712))

In this assay, IRAK1 hydrolyses ATP and autophosphorylates. Measurement of IRAK-1 inhibition is performed in 384-well format based on luminescence assay (ADP-Glo™ Kinase Assay from Promega). Purified human recombinant IRAK1 (0.3 g/ml) and serial diluted compounds in DMSO (range of concentration from 10 µM to 0.5 nM) or controls (1% DMSO) are incubated for 15 minutes at RT in assay buffer containing 50 mM Hepes pH 7.0, Fatty acid-free BSA 0.1%, Dithiothreitol (DTT) 2 mM, MgCl2 10 mM, EGTA 0.5 mM, Triton X-100 0.01%. The kinase reaction is then initiated by the addition of ATP at a concentration of 1µM. After 2 hours of incubation at RT, the reaction is stopped and the unconsumed ATP depleted by the addition of ADP-Glo™ Reagent according to supplier instructions. After 40 minutes of incubation at RT, the Kinase Detection Reagent is then added to the assay plate according to supplier instructions. After 20 minutes of incubation at RT, the luminescence signal is measured with a luminometer (PerkinElmer Envision or equivalent reader).

Results are given in the following table.

| Compound | IRAK1 IC50 | IRAK4 IC50 |
| --- | --- | --- |
| 1 | *** | **** |
| 2 | *** | *** |
| 3 | *** | **** |
| 4 | ** | ** |
| 5 | **** | **** |
| 6 | * | * |
| 7 | ** | **** |
| 8 | * | *** |
| 9 | ** | **** |
| 10 | ** | *** |
| 11 | ** | **** |
| 12 | *** | **** |
| 13 | *** | **** |
| 14 | *** | **** |
| 15 | *** | **** |
| 16 | *** | **** |
| 17 | *** | **** |
| 18 | *** | **** |
| 19 | *** | **** |
| 20 | * | * |
| 21 | ** | *** |
| 22 | *** | **** |
| 23 | *** | **** |
| 24 | *** | **** |
| 25 | **** | **** |
| 26 | NT | NT |
| 27 | *** | **** |
| 28 | *** | **** |
| 29 | *** | **** |
| 30 | *** | **** |
| 31 | *** | **** |
| 32 | *** | **** |
| 33 | *** | **** |
| 34 | *** | **** |
| 35 | *** | **** |
| 36 | *** | **** |
| 37 | *** | **** |
| 38 | **** | **** |

* IC$_{50}$ > 5 µM
** IC$_{50}$ ranges from 1 µM-5 µM
*** IC$_{50}$ ranges from 100 nM-1.0 µM
**** IC$_{50}$ < 100 nM
NT Not Tested Example 40. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4 \cdot 2H_2O$, 28.48 g of $Na_2HPO_4 \cdot 12H_2O$ and 0.1 g of benzalkonium chloride in 940 mL of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 mL) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method for treating an IRAK-mediated disorder in a patient in need thereof, comprising the step of administering to said patient a compound of formula I,

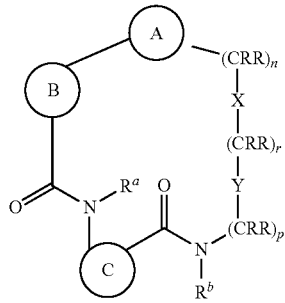

I or a pharmaceutically acceptable salt thereof, wherein:

Ring A is a 5-membered heterocylic ring having 1-4 heteroatoms independently selected from nitrogen oxygen, or sulfur, or a 5-membered monocyclic heteroaryl ring having 1-4 heteroatoms independently selected from nitrogen, oxygen, or sulfur; each of which is optionally substituted;

Ring B is a 6-membered aryl, or a 6 membered monocyclic heteroaryl ring having 1-4 heteroatoms independently selected from nitrogen, oxygen, or sulfur, each of which is optionally substituted;

Ring C is a 5-membered heterocyclic ring having 1-4 heteroatoms independently selected from nitrogen, oxygen, or sulfur, or a 5-membered monocyclic heteroaryl ring having 1-4 heteroatoms independently selected from nitrogen, oxygen, or sulfur, each of which is optionally substituted;

X is absent, —CH=CH—, —C≡C—, —O—, —S—, —SO₂—, —SO—, —C(O)—, —CO₂—, —C(O)N(R)—, —OC(O)N(R)—, —NRC(O)—, —NRC(O)N(R)—, —NRSO₂—, or —N(R)—;

Y is absent, a divalent $C_{3-10}$ aryl, a divalent 3-8 membered saturated or partially unsaturated carbocyclic ring, a divalent 3-7 membered heterocylic ring having 1-4 heteroatoms independently selected from nitrogen, oxygen, or sulfur, or a divalent 5-6 membered monocyclic heteroaryl ring having 1-4 heteroatoms independently selected from nitrogen, oxygen, or sulfur; each of which is optionally substituted;

each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or each R is independently —OR$^e$, —SR$^e$, —SOR$^e$, —SOR$^e$, —C(O)R$^e$, —CO₂R$^e$, —C(O)N(R)R$^e$, —OC(O)N(R)R$^e$, —NRC(O)R$^e$, —NRC(O)N(R)R$^e$, —NRSO₂R$^e$, or —Ni(R)R$^e$;

two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

$R^a$ is H or optionally substituted $C_{1-6}$ aliphatic;

$R^b$ is H or optionally substituted $C_{1-6}$ aliphatic;

each $R^e$ is independently H or optionally substituted $C_{1-6}$ aliphatic;

n is 1, 2, 3, 4, or 5;

p is 0, 1, 2, 3, or 4; and r is 0, 1, or 2.

2. The method of claim 1, wherein the disorder is selected from Rheumatoid Arthritis, Psoriatic arthritis, Osteoarthritis, Systemic Lupus Erythematosus, Lupus nephritis, Ankylosing Spondylitis, Systemic sclerosis, Multiple Sclerosis, Psoriasis, Type I diabetes, Type II diabetes, Inflammatory Bowel Disease Cronh's Disease and Ulcerative, Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Atherosclerosis, Celiac disease, DIRA (Deficiency of IL-1 Receptor Antagonist), Alzheimer's disease, and Cancer.

3. The method of claim 1, wherein Ring A is pyrazolidinyl, pyrazolinyl, or pyrazolyl; each of which is optionally substituted.

4. The method of claim 3, wherein Ring A is

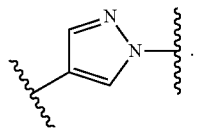 [SMILES: *c1cnn(*)c1]

5. The method of claim 1, wherein Ring B is phenyl, 2H,6H-1,5,2-dithiazinyl, pyrimidinyl, pyranyl, pyrazinyl, pyridazinyl, pyridinyl, pyridyl, pyrimidinyl, or triazinyl; each of which is optionally substituted.

6. The method of claim 5, wherein Ring B is phenyl or pyridinyl.

7. The method of claim 5, wherein Ring B is

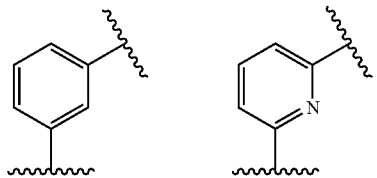

8. The method of claim 1, wherein Ring C is imidazolidinyl, imidazolinyl, imidazolyl, isoxazolyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrazolidinyl, pyrazolinyl, pyrazolyl, pyrrolidinyl, pyrrolinyl, 2H-pyrrolyl, pyrrolyl, 1,2,3-triazolyl, 1,2,4-triazolyl, 1,2,5-triazolyl, or 1,3,4-triazolyl; each of which is optionally substituted.

9. The method of claim 8, wherein Ring C is pyrazolidinyl, pyrazolinyl, or pyrazolyl; each of which is optionally substituted.

10. The method of claim 5, wherein Ring C is

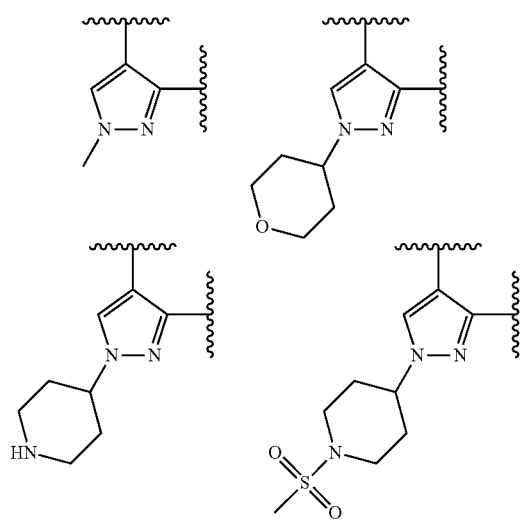

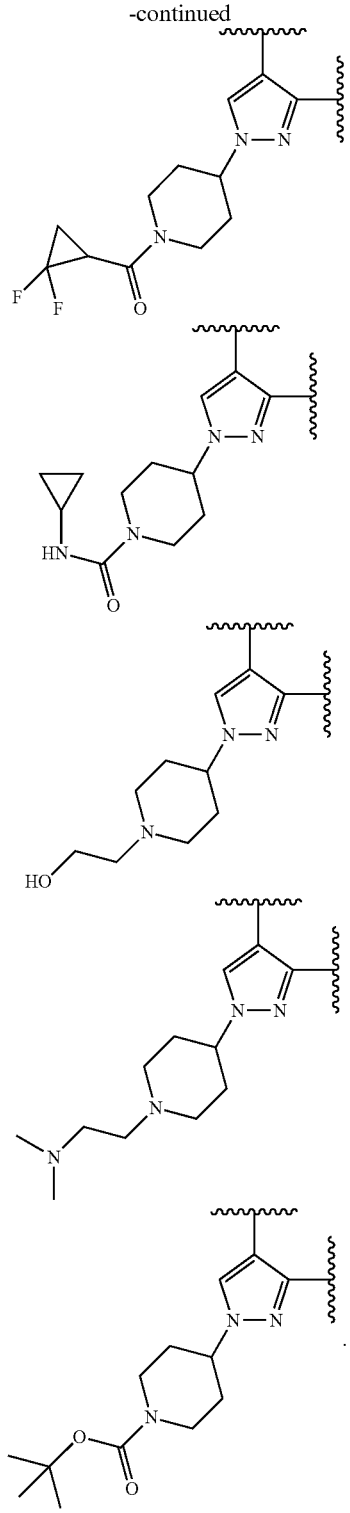

11. The method of claim 1, wherein X is absent.

12. The method of claim 1, wherein X is —CH=CH—, —C≡C—, —O—, —S—, —SO$_2$—, —SO—, —CO$_2$—, —OC(O)N(Me)-, or —N(Me)-.

13. The method of claim 1, wherein Y is absent.

14. The method of claim 1, wherein Y is an optionally substituted divalent pyrrolidine, piperidine, or morpholine.

15. The method of claim 14, wherein Y is

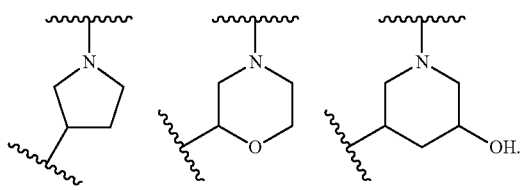

16. The method of claim 1, wherein the compound is of formula I-a,

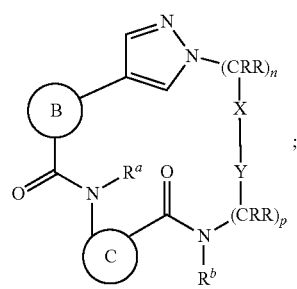

I-a or a pharmaceutically acceptable salt thereof.

17. The method of claim 1, wherein the compound is of formula I-b,

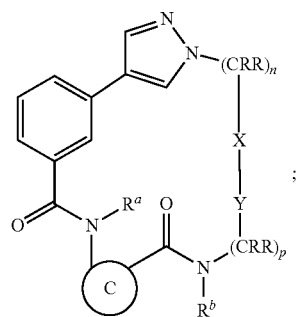

I-b or a pharmaceutically acceptable salt thereof.

18. The method of claim 1, wherein the compound is of formula I-c,

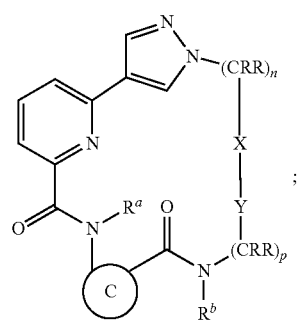

I-c or a pharmaceutically acceptable salt thereof.

19. The method of claim 1, wherein the compound is of formula I-d,

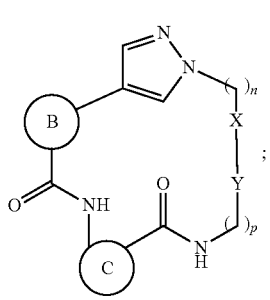

I-d or a pharmaceutically acceptable salt thereof.

20. The method of claim 1, wherein the compound is selected from Table 1

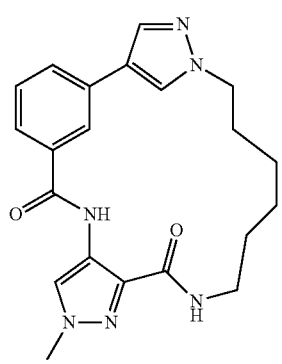

1

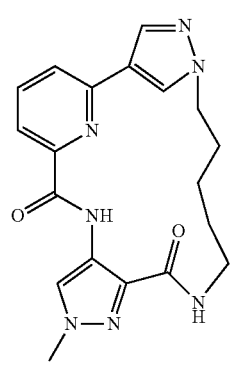

2

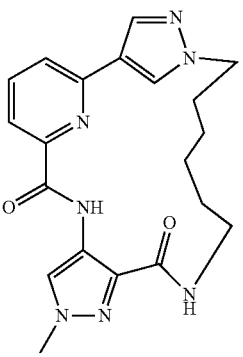

3

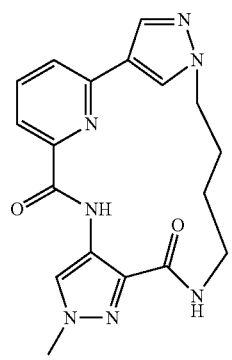
4
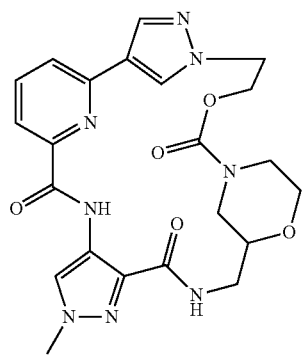
5
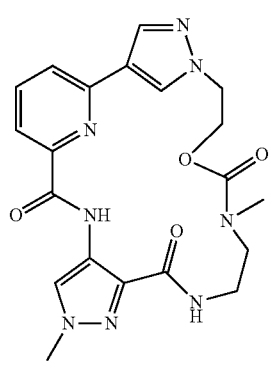
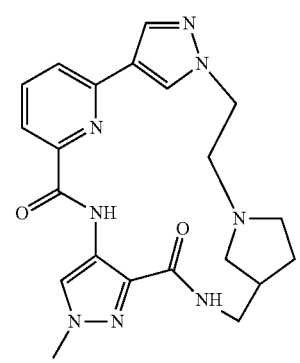
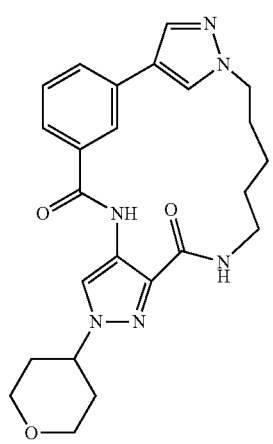
6
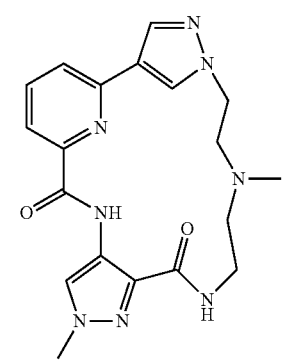
7
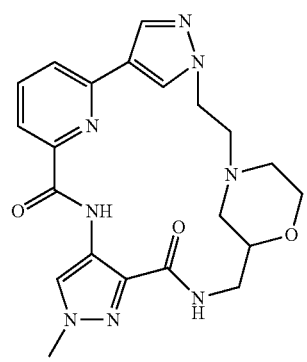
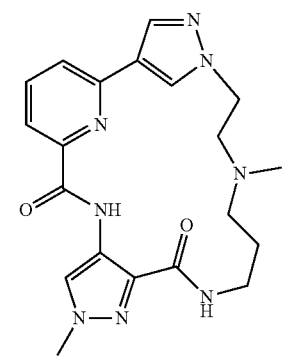

12
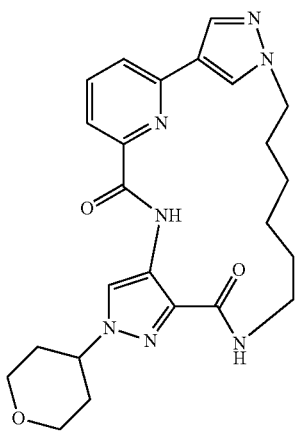
13
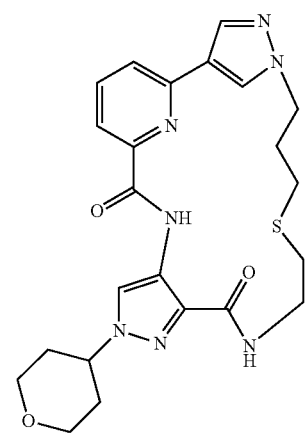
14
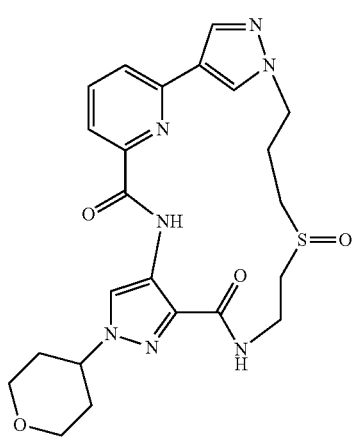
15
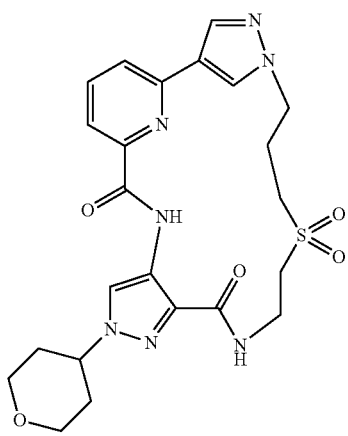
16
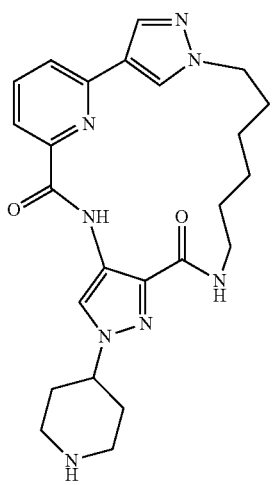
17

18
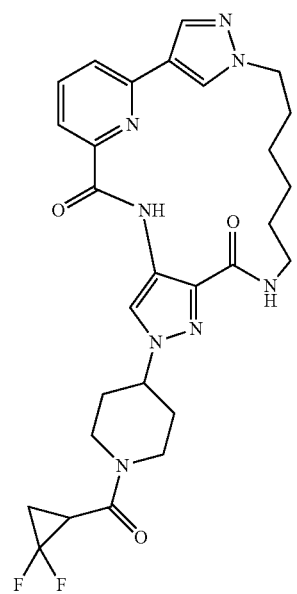
19
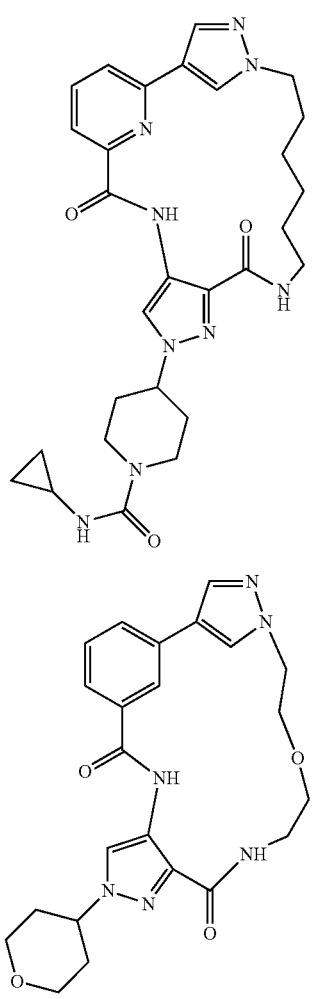
21
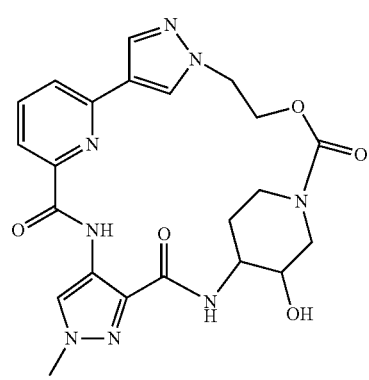
22
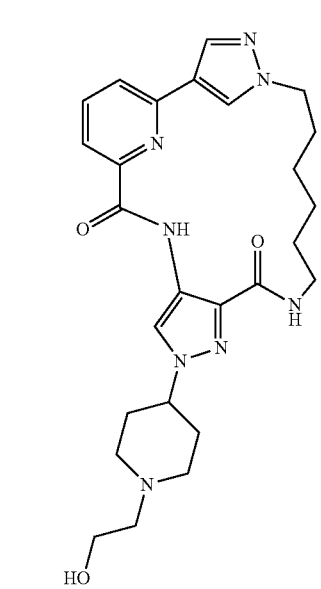
23
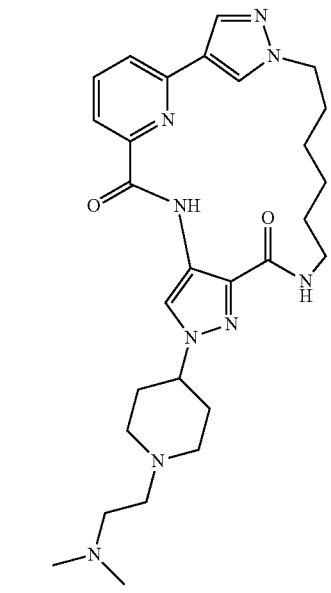

-continued
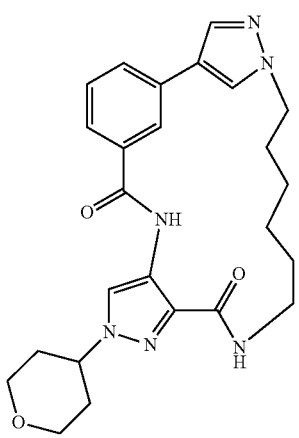
24
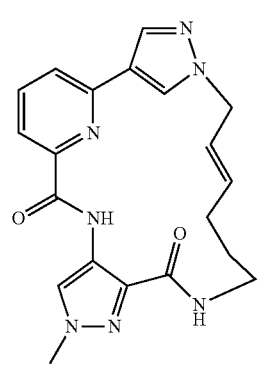
26
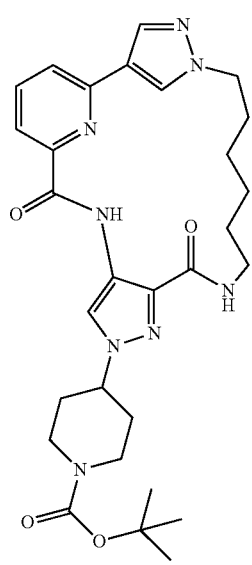
-continued
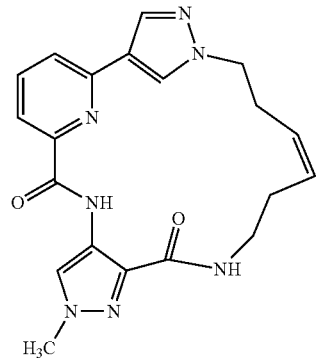
27
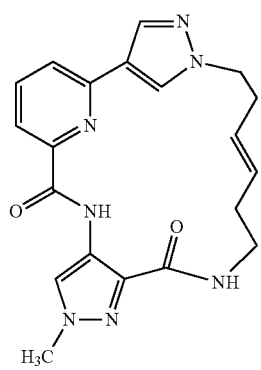
28
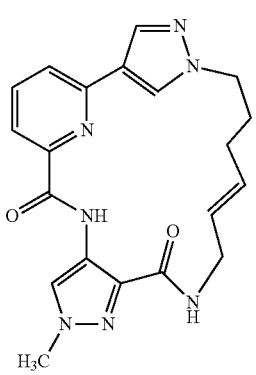
29
30

| 31 | 35 |
|---|---|
| 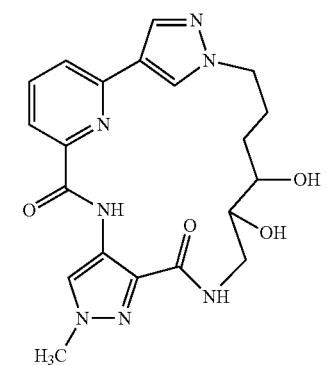 | 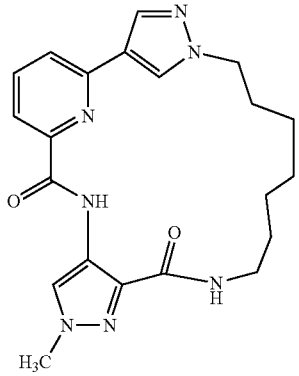 |
| 32 | 36 |
| 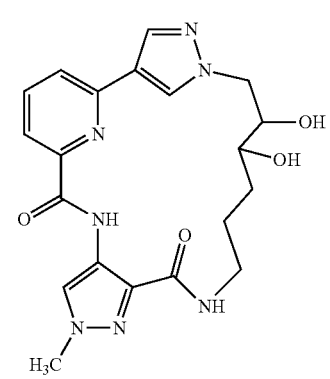 | 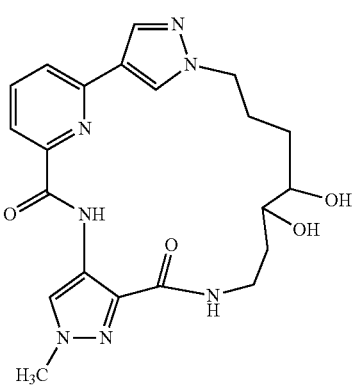 |
| 33 | 37 |
| 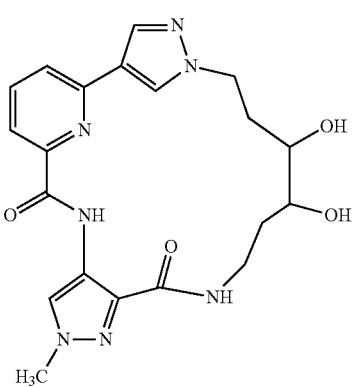 | 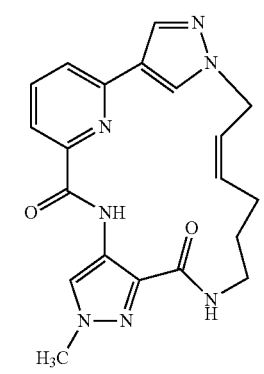 |
| 34 | 38 |
| 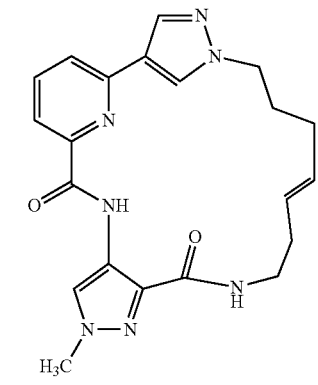 | 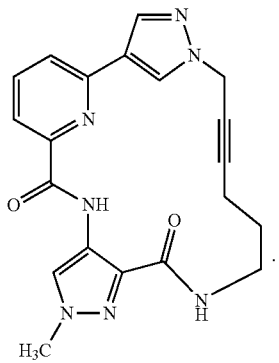 |
* * * * *